United States Patent
Gastwirt et al.

(10) Patent No.: US 11,111,304 B2
(45) Date of Patent: *Sep. 7, 2021

(54) FULLY HUMAN ANTIBODIES THAT BIND TO VASCULAR ENDOTHELIAL GROWTH FACTOR RECEPTOR 2 (VEGFR2)

(71) Applicant: Sorrento Therapeutics, Inc., San Diego, CA (US)

(72) Inventors: Randy Gastwirt, San Diego, CA (US); Heyue Zhou, San Diego, CA (US); John Dixon Gray, San Diego, CA (US); Guodi Lu, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/680,865

(22) Filed: Apr. 7, 2015

(65) Prior Publication Data

US 2017/0166644 A1 Jun. 15, 2017

(51) Int. Cl.
*C07K 16/28* (2006.01)
*A61K 39/395* (2006.01)
*A61K 39/00* (2006.01)
*A61K 45/06* (2006.01)

(52) U.S. Cl.
CPC ...... *C07K 16/2863* (2013.01); *A61K 39/3955* (2013.01); *A61K 45/06* (2013.01); *A61K 2039/505* (2013.01); *A61K 2039/507* (2013.01); *C07K 2317/21* (2013.01); *C07K 2317/55* (2013.01); *C07K 2317/56* (2013.01); *C07K 2317/622* (2013.01); *C07K 2317/76* (2013.01); *C07K 2317/92* (2013.01); *C07K 2317/94* (2013.01)

(58) Field of Classification Search
CPC ............ C07K 16/2863; C07K 2317/21; C07K 2317/55; C07K 2317/56; C07K 2317/622; C07K 2317/92; C07K 2317/94; A61K 45/06; A61K 39/3955; A61K 2039/505
See application file for complete search history.

(56) References Cited

U.S. PATENT DOCUMENTS

2009/0306348 A1 12/2009 Goldstein et al.
2011/0038874 A1 2/2011 Tong et al.

FOREIGN PATENT DOCUMENTS

CN 101495136 A 7/2009
WO 3230984 A1 4/2002
WO 2006017538 A2 2/2006

OTHER PUBLICATIONS

Paul, WE. Fundamental Immunology, 3rd ed. (1993) Raven Press, NY, Chap. 9, pp. 292-295.*
Rudikoff S. et al. Proc. Natl. Acad. Sci. USA (1982), 79:1979-1983.*
Colman, PM. Research in Immunology (1994), Elsevier, NY, 145(1):33-36.*
Near RI, et al. Molecular Immunology (1993). 30(4):369-377.*
Extended European Search Report for EP13770063.9 dated Jun. 24, 2016, 15 pages.
International Preliminary Report on Patentability for PCT/US2013/034732 dated Oct. 1, 2014, 9 pages.
International Search Report for PCT/US2013/034732 dated Sep. 30, 2013, 6 pages.
Zhang, Haifan et al., "Inhibition of both the autocrine and the paracrine growth of human leukemia with a fully human antibody directed against vascular endothelial growth factor receptor 2", Leukemia and Lymphoma, Informa Healthcare, 2004, 1887-1897, vol. 45, No. 9, US.
Jimenez, X et al., (2005), "A recombinant, fully human, bispecific antibody neutralizes the biological activities mediated by both vascular endothelial growth factor receptors 2 and 3," Molecular cancer therapeutic, vol. 4, No. 3, 427-434.
Miao, H. Q., (2006), "Potent neutralization of VEGF biological activities with a fully human antibody Fab fragment directed against VEGF receptor 2," Biochemical and biophysical reasearch communications, vol. 345, No. 1,438-445.
Wicki et al. "Targeting Tumor-Associated Endothelial Cells: Anti-VEGFR2 Immunoliposomes, Mediate Tumor Vessel Disruption and Inhibit Tumor Growth," Clin. Cancer Res., vol. 18, No. 2, Jan. 15, 2012 (Jan. 15, 2012).
Zhu, Z et al., (2003), "Inhibition of human leukemia in an animal model with human antibodies directed against vascular endothelial growth factor receptor 2. Correlation between antibody affinity and biological activity," Leukemia, vol. 17, No. 3, 604-611.

* cited by examiner

*Primary Examiner* — Robert S Landsman
(74) *Attorney, Agent, or Firm* — McNeill Baur PLLC

(57) ABSTRACT

There is disclosed compositions and methods relating to anti-VEGFR2 antibodies. More specifically, there is disclosed fully human antibodies that bind VEGFR2, VEGFR2-binding fragments and derivatives of such antibodies, and VEGFR2-binding polypeptides comprising such fragments. Further still, there is disclosed antibody fragments and derivatives and polypeptides, and methods of using such antibodies, antibody fragments and derivatives and polypeptides, including methods of treating or diagnosing subjects having various cancers.

12 Claims, 16 Drawing Sheets

Specification includes a Sequence Listing.

Figure 5 Inhibition of VEGFR-2 phosphorylation stimulated by VEGF in HUVECs

FULLY HUMAN ANTIBODIES THAT BIND TO VASCULAR ENDOTHELIAL GROWTH FACTOR RECEPTOR 2 (VEGFR2)

CROSS REFERENCE TO RELATED APPLICATIONS

This patent application is a continuation of U. S. patent application Ser. No. 13/854,071, filed Mar. 30, 2013 (now U.S. Pat. No. 9,029,510, issued May 12, 2015). U.S. patent application Ser .No. 13/854,071 claims the benefit of the filing date under 35 U.S.C. § 119(e) of U.S. Provisional Application No. 61/618,658, filed Mar. 30, 2012.

TECHNICAL FIELD

The present disclosure provides compositions and methods for fully human anti-VEGFR2 antibodies. More specifically, the present disclosure provides human antibodies that bind VEGFR2, VEGFR2-binding fragments and derivatives of such antibodies, and VEGFR2-binding polypeptides comprising such fragments. Further still, the present disclosure provides antibody fragments and derivatives and polypeptides, and methods of using such antibodies, antibody fragments and derivatives and polypeptides, including methods of treating or diagnosing subjects having VEGFR2-related disorders or conditions.

BACKGROUND

Angiogenesis is an important cellular event in which vascular endothelial cells proliferate, prune and reorganize to form new vessels from preexisting vascular networks. There are compelling evidences that the development of a vascular supply is essential for normal and pathological proliferative processes (Folkman and Klagsbrun (1987) *Science* 235:442-447). Delivery of oxygen and nutrients, as well as the removal of catabolic products, represent rate-limiting steps in the majority of growth processes occurring in multicellular organisms. Thus, it has been generally assumed that the vascular compartment is necessary, not only for organ development and differentiation during embryogenesis, but also for wound healing and reproductive functions in the adult.

Angiogenesis is also implicated in the pathogenesis of a variety of disorders, including but not limited to, cancer, proliferative retinopathies, age-related macular degeneration, rheumatoid arthritis (RA), and psoriasis. Angiogenesis is essential for the growth of most primary solid tumors and their subsequent metastasis. Tumors can absorb sufficient nutrients and oxygen by simple diffusion up to a size of 1-2 mm, at which point their further growth requires the elaboration of vascular supply. This process is thought to involve recruitment of the neighboring host mature vasculature to begin sprouting new blood vessel capillaries, which grow towards, and subsequently infiltrate, the tumor mass. In addition, tumor angiogenesis involves the recruitment of circulating endothelial precursor cells from the bone marrow to promote neovascularization Kerbel, *Carcinogenesis* 21:505-515, 2000; and Lynden et al., *Nat. Med.* 7:1194-1201, 2001.

While induction of new blood vessels is considered to be the predominant mode of tumor angiogenesis, some tumors may grow by co-opting existing host blood vessels. The co-opted vasculature then regresses, leading to tumor regression that is eventually reversed by hypoxia-induced angiogenesis at the tumor margin. Holash et al., *Science* 284: 1994-1998, 1999.

In many instances, the process begins with the activation of existing vascular endothelial cells in response to a variety of cytokines and growth factors. In cancer, tumor released cytokines or angiogenic factors stimulate vascular endothelial cells by interacting with specific cell surface receptors. The activated endothelial cells secrete enzymes that degrade the basement membrane of the vessels, allowing invasion of the endothelial cells into the tumor tissue. Once situated, the endothelial cells differentiate to form new vessel offshoots of pre-existing vessels. The new blood vessels provide nutrients to the tumor, facilitating further growth, and also provide a route for metastasis.

Numerous angiogenic factors have been identified, including the particularly potent factor VEGF. VEGF was initially purified from the conditioned media of folliculostellate cells and from a variety of cell lines. Various forms of VEGF bind as high affinity ligands to a suite of VEGF receptors (VEGFRs). VEGFRs are tyrosine kinase receptors, many of which are important regulators of angiogenesis. The VEGFR family includes 3 major subtypes: VEGFR1, VEGFR2 (also known as Kinase Insert Domain Receptor, "KDR", in humans), and VEGFR3. Among VEGF forms, VEGF-A, VEGF-C and VEGF-D are known to bind and activate VEGFR2.

VEGF, acting through its cognate receptors, can function as an endothelial specific mitogen during angiogenesis. In addition, there is substantial evidence that VEGF and VEGFRs are up-regulated in conditions characterized by inappropriate angiogenesis, such as cancer. As a result, a great deal of research has focused on the identification of therapeutics that target and inhibit VEGFs or VEGFRs.

Therapeutic approaches that target or inhibit VEGFs or VEGFRs include antibodies, peptides, and small molecule kinase inhibitors. Of these, antibodies are widely used for in vivo recognition and inhibition of ligands and cellular receptors. Highly specific antibodies have been used to block receptor-ligand interaction, thereby neutralizing the biological activity of the components, and also to specifically deliver toxic agents to cells expressing the cognate receptor on its surface. As a result, there remains a need for effective therapeutics that can specifically inhibit VEGF/VEGFR pathways as a treatment for disorders characterized by inappropriate angiogenesis, such as cancer.

The anti-VEGF antibody "Bevacizumab (BV)", also known as "rhuMAb VEGF" or "Avastin®" is a recombinant humanized anti-VEGF monoclonal antibody generated according to Presta et al., *Cancer Res.* 57:4593-4599, 1997. It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 daltons and is glycosylated.

SUMMARY

The anti-VEGFR2 binding proteins described herein may be used, for example, to detect VEGFR2 in vivo or in vitro. Additionally, certain VEGFR2 binding proteins described herein may be used to treat diseases associated with VEGFR2-mediated biological activity. For example, VEGFR2 mediates the pro-angiogenic effects of VEGF, and accordingly, certain VEGFR2 binding proteins of the disclosure may be used to inhibit angiogenesis in a human patient. Certain VEGFR2 binding proteins of the disclosure may be used to treat disorders such as cancers, inflammatory diseases, autoimmune diseases and retinopathies. Many disorders related to the hyperproliferation of cells of a tissue will include an angiogenic component, and thus it is expected that certain VEGFR2 binding proteins described herein can be used to treat such disorders.

The present disclosure provides a fully human antibody of an IgG class that binds to a VEGFR2 epitope with a binding affinity of at least $10^{-6}$M, that has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called VB-A2 herein), SEQ ID NO. 3/SEQ ID NO. 4 (called VB-A3 herein), SEQ ID NO. 5/SEQ ID NO. 6 (called VB-A7 herein), SEQ ID NO. 7/SEQ ID NO. 8 (called VBV-A7 herein), SEQ ID NO. 9/SEQ ID NO. 10 (called VB-A9 herein), SEQ ID NO. 11/SEQ ID NO. 12 (called VB-A10 herein), SEQ ID NO. 13/SEQ ID NO. 14 (called VB-B6 herein), SEQ ID NO. 15/SEQ ID NO. 16 (called VB-B10 herein), SEQ ID NO. 17/SEQ ID NO. 18 (called VB-D5 herein), SEQ ID NO. 19/SEQ ID NO. 20 (called VB-D6 herein), SEQ ID NO. 21/SEQ ID NO. 22 (called VB-D11 herein), SEQ ID NO. 23/SEQ ID NO. 24 (called VB-E1 herein), SEQ ID NO. 25/SEQ ID NO. 26 (called VB-E2 herein), SEQ ID NO. 27/SEQ ID NO. 28 (called VB-E7 herein), SEQ ID NO. 29/SEQ ID NO. 30 (called VB-F2 herein), SEQ ID NO. 31/SEQ ID NO. 32 (called VB-F8 herein), SEQ ID NO. 33/SEQ ID NO. 34 (called VB-G4 herein), SEQ ID NO. 35/SEQ ID NO. 36 (called VB-G6 herein), SEQ ID NO. 37/SEQ ID NO. 38 (called VB-H4 herein), SEQ ID NO. 39/SEQ ID NO. 40 (called VB-H7 herein), SEQ ID NO. 41/SEQ ID NO. 42 (called VB-H9 herein), SEQ ID NO. 43/SEQ ID NO. 44 (called RV-A9 herein), SEQ ID NO. 45/SEQ ID NO. 46 (called RV-F8 herein), SEQ ID NO. 47/SEQ ID NO. 48 (called RV-H2 herein), SEQ ID NO. 49/SEQ ID NO. 50 (called RV-H4 herein), SEQ ID NO. 51/SEQ ID NO. 52 (called RV-H5 herein), SEQ ID NO. 53/SEQ ID NO. 54 (called C1 herein), SEQ ID NO. 55/SEQ ID NO. 56 (called VR-A2 herein), SEQ ID NO. 57/SEQ ID NO. 58 (called VR-A3 herein), SEQ ID NO. 59/SEQ ID NO. 60 (called VR-A10 herein), SEQ ID NO. 61/SEQ ID NO. 62 (called VR-B2 herein), SEQ ID NO. 63/SEQ ID NO. 64 (called VR-B4 herein), SEQ ID NO. 65/SEQ ID NO. 66 (called VR-B11 herein), SEQ ID NO. 67/SEQ ID NO. 68 (called VR-05 herein), SEQ ID NO. 69/SEQ ID NO. 70 (called VR-C7 herein), SEQ ID NO. 71/SEQ ID NO. 72 (called VR-C11 herein), SEQ ID NO. 73/SEQ ID NO. 74 (called VR-E3 herein), SEQ ID NO. 75/SEQ ID NO. 76 (called VR-G11 herein), SEQ ID NO. 77/SEQ ID NO. 78 (called VK-B8 herein), SEQ ID NO. 79/SEQ ID NO. 80 called VR-H9 herein), SEQ ID NO. 77/SEQ ID NO. 81 (called VK-B8A herein), and combinations thereof.

The present disclosure provides a fully human antibody Fab fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO.

42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, and combinations thereof.

The present disclosure provides a single chain human antibody, having a variable domain region from a heavy chain and a variable domain region from a light chain and a peptide linker connecting the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, and combinations thereof.

The present disclosure further provides a method for treating a broad spectrum of mammalian cancers, comprising administering an effective amount of an anti-VEGFR2 polypeptide, wherein the anti-VEGFR2 polypeptide is selected from the group consisting of a fully human antibody of an IgG class that binds to a VEGFR2 epitope with a binding affinity of at least $10^{-6}$M, a fully human antibody Fab fragment, having a variable domain region from a heavy chain and a variable domain region from a light chain, a single chain human antibody, having a variable domain region from a heavy chain and a variable domain region from a light chain and a peptide linker connecting the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, and combinations thereof;

wherein the fully human antibody Fab fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 77/SEQ ID NO. 81, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2 (called VB-A2 herein), SEQ ID NO. 3/SEQ ID NO. 4 (called VB-A3 herein), SEQ ID NO. 5/SEQ ID NO. 6 (called VB-A7 herein), SEQ ID NO. 7/SEQ ID NO. 8 (called VBV-A7 herein), SEQ ID NO. 9/SEQ ID NO. 10 (called VB-A9 herein), SEQ ID NO. 11/SEQ ID NO. 12 (called VB-A10 herein), SEQ ID NO. 13/SEQ ID NO. 14 (called VB-B6 herein), SEQ ID NO. 15/SEQ ID NO. 16 (called VB-B10 herein), SEQ ID NO. 17/SEQ ID NO. 18 (called VB-D5 herein), SEQ ID NO. 19/SEQ ID NO. 20 (called VB-D6 herein), SEQ ID NO. 21/SEQ ID NO. 22 (called VB-D11 herein), SEQ ID NO. 23/SEQ ID NO. 24 (called VB-E1 herein), SEQ ID NO. 25/SEQ ID NO. 26 (called VB-E2 herein), SEQ ID NO. 27/SEQ ID NO. 28 (called VB-E7 herein), SEQ ID NO. 29/SEQ ID NO. 30 (called VB-F2 herein), SEQ ID NO. 31/SEQ ID NO. 32 (called VB-F8 herein), SEQ ID NO. 33/SEQ ID NO. 34 (called VB-G4 herein), SEQ ID NO. 35/SEQ ID NO. 36 (called VB-G6 herein), SEQ ID NO. 37/SEQ ID NO. 38 (called VB-H4 herein), SEQ ID NO. 39/SEQ ID NO. 40 (called VB-H7 herein), SEQ ID NO. 41/SEQ ID NO. 42 (called VB-H9 herein), SEQ ID NO. 43/SEQ ID NO. 44 (called RV-A9 herein), SEQ ID NO. 45/SEQ ID NO. 46 (called RV-F8 herein), SEQ ID NO. 47/SEQ ID NO. 48 (called RV-H2 herein), SEQ ID NO. 49/SEQ ID NO. 50 (called RV-H4 herein), SEQ ID NO. 51/SEQ ID NO. 52 (called RV-H5 herein), SEQ ID NO. 53/SEQ ID NO. 54 (called C1 herein), SEQ ID NO. 55/SEQ ID NO. 56 (called VR-A2 herein), SEQ ID NO. 57/SEQ ID NO. 58 (called VR-A3 herein), SEQ ID NO. 59/SEQ ID NO. 60 (called VR-A10 herein), SEQ ID NO. 61/SEQ ID NO. 62 (called VR-B2 herein), SEQ ID NO. 63/SEQ ID NO. 64 (called VR-B4 herein), SEQ ID NO. 65/SEQ ID NO. 66 (called VR-B11 herein), SEQ ID NO. 67/SEQ ID NO. 68 (called VR-05 herein), SEQ ID NO. 69/SEQ ID NO. 70 (called VR-C7 herein), SEQ ID NO. 71/SEQ ID NO. 72 (called VR-C11 herein), SEQ ID NO. 73/SEQ ID NO. 74 (called VR-E3 herein), SEQ ID NO. 75/SEQ ID NO. 76 (called VR-G11 herein), SEQ ID NO. 77/SEQ ID NO. 78 (called VK-B8 herein), SEQ ID NO. 79/SEQ ID NO. 80 (called VR-H9 herein), SEQ ID NO. 77/SEQ ID NO. 81 (called VK-B8A herein), and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO.

45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 77/SEQ ID NO. 81, and combinations thereof.

BRIEF DESCRIPTION OF THE FIGURES

FIG. 7B is a zoomed in region of FIG. 7A to examine baseline fluctuations.

DETAILED DESCRIPTION

Figure 1:
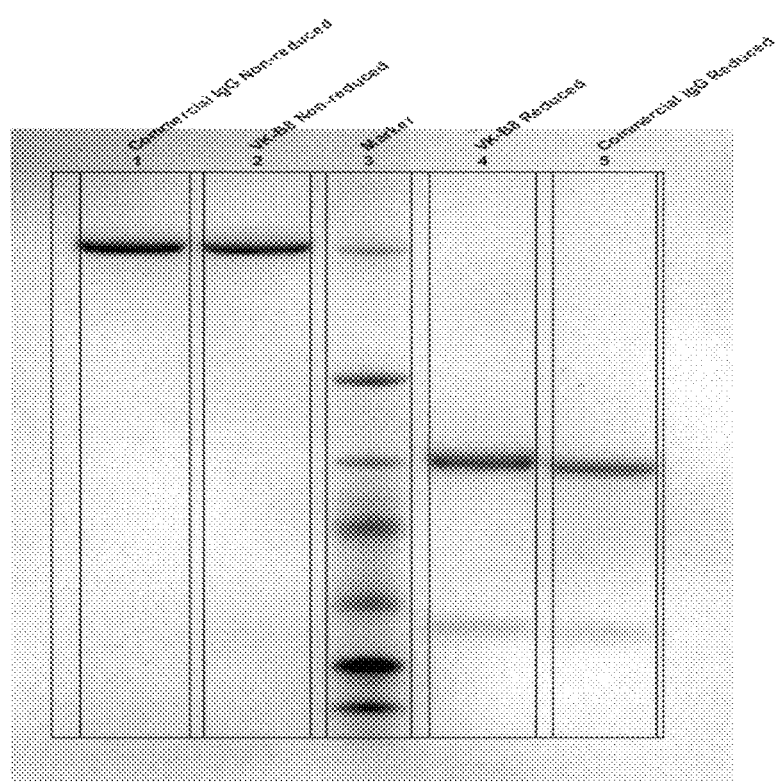
FIG. 1 shows SDS-PAGE analysis of VK-B8, an exemplary anti-VEGFR2 antibody disclosed herein and a commercially available therapeutic monoclonal antibody.
Figure 2:
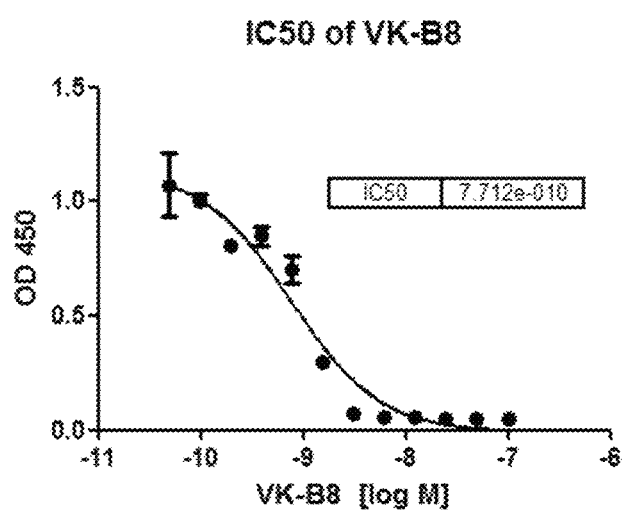
FIG. 2 shows how VK-B8 blocks VEGF binding to soluble VEGFR2-Fc with an $IC_{50}$ of about $7.7 \times 10^{-10}$ M.

The present disclosure provides a fully human antibody of an IgG class that binds to a VEGFR2 epitope with a binding affinity of 100 nM or less, that has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 79/SEQ ID NO. 80, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called VB-A2 herein), SEQ ID NO. 3/SEQ ID NO. 4 (called VB-A3 herein), SEQ ID NO. 5/SEQ ID NO. 6 (called VB-A7 herein), SEQ ID NO. 7/SEQ ID NO. 8 (called VBV-A7 herein), SEQ ID NO. 9/SEQ ID NO. 10 (called VB-A9 herein), SEQ ID NO. 11/SEQ ID NO. 12 (called VB-A10 herein), SEQ ID NO. 13/SEQ ID NO. 14 (called VB-B6 herein), SEQ ID NO. 15/SEQ ID NO. 16 (called VB-B10 herein), SEQ ID NO. 17/SEQ ID NO. 18 (called VB-D5 herein), SEQ ID NO. 19/SEQ ID NO. 20 (called VB-D6 herein), SEQ ID NO. 21/SEQ ID NO. 22 (called VB-D11 herein), SEQ ID NO. 23/SEQ ID NO. 24 (called VB-E1 herein), SEQ ID NO. 25/SEQ ID NO. 26 (called VB-E2 herein), SEQ ID NO. 27/SEQ ID NO. 28 (called VB-E7 herein), SEQ ID NO. 29/SEQ ID NO. 30 (called VB-F2 herein), SEQ ID NO. 31/SEQ ID NO. 32 (called VB-F8 herein), SEQ ID NO. 33/SEQ ID NO. 34 (called VB-G4 herein), SEQ ID NO. 35/SEQ ID NO. 36 (called VB-G6 herein), SEQ ID NO. 37/SEQ ID NO. 38 (called VB-H4 herein), SEQ ID NO. 39/SEQ ID NO. 40

(called VB-H7 herein), SEQ ID NO. 41/SEQ ID NO. 42 (called VB-H9 herein), SEQ ID NO. 43/SEQ ID NO. 44 (called RV-A9 herein), SEQ ID NO. 45/SEQ ID NO. 46 (called RV-F8 herein), SEQ ID NO. 47/SEQ ID NO. 48 (called RV-H2 herein), SEQ ID NO. 49/SEQ ID NO. 50 (called RV-H4 herein), SEQ ID NO. 51/SEQ ID NO. 52 (called RV-H5 herein), SEQ ID NO. 53/SEQ ID NO. 54 (called C1 herein), SEQ ID NO. 55/SEQ ID NO. 56 (called VR-A2 herein), SEQ ID NO. 57/SEQ ID NO. 58 (called VR-A3 herein), SEQ ID NO. 59/SEQ ID NO. 60 (called VR-A10 herein), SEQ ID NO. 61/SEQ ID NO. 62 (called VR-B2 herein), SEQ ID NO. 63/SEQ ID NO. 64 (called VR-B4 herein), SEQ ID NO. 65/SEQ ID NO. 66 (called VR-B11 herein), SEQ ID NO. 67/SEQ ID NO. 68 (called VR-05 herein), SEQ ID NO. 69/SEQ ID NO. 70 (called VR-C7 herein), SEQ ID NO. 71/SEQ ID NO. 72 (called VR-C11 herein), SEQ ID NO. 73/SEQ ID NO. 74 (called VR-E3 herein), SEQ ID NO. 75/SEQ ID NO. 76 (called VR-G11 herein), SEQ ID NO. 77/SEQ ID NO. 78 (called VK-B8 herein), SEQ ID NO. 79/SEQ ID NO. 80 (called VR-H9 herein), SEQ ID NO. 77/SEQ ID NO. 81 (called VK-B8 herein), and combinations thereof.

The present disclosure provides a fully human antibody Fab fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 77/SEQ ID NO. 81, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO.

49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 77/SEQ ID NO. 81, and combinations thereof.

The present disclosure further provides a method for treating a broad spectrum of mammalian cancers, comprising administering an effective amount of an anti-VEGFR2 polypeptide, wherein the anti-VEGFR2 polypeptide is selected from the group consisting of a fully human antibody of an IgG class that binds to a VEGFR2 epitope with a binding affinity of at least $10^{-6}$M, a fully human antibody Fab fragment, having a variable domain region from a heavy chain and a variable domain region from a light chain, a single chain human antibody, having a variable domain region from a heavy chain and a variable domain region from a light chain and a peptide linker connecting the heavy chain and light chain variable domain regions, and combinations thereof;

wherein the fully human antibody has a heavy chain variable domain sequence that is at least 95% identical to the amino acid sequences selected from the group consisting SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, and combinations thereof;

wherein the fully human antibody Fab fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO.

59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 77/SEQ ID NO. 81, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 77/SEQ ID NO. 81, and combinations thereof. Preferably, the fully human single chain antibody has both a heavy chain variable domain region and a light chain variable domain region, wherein the single chain fully human antibody has a heavy chain/light chain variable domain sequence selected from the group consisting SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 77/SEQ ID NO. 81, and combinations thereof.

Preferably, the mammalian cancer to be treated is selected from the group consisting of ovarian, colon, breast or hepatic carcinoma cell lines, myelomas, neuroblastic-derived CNS tumors, monocytic leukemias, B-cell derived leukemias, T-cell derived leukemias, B-cell derived lymphomas, T-cell derived lymphomas, mast cell derived tumors, and combinations thereof.

By "inhibit" is meant a measurable reduction in a phenomenon, often used herein in reference to any of the following: the interaction of VEGF with a VEGFR, VEGF- or VEGFR-mediated angiogenesis, angiogenesis, symptoms of angiogenesis, the viability of VEGFR-containing cells, the viability of VEGF-dependent Ba/F3 cells, or VEGF- or VEGFR-mediated cellular proliferation as compared to a control sample not treated with the polypeptide. A polypeptide will inhibit a VEGF- or VEGFR2 mediated activity if the reduction in activity or interaction is at least 10%, preferably 20%, 30%, 40%, or 50%, and more preferably 60%, 70%, 80%, 90% or more.

By "VEGF biological activity" is meant any function of any VEGF family member acting through any VEGF receptor, but particularly signaling through a VEGFR2 receptor. The VEGF ligand family includes VEGF-A, VEGF-B, VEGF-C, VEGF-D, and placental growth factor (PlGF), as well as various alternatively spliced forms of VEGF including VEGF121, VEGF145, VEGF165, VEGF189, and VEGF206 (Tischer et al., *J. Biol. Chem,* 266:11947-11954, 1991). The VEGFR family of tyrosine kinase receptors includes VEGFR-1 (also known as Flt-1), VEGFR2 (also known as KDR (human form) or Flk-1 (mouse form)), and VEGFR-3 (also known as Flt-4). VEGF ligands bind to the VEGF receptors to induce, for example, angiogenesis, vasculogenesis, endothelial cell proliferation, vasodilation, and cell migration. VEGFR2 is believed to be the VEGFR most involved in angiogenesis. A VEGFR2 or KDR-mediated biological activity is any biological function in which VEGFR2 or KDR participates in significantly, such that antagonism of VEGFR2 or KDR causes a measurable decrease in the biological activity. Methods for measuring angiogenesis are standard, and are described, for example, in Jain et al. (*Nat. Rev. Cancer* 2:266-276, 2002). Angiogenesis can be assayed by measuring the number of non-branching blood vessel segments (number of segments per unit area), the functional vascular density (total length of perfused blood vessel per unit area), the vessel diameter, the formation of vascular channels, or the vessel volume density (total of calculated blood vessel volume based on length and diameter of each segment per unit area). Exemplary assays for VEGF-mediated proliferation and angiogenesis can be found in U.S. Pat. No. 6,559,126, the disclosure of which is incorporated by reference herein, Lyden et al, *Nature Medicine* 7:1194 (2001), Jacob et al, *Exp. Pathol.* 15:1234 (1978) and Bae et al, *J. Biol. Chem.* 275:13588 (2000). These assays can be performed using either purified receptor or ligand or both, and can be performed in vitro or in vivo. These assays can also be performed in cells using a genetically introduced or the naturally-occurring ligand or receptor or both. A polypeptide that inhibits the biological activity of VEGF will cause a decrease of at least 10%, preferably 20%, 30%, 40%, or 50%, and more preferably 60%, 70%, 80%, 90% or greater decrease in the biological activity of VEGF. The inhibition of biological activity can also be measured by the $IC_{50}$. Preferably, a polypeptide that inhibits the biological activity of VEGF or VEGFR2 will have an $IC_{50}$ of less than 100 nM, more preferably less than 10 nM and most preferably less than 1 nM.

Polypeptides of the present invention can be produced using any standard methods. In one example, the polypeptides are produced by recombinant DNA methods by inserting a nucleic acid sequence (e.g., a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA*. 2003 100(2):438-42; Sinclair et al. *Protein Expr. Purif.* 2002 (1):96-105; Connell N D. *Curr. Opin. Biotechnol.* 2001 12(5):446-9; Makrides et al. *Microbiol. Rev.* 1996 60(3):512-38; and Sharp et al. *Yeast*. 1991 7(7):657-78.

General techniques for nucleic acid manipulation are described for example in Sambrook et al., *Molecular Cloning: A Laboratory Manual*, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation.

The recombinant DNA can also include any type of protein tag sequence that may be useful for purifying the protein. Examples of protein tags include but are not limited to a poly-histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (*Bio/Technology*, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

The polypeptide can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See, e.g., Raju et al. *Biochemistry*. 2001 31; 40(30): 8868-76. Effects of such non-amino acid elements on the functionality of a polypeptide may be tested for its antagonizing role of VEGFR2 or VEGF function, e.g., its inhibitory effect on angiogenesis or on tumor growth.

In one specific embodiment, modified forms of the subject soluble polypeptides comprise linking the subject soluble polypeptides to nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. Examples of the modified polypeptide include PEGylated VK-B8.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O$(CH_2CH_2O)_n$-1$CH_2CH_2OH$ (1), where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

A variety of molecular mass forms of PEG can be selected, e.g., from about 1,000 Daltons (Da) to 100,000 Da (n is 20 to 2300), for conjugating to VEGFR2 binding polypeptides. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

In a specific embodiment of the invention, a VEGFR2 binding polypeptide is covalently linked to one poly(ethylene glycol) group of the formula: $-CO-(CH_2)_x-(OCH_2CH_2)_m-OR$, with the $-CO$ (i.e. carbonyl) of the poly(ethylene glycol) group forming an amide bond with one of the amino groups of the binding polypeptide; R being lower alkyl; x being 2 or 3; m being from about 450 to about 950; and n and m being chosen so that the molecular weight of the conjugate minus the binding polypeptide is from about 10 to 40 kDa. In one embodiment, a binding polypeptide's 6-amino group of a lysine is the available (free) amino group.

The above conjugates may be more specifically presented by formula (II): $P-NHCO-(CH_2)_x-(OCH_2CH_2)_m-OR$ (II), wherein P is the group of a binding polypeptide as described herein, (i.e. without the amino group or amino groups which form an amide linkage with the carbonyl shown in formula (II); and wherein R is lower alkyl; x is 2 or 3; m is from about 450 to about 950 and is chosen so that the molecular weight of the conjugate minus the binding polypeptide is from about 10 to about 40 kDa. As used herein, the given ranges of "m" have an orientational meaning. The ranges of "m" are determined in any case, and exactly, by the molecular weight of the PEG group.

In one specific embodiment, carbonate esters of PEG are used to form the PEG-binding polypeptide conjugates. N,N'-disuccinimidylcarbonate (DSC) may be used in the reaction with PEG to form active mixed PEG-succinimidyl carbonate that may be subsequently reacted with a nucleophilic group of a linker or an amino group of a binding polypeptide (see U.S. Pat. Nos. 5,281,698 and 5,932,462). In a similar type of reaction, 1,1'-(dibenzotriazolyl)carbonate and di-(2-pyridyl) carbonate may be reacted with PEG to form PEG-benzotriazolyl and PEG-pyridyl mixed carbonate (U.S. Pat. No. 5,382,657), respectively.

In some embodiments, the pegylated binding polypeptide comprises a PEG molecule covalently attached to the alpha amino group of the N-terminal amino acid. Site specific N-terminal reductive amination is described in Pepinsky et al., (2001) *JPET,* 297, 1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) *J. Biol. Chem.* 254, 12579, and in Chamow et al., (1994) *Bioconjugate Chem.* 5, 133.

In another embodiment, pegylated binding polypeptide comprises one or more PEG molecules covalently attached to a linker, which in turn is attached to the alpha amino group of the amino acid residue at the N-terminus of the binding polypeptide. Such an approach is disclosed in U.S. Patent Publication No. 2002/0044921 and in WO094/01451.

In one embodiment, a binding polypeptide is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., *Bioconjug. Chem.* 2004; 15(5):1005-1009.

The ratio of a binding polypeptide to activated PEG in the conjugation reaction can be from about 1:0.5 to 1:50, between from about 1:1 to 1:30, or from about 1:5 to 1:15. Various aqueous buffers can be used in the present method to catalyze the covalent addition of PEG to the binding polypeptide. In one embodiment, the pH of a buffer used is from about 7.0 to 9.0. In another embodiment, the pH is in a slightly basic range, e.g., from about 7.5 to 8.5. Buffers having a pKa close to neutral pH range may be used, e.g., phosphate buffer.

Conventional separation and purification techniques known in the art can be used to purify PEGylated binding polypeptide, such as size exclusion (e.g. gel filtration) and ion exchange chromatography. Products may also be separated using SDS-PAGE. Products that may be separated include mono-, di-, tri- poly- and un-pegylated binding polypeptide, as well as free PEG. The percentage of mono-PEG conjugates can be controlled by pooling broader fractions around the elution peak to increase the percentage of mono-PEG in the composition. About ninety percent of mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

In one embodiment, PEGylated binding polypeptide of the invention contain one, two or more PEG moieties. In one embodiment, the PEG moiety(ies) are bound to an amino acid residue which is on the surface of the protein and/or away from the surface that contacts the target ligand. In one embodiment, the combined or total molecular mass of PEG in PEG-binding polypeptide is from about 3,000 Da to 60,000 Da, optionally from about 10,000 Da to 36,000 Da. In a one embodiment, the PEG in pegylated binding polypeptide is a substantially linear, straight-chain PEG.

In one embodiment of the invention, the PEG in pegylated binding polypeptide is not hydrolyzed from the pegylated amino acid residue using a hydroxylamine assay, e.g., 450 mM hydroxylamine (pH 6.5) over 8 to 16 hours at room temperature, and is thus stable. In one embodiment, greater than 80% of the composition is stable mono-PEG-binding polypeptide, more preferably at least 90%, and most preferably at least 95%.

In another embodiment, the pegylated binding polypeptides of the invention will preferably retain at least 25%, 50%, 60%, 70% least 80%, 85%, 90%, 95% or 100% of the biological activity associated with the unmodified protein. In one embodiment, biological activity refers to its ability to bind to VEGFR2, as assessed by KD, $k_{on}$ or $k_{off}$. In one specific embodiment, the pegylated binding polypeptide protein shows an increase in binding to VEGFR relative to unpegylated binding polypeptide.

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life (t.sub.½) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half-life, such as the half-life of the protein in the serum or other bodily fluid of an animal.

Therapeutic Formulations and Modes of Administration

The present disclosure features methods for treating conditions or preventing pre-conditions which respond to an inhibition of VEGF biological activity. Preferred examples are conditions that are characterized by inappropriate angiogenesis. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, and most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary.

Exemplary Uses

The VEGFR2 binding proteins described herein and their related variants are useful in a number of therapeutic and diagnostic applications. These include the inhibition of the biological activity of VEGF by competing for or blocking the binding to a VEGFR2.

On the basis of their efficacy as inhibitors of VEGF biological activity, the polypeptides of the invention are effective against a number of conditions associated with inappropriate angiogenesis, including but not limited to autoimmune disorders (e.g., rheumatoid arthritis, inflammatory bowel disease or psoriasis); cardiac disorders (e.g., atherosclerosis or blood vessel restenosis); retinopathies (e.g., proliferative retinopathies generally, diabetic retinopathy, age-related macular degeneration or neovascular glaucoma), renal disease (e.g., diabetic nephropathy, malignant nephrosclerosis, thrombotic microangiopathy syndromes; transplant rejection; inflammatory renal disease; glomerulonephritis; mesangioproliferative glomerulonephritis; haemolytic-uraemic syndrome; and hypertensive nephrosclerosis); hemangioblastoma; hemangiomas; thyroid hyperplasias; tissue transplantations; chronic inflammation; Meigs's syndrome; pericardial effusion; pleural effusion; autoimmune diseases; diabetes; endometriosis; chronic asthma; undesirable fibrosis (particularly hepatic fibrosis) and cancer, as well as complications arising from cancer, such as pleural effusion and ascites. Preferably, the VEGFR2-binding polypeptides of the invention can be used for the treatment or prevention of hyperproliferative diseases or cancer and the metastatic spread of cancers. Non-limiting examples of cancers include bladder, blood, bone, brain, breast, cartilage, colon kidney, liver, lung, lymph node, nervous tissue, ovary, pancreatic, prostate, skeletal muscle, skin, spinal cord, spleen, stomach, testes, thymus, thyroid, trachea, urogenital tract, ureter, urethra, uterus, or vaginal cancer. Additional treatable conditions can be found in U.S. Pat. No. 6,524,583, incorporated by reference herein. Other references describing uses for VEGFR2 binding polypeptides include: McLeod et al., *Invest. Ophthalmol. Vis. Sci.* 2002; 43(2):474-82; Watanabe et al., *Exp. Dermatol.* 2004; 13(11):671-81; Yoshiji et al., *Gut.* 2003 52(9):1347-54; Verheul et al., *Oncologist.* 2000; 5 Suppl 1:45-50; and Boldicke et al., *Stem Cells.* 2001 19(1):24-36.

As described herein, angiogenesis-associated diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; inflammatory disorders such as immune and non-immune inflammation; chronic articular rheumatism and psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation and wound healing; telangiectasia psoriasis scleroderma, pyogenic granuloma, coronary collaterals, ischemic limb angiogenesis, corneal diseases, rubeosis, arthritis, diabetic neovascularization, fractures, vasculogenesis, hematopoiesis.

A VEGFR2 binding polypeptide can be administered alone or in combination with one or more additional therapies such as chemotherapy, radiotherapy, immunotherapy, surgical intervention, or any combination of these. Long-term therapy is equally possible as is adjuvant therapy in the context of other treatment strategies, as described above.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject anti-VEGFR2 antibodies agents of the invention can be used alone. Alternatively, the subject agents may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds has been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a polypeptide therapeutic agent of the present invention is administered in combination with another conventional anti-neoplastic agent, either concomitantly or sequentially, such therapeutic agent may be found to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

Certain chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (e.g., VEGF inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In certain embodiments, pharmaceutical compounds that may be used for combinatory anti-angiogenesis therapy include: (1) inhibitors of release of "angiogenic molecules," such as bFGF (basic fibroblast growth factor); (2) neutralizers of angiogenic molecules, such as an anti-βFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like. For additional proposed inhibitors of angiogenesis, see Blood et al., *Bioch. Biophys. Acta.* 1032:89-118 (1990), Moses et al., *Science,* 248:1408-1410 (1990), Ingber et al., *Lab. Invest.,* 59:44-51 (1988), and U.S. Pat. Nos. 5,092,885; 5,112,946; 5,192,744; 5,202,352; and 6,573,256. In addition, there are a wide variety of compounds that can be used to inhibit angiogenesis, for example, endostatin protein or derivatives, lysine binding fragments of angiostatin, melanin or melanin-promoting compounds, plasminogen fragments (e.g., Kringles 1-3 of plasminogen), tropoin subunits, antagonists of vitronectin $\alpha_v\beta$, peptides derived from Saposin B, antibiotics or analogs (e.g., tetracycline, or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718; 6,462,075; 6,465,431; 6,475,784; 6,482,802; 6,482,810; 6,500,431; 6,500,924; 6,518,298; 6,521,439; 6,525,019; 6,538,103; 6,544,758; 6,544,947; 6,548,477; 6,559,126; and 6,569,845).

Depending on the nature of the combinatory therapy, administration of the polypeptide therapeutic agents may be continued while the other therapy is being administered and/or thereafter. Administration of the polypeptide therapeutic agents may be made in a single dose, or in multiple doses. In some instances, administration of the polypeptide therapeutic agents is commenced at least several days prior to the conventional therapy, while in other instances, administration is begun either immediately before or at the time of the administration of the conventional therapy.

The VEGFR2 binding proteins described herein can also be detectably labeled and used to contact cells expressing VEGFR2 for imaging applications or diagnostic applications. For diagnostic purposes, the polypeptide of the invention is preferably immobilized on a solid support. Preferred solid supports include columns (for example, affinity columns, such as agarose-based affinity columns), microchips, or beads.

In one example of a diagnostic application, a biological sample, such as serum or a tissue biopsy, from a patient suspected of having a condition characterized by inappropriate angiogenesis is contacted with a detectably labeled polypeptide of the invention to detect levels of VEGFR2. The levels of VEGFR2 detected are then compared to levels of VEGFR2 detected in a normal sample also contacted with the labeled polypeptide. An increase of at least 10%, 20%, 30%, 40%, 50%, 60%, 70%, 80%, or 90% in the levels of the VEGFR2 may be considered a diagnostic indicator of a condition characterized by inappropriate angiogenesis.

In certain embodiments, the VEGFR2 binding polypeptides of the invention are further attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radio scintigraphy, nuclear magnetic resonance imaging, computed tomography or positron emission tomography. Immunoscintigraphy using VEGFR2 binding polypeptides directed at VEGFR2 may be used to detect and/or diagnose cancers and vasculature. For example, any of the binding polypeptide against the VEGFR2 marker labeled with $^{99}$Technetium, $^{111}$Indium, or $^{125}$Iodine may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically a person skilled in the art administers 0.1-100 millicuries per dose of imaging agent, preferably 1-10 millicuries, most often 2-5 millicuries. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

The VEGFR2 binding polypeptides can also be used to deliver additional therapeutic agents (including but not limited to drug compounds, chemotherapeutic compounds, and radiotherapeutic compounds) to a cell or tissue expressing VEGFR2. In one example, the VEGFR2 binding polypeptide is fused to a chemotherapeutic agent for targeted delivery of the chemotherapeutic agent to a tumor cell or tissue expressing VEGFR2.

The VEGFR2 binding polypeptides are useful in a variety of applications, including research, diagnostic and therapeutic applications. For instance, they can be used to isolate and/or purify receptor or portions thereof, and to study receptor structure (e.g., conformation) and function.

In certain aspects, the various binding polypeptides can be used to detect or measure the expression of VEGFR2, for example, on endothelial cells (e.g., venous endothelial cells), or on cells transfected with a VEGFR2 gene. Thus, they also have utility in applications such as cell sorting and imaging (e.g., flow cytometry, and fluorescence activated cell sorting), for diagnostic or research purposes.

In certain embodiments, the binding polypeptides of fragments thereof can be labeled or unlabeled for diagnostic purposes. Typically, diagnostic assays entail detecting the formation of a complex resulting from the binding of a binding polypeptide to VEGFR2. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising a VEGFR2 protein is combined with the subject binding polypeptides, binding occurs between the binding polypeptides and the VEGFR2 protein. In one embodiment, a sample containing cells expressing a VEGFR2 protein (e.g., endothelial cells) is combined with the subject antibodies, and binding occurs between the binding polypeptides and cells bearing a VEGFR2 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of a VEGFR2 protein in a biological sample can also be prepared. Such kits will include a VEGFR2 binding polypeptide which binds to a VEGFR2 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Similarly, the present disclosure also provides a method of detecting and/or quantitating expression of VEGFR2, wherein a composition comprising a cell or fraction thereof (e.g., membrane fraction) is contacted with a binding polypeptide which binds to a VEGFR2 or portion of the receptor under conditions appropriate for binding thereto, and the binding is monitored. Detection of the binding polypeptide, indicative of the formation of a complex between binding polypeptide and VEGFR2 or a portion thereof, indicates the presence of the receptor. Binding of a polypeptide to the cell can be determined by standard methods, such as those described in the working examples. The method can be used to detect expression of VEGFR2 on cells from an individual. Optionally, a quantitative expression of VEGFR2 on the surface of endothelial cells can be evaluated, for instance, by flow cytometry, and the staining intensity can be correlated with disease susceptibility, progression or risk.

The present disclosure also provides a method of detecting the susceptibility of a mammal to certain diseases. To illustrate, the method can be used to detect the susceptibility of a mammal to diseases which progress based on the amount of VEGFR2 present on cells and/or the number of VEGFR2-positive cells in a mammal. In one embodiment, the invention relates to a method of detecting susceptibility of a mammal to a tumor. In this embodiment, a sample to be tested is contacted with a binding polypeptide which binds to a VEGFR2 or portion thereof under conditions appropriate for binding thereto, wherein the sample comprises cells which express VEGFR2 in normal individuals. The binding and/or amount of binding is detected, which indicates the susceptibility of the individual to a tumor, wherein higher levels of receptor correlate with increased susceptibility of the individual to a tumor.

The following terms, unless otherwise indicated, shall be understood to have the following meanings:

The terms "VEGFR2 inhibitor" and "VEGFR2 antagonist" are used interchangeably. Each is a molecule that detectably inhibits at least one function of VEGFR2. Conversely, a "VEGFR2 agonist" is a molecule that detectably increases at least one function of VEGFR2. The inhibition caused by a VEGFR2 inhibitor need not be complete so long as it is detectable using an assay. Any assay of a function of VEGFR2 can be used, examples of which are provided herein. Examples of functions of VEGFR2 that can be inhibited by a VEGFR2 inhibitor, or increased by a VEGFR2 agonist, include cancer cell growth or apoptosis (programmed cell death), and so on. Examples of types of VEGFR2 inhibitors and VEGFR2 agonists include, but are not limited to, VEGFR2 binding polypeptides such as antigen binding proteins (e.g., VEGFR2 inhibiting antigen binding proteins), antibodies, antibody fragments, and antibody derivatives.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronectin components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Preferably, the anti-VEGFR2 antibodies disclosed herein are characterized by their variable domain region sequences in the heavy $V_H$ and light $V_L$ amino acid sequences. The preferred antibody is VK-B8, which is a kappa IgG antibody. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5.sup.th Ed., US Dept. of Health and Human Services, PHS, NIH, NIH Publication no. 91-3242, 1991. Other numbering systems for the amino acids in immunoglobulin chains include IMGT® (International ImMunoGeneTics information system; Lefranc et al., *Dev. Comp. Immunol.* 29:185-203; 2005) and AHo (Honegger and Pluckthun, *J. Mol. Biol.* 309(3):657-670; 2001).

An "antibody" refers to an intact immunoglobulin or to an antigen binding portion (Fab) thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634 and 6,696,245, the disclosures of which are incorporated by reference herein).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (Bird et al., 1988, *Science* 242:423-26 and Huston et al., 1988, *Proc. Natl. Acad. Sci. USA* 85:5879-83).

Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified (Sequences of Proteins of Immunological Interest, 5.sup.th Ed., US Dept. of Health and Human Services, PHS, NIH, NIH Publication no. 91-3242, 1991). Other numbering systems for the amino acids in immunoglobulin chains include IMGT® (International ImMunoGeneTics information system; Lefranc et al., *Dev. Comp. Immunol.* 29:185-203; 2005) and AHo (Honegger and Pluckthun, *J. Mol. Biol.* 309(3):657-670; 2001). One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently.

The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have each and every variable and constant regions derived from human immunoglobulin sequences. In one embodiment, fully human antibody, all of the variable and constant domains are derived from human immunoglobulin sequences (a fully human antibody).

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immuno specific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297; 5,886,152; and 5,877,293.

The term "chimeric antibody" refers to an antibody that contains one or more regions from one antibody and one or more regions from one or more other antibodies.

Further, the framework regions may be derived from one of the same anti-VEGFR2 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (U.S. Pat. No. 4,816,567)

A "neutralizing antibody" or an "inhibitory antibody" is an antibody that inhibits the activation of VEGFR2 when an excess of the anti-VEGFR2 antibody reduces the amount of activation or inhibition by at least about 20% using an assay such as those described herein in the Examples. In various embodiments, the antigen binding protein reduces the amount of amount of activation of VEGFR2 by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human VEGFR2) if it binds to the antigen with a dissociation constant of 1 nM or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

A "host cell" is a cell that can be used to express a nucleic acid. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (Rasmussen et al., 1998, *Cytotechnology* 28:31) or CHO strain DX-B11, which is deficient in DHFR (Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (McMahan et al., 1991, *EMBO J.* 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen Binding Proteins

Antigen binding proteins (e.g., antibodies, antibody fragments, antibody derivatives, antibody muteins, and antibody variants) are polypeptides that bind to VEGFR2, (preferably, human VEGFR2). Antigen binding proteins include antigen binding proteins that inhibit a biological activity of VEGFR2.

Oligomers that contain one or more antigen binding proteins may be employed as VEGFR2 antagonists. Oligomers may be in the form of covalently-linked or non-covalently-linked dimers, trimers, or higher oligomers. Oligomers comprising two or more antigen binding proteins are contemplated for use, with one example being a homodimer. Other oligomers include One embodiment is directed to a dimer comprising two fusion proteins created by fusing a VEGFR2 binding fragment of an anti-VEGFR2 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-VEGFR2 antibody fragment or derivative fused to a leucine zipper peptide are expressed in suitable host cells, and the soluble oligomeric anti-VEGFR2 antibody fragments or derivatives that form are recovered from the culture supernatant.

The present disclosure provides a VEGFR2 antigen binding protein (for example, an anti-VEGFR2 antibody), that has one or more of the following characteristics: binds to both human and murine VEGFR2, inhibits the activation of human VEGFR2, inhibits the activation of murine VEGFR2, and binds to or near the ligand binding domain of VEGFR2.

Antigen-binding fragments of antigen binding proteins of the invention may be produced by conventional techniques. Examples of such fragments include, but are not limited to, Fab and F(ab')$_2$ fragments.

The present disclosure provides monoclonal antibodies that bind to VEGFR2. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen binding proteins directed against VEGFR2 can be used, for example, in assays to detect the presence of VEGFR2 polypeptides, either in vitro or in vivo. The antigen binding proteins also may be employed in purifying VEGFR2 proteins by immunoaffinity chromatography. Those antigen binding proteins that additionally can block ligand binding-mediated activation of VEGFR2 may be used to inhibit a biological activity that results from such binding. Blocking antigen binding proteins can be used in the methods disclosed herein. Such antigen binding proteins that function as VEGFR2 antagonists may be employed in treating any VEGFR2-induced condition, including but not limited to various cancers.

Antigen binding proteins may be employed in an in vitro procedure, or administered in vivo to inhibit a VEGFR2-induced biological activity. Disorders caused or exacerbated (directly or indirectly) by the activation of VEGFR2, examples of which are provided herein, thus may be treated. In one embodiment, the present invention provides a therapeutic method comprising in vivo administration of a VEGFR2 blocking antigen binding protein to a mammal in need thereof in an amount effective for reducing a VEGFR2-induced biological activity.

Antigen binding proteins include fully human monoclonal antibodies that inhibit a biological activity of VEGFR2, such as angiogenesis.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, *EMBO J.* 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of VEGFR2 bound thereto. Polypeptides contemplated for use herein include substantially homogeneous recombinant mammalian anti-VEGFR2 antibody polypeptides substantially free of contaminating endogenous materials.

Antigen binding proteins may be prepared, and screened for desired properties, by any of a number of known techniques. Certain techniques involve isolating a nucleic acid encoding a polypeptide chain (or portion thereof) of an antigen binding protein of interest (e.g., an anti-VEGFR2 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol. Biol.* 178:379-87.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, *Methods Mol. Biol.* 178:303-16). Moreover, if an IgG4 is desired, it may also be desired to introduce a point mutation (CPSCP->CPPCP) in the hinge region (Bloom et al., 1997, *Protein Science* 6:407) to alleviate a tendency to form intra-H chain disulfide bonds that can lead to heterogeneity in the IgG4 antibodies.

In particular embodiments, antigen binding proteins of the present invention have a binding affinity ($K_a$) for VEGFR2 of at least $10^6$ nM. In other embodiments, the antigen binding proteins exhibit a $K_a$ of at least $10^7$, at least $10^8$, at least $10^9$, or at least $10^{10}$ M. In another embodiment, the antigen binding protein exhibits a $K_a$ substantially the same as that of an antibody described herein in the Examples.

In another embodiment, the present disclosure provides an antigen binding protein that has a low dissociation rate from VEGFR2. In one embodiment, the antigen binding protein has a $K_{off}$ of $1\times10^{-4}$ to $1\times10^{-1}$ M or lower. In another embodiment, the $K_{off}$ is $5\times10^{-5}$ to $5\times10^{-1}$ M or lower. In another embodiment, the $K_{off}$ is substantially the same as an antibody described herein in the Examples. In another embodiment, the antigen binding protein binds to VEGFR2 with substantially the same $K_{off}$ as an antibody described herein in the Examples.

In another aspect, the present disclosure provides a VEGFR2 membrane binding protein. In one embodiment, the antigen binding protein has an $IC_{50}$ of 1000 nM or lower. In another embodiment, the $IC_{50}$ is 100 nM or lower; in another embodiment, the $IC_{50}$ is 10 nM or lower. In another embodiment, the $IC_{50}$ is substantially the same as that of an antibody described herein in the Examples. In another embodiment, the antigen binding protein inhibits an activity of VEGFR2 with substantially the same $IC_{50}$ as an antibody described herein in the Examples.

In another aspect, the present disclosure provides an antigen binding protein that binds to human VEGFR2 expressed on the surface of a cell and, when so bound, inhibits VEGFR2 signaling activity in the cell. Any method for determining or estimating the amount of VEGFR2 on the surface and/or in the interior of the cell can be used. In other embodiments, binding of the antigen binding protein to the VEGFR2-expressing cell causes less than about 75%, 50%, 40%, 30%, 20%, 15%, 10%, 5%, 1%, or 0.1% of the cell-surface VEGFR2 to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO00/09560, incorporated by reference herein.

The present disclosure further provides multi-specific antigen binding proteins, for example, bispecific antigen binding protein, e.g., antigen binding protein that binds to two different epitopes of VEGFR2, or to an epitope of VEGFR2 and an epitope of another molecule, via two different antigen binding sites or regions. Moreover, bispecific antigen binding protein as disclosed herein can comprise a VEGFR2 binding site from one of the herein-described antibodies and a second VEGFR2 binding region from another of the herein-described antibodies, including those described herein by reference to other publications. Alternatively, a bispecific antigen binding protein may comprise an antigen binding site from one of the herein described antibodies and a second antigen binding site from another VEGFR2 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule), a detectable bead (such as a magnetic or electrodense (e.g., gold bead), a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

EXAMPLE 1

This example illustrates production runs and how to make anti-VEGFR2 antibody VK-B8. The expression cassette coding for the heavy chain and dihydrofolate reductase (DHFR) was driven by the CMV major immediate early promoter. The expression cassette coding for the light chain and neomycin phosphotransferase was driven by the CMV major immediate early promoter. Transfected cells were cultured in CD OptiCHO medium (Life Technologies) without nucleosides prior to Fluorescence-Activated Cell Sorting (FACS). Cells were "sorted" once using FACS to enrich for high producers. After FACS enrichment, the cell pool was cultured and passaged until the cell viability was greater than 90%. For production of VK-B8, cells were scaled to a desirable density and volume at 37° C. and then placed at 28° C. for the duration of the production run.

VK-B8 was produced in Chinese hamster ovary (CHO) cells stably transfected with expression vectors containing the human VK-B8 mAb IgG1 heavy and kappa light chain structural genes. The host cell line used for the construction of the cell line was a Chinese hamster ovary dihydrofolate reductase (dhfr)-deficient host cell line, CHO-DG44 (Life Technologies). The cell line was maintained in shake flasks and routinely passaged every 3 to 4 days using DG44 (Life Technologies) medium and supplemented with PLURONIC F-68 (Life Technologies) and GlutaMAX I-CTS (Life Technologies). Two plasmids were used to generate the stable pool; the heavy chain and light chain expression vectors pIRES.VEGFR2.VKB8.HC and pIRES.VEGFR2.VKB8.LC, respectively. The plasmid coding for the heavy chain also coded for dhfr as a second cistron which was used as a selectable and amplifiable marker. The plasmid coding for the light chain also contains neomycin phosphotransferase as a second cistron which was used as a selectable marker. The vectors were co-transfected into the host cell line using the cationic lipid Freestyle Max and selected for DHFR and neomycin phosphotransferase expression.

EXAMPLE 2

This example illustrates a differential scanning calorimetry study measuring thermodynamic stability of the anti-VEGFR2 monoclonal antibody VK-B8, compared with Bevacizumab (Avastin®), using MicroCal™ DSC (GE Healthcare). A thermogram for each antibody (0.48-0.55 mg/mL) was obtained in PBS buffer, pH 7.4 from 25° C. to 85° C., using a scan rate of 1° C. per minute, unless otherwise mentioned. The VK-B8 melting temperature profile was monitored in PBS buffer at both pH 7.4 and 6.

| IgG | Melting Temperature in ° C. |
|---|---|
| Avastin | 71.23 |
| VK-B8 | 74.78 |

An Analytical Size-Exclusion Chromatography (ANSEC) (Water's Breeze-HPLC) analysis of the monoclonal antibodies VK-B8 and Bevacizumab (Avastin®) was performed in PBS buffer, pH 6.8 at 0.5 mL/min flow rate using TSKgel Supper SW3000 column (TOSOH Biosciences). Aggregate formation of VK-B8 in PBS buffer at 4° C. was monitored for 4 months using the same system. IgG samples were compared with the BIO-RAD gel filtration protein standard (Cat #, 151-1901: Thyroglobi=670 KDa; Gamma-globulin=158 KDa; Ovalbumin=44 KDa; Myoglobin=17 KDa; Vitamin B12=1.35 KDa). The results are shown in FIG. 7, which provide overlaid ANSEC chromatograms (Ultra Violet trace at 280 nm) of VK-B8 and Bevacizumab (Avastin) in PBS buffer at pH 6.8; STD/standard run (grey dotted line), VK-B8 spectrum (red), Bevacizumab (Avastin) spectrum (green).

Figure 7A:
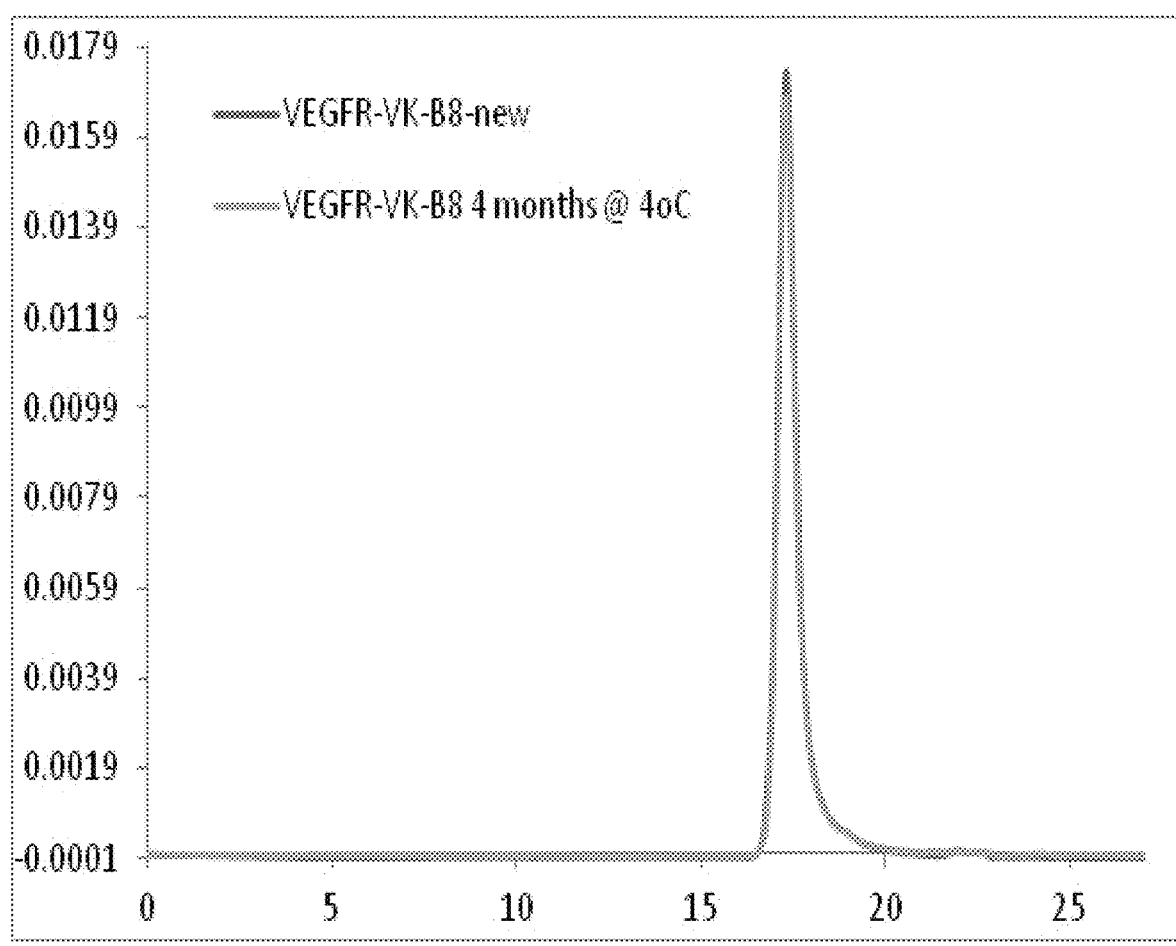
FIG. 7A and FIG. 7B show overlaid ANSEC chromatograms (Ultra Violet trace at 280nm) of VK-B8 in PBS buffer at pH 6.8 immediately after purification and after 4 months at 4° C.:VK-B8 immediately after purification spectrum (blue), VK-B8 after 4 months at 4° C. spectrum (green).
Figure 7B:
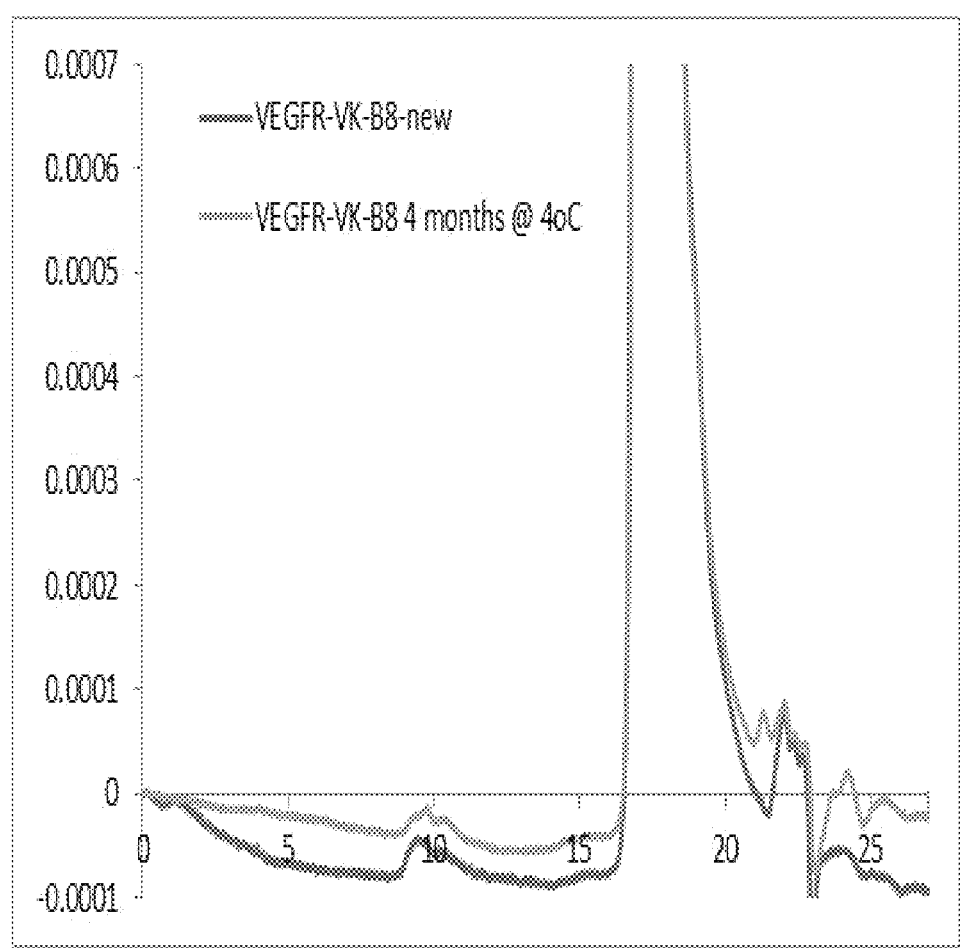

ANSEC analysis of the VK-B8 IgG sample at 4° C. after 0 days and 4 months is shown in FIGS. 7A and 7B which show overlaid ANSEC analysis (Ultra Violet trace at 280 nm0 days (blue) and 4 months (green)) A: representative full spectra, B: Enlarged version of A indicating that VK-B8 remained intact after 4 months.

Further, a Biacore analysis of four antibodies was done for binding.

Biacore analysis of several VEGFR-2 antibodies, including VK-B8

| mAb | ka (1/Ms) | kd (1/s) | Kd (M) |
|---|---|---|---|
| RV-H5 | 2.76E+06 | 2.25E−03 | 8.15E−10 |
| VB-A3 | 3.88E+06 | 1.20E−02 | 3.09E−09 |
| VB-A9 | 1.64E+05 | 4.96E−04 | 3.02E−09 |
| VK-B8 | 7.24E+05 | 8.73E−05 | 1.21E−10 |

EXAMPLE 3

Figure 8:
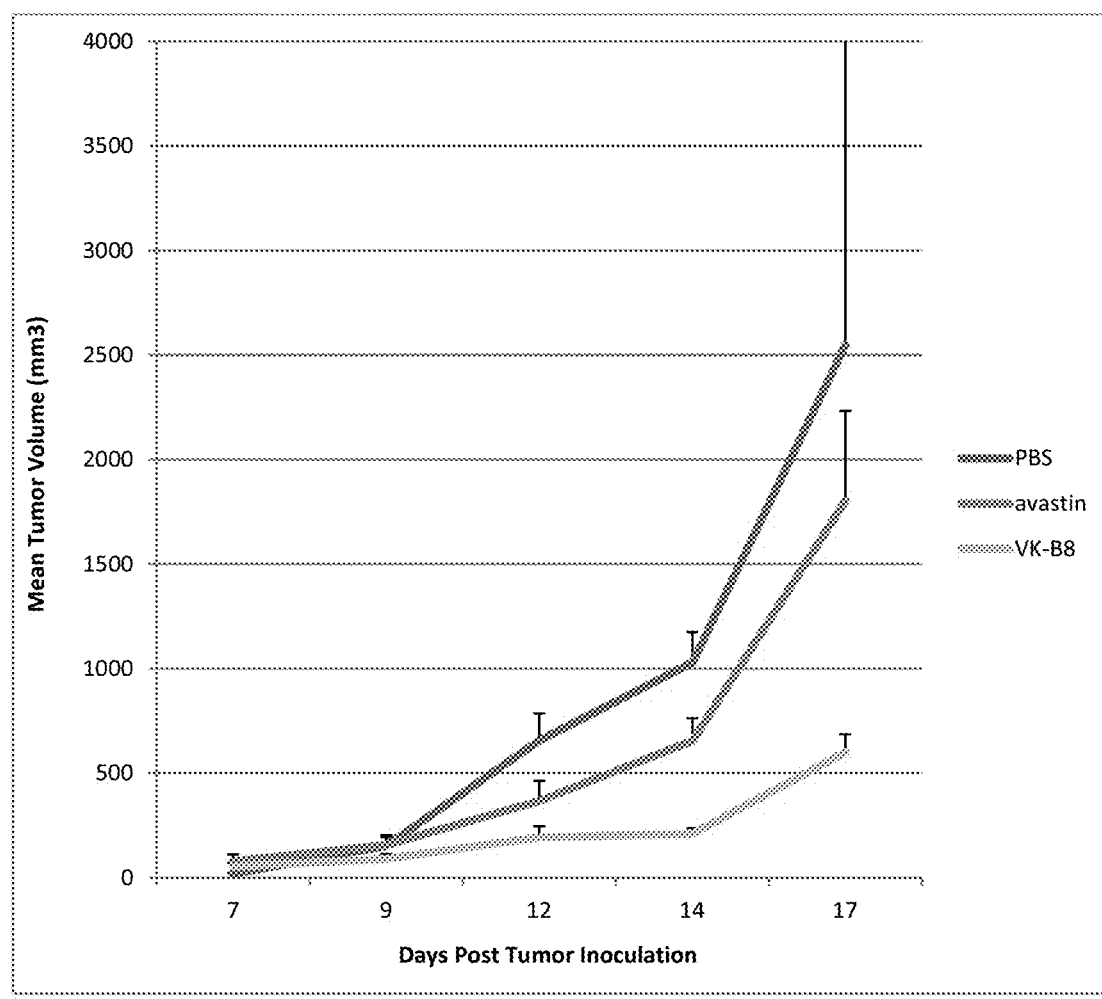
FIG. 8 shows an effect of two antibodies on MC38 colon tumor growth. VK-B8 was compared to Bevacizumab (Avastin®) a marketed anti-VEGF-A (ligand) antibody. VK-B8 shows superior efficacy to Bevacizumab (Avastin) in this in vivo model.

This example illustrates in vivo data comparing a marketed anti-VEGF (ligand) humanized monoclonal antibody (Bevacizumab (Avastin®)) to VK-B8, a disclosed herein fully human anti-VEGFR2 (receptor) antibody, for effects on MC38 colon cancer growth measured by solid tumor volume. C57BL6/6 mice were injected subcutaneously with $2 \times 10^6$ MC38 colon tumor cells. After 4 days, a treatment protocol was initiated. Test antibody was administered at 0.2 mg/mouse ip 3× per week in a volume of 0.1 ml. The tumor volume was measured as W×L×L/2 wherein W is tumor width and L is tumor length. FIG. 8 shows that the disclosed antibody VK-B8 displays greater efficacy than the marketed antibody Bevacizumab (Avastin®; anti-VEGF ligand humanized antibody).

EXAMPLE 4

Figure 9:
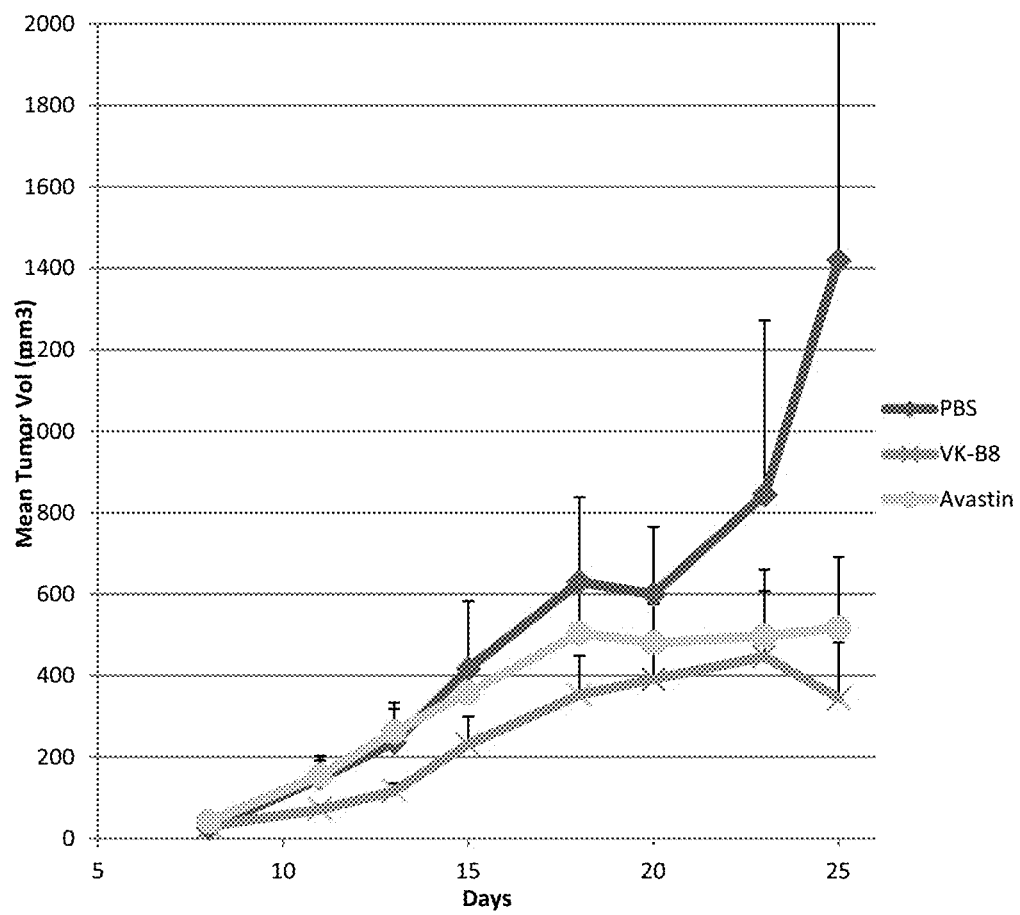
FIG. 9 shows an effect of two antibodies on A431 epidermoid carcinoma cell growth. VK-B8 was compared to Bevacizumab (Avastin) a marketed anti-VEGF-A (ligand) antibody. VK-B8 shows superior efficacy to Bevacizumab (Avastin®) in this in vivo model.

This example illustrates in vivo data comparing a marketed anti-VEGF (ligand) humanized monoclonal antibody (Bevacizumab (Avastin®)) to VK-B8, a disclosed herein fully human anti-VEGFR2 (receptor) antibody, for effects on A431 epidermoid carcinoma cell growth measured by solid tumor volume. Nude mice were injected subcutaneously with $2 \times 10^6$ A431 epidermoid carcinoma cells. After 4 days, a treatment protocol was initiated. Test antibody was administered at 0.2 mg/mouse ip 3× per week in a volume of 0.1 nil. The tumor volume was measured as W×L×L/2 wherein W is tumor width and L is tumor length. FIG. 9 shows that the disclosed antibody, VK-B8, shows similar efficacy compared to the marketed antibody Bevacizumab (Avastin®; anti-VEGF ligand humanized antibody).

EXAMPLE 5

Figure 10:
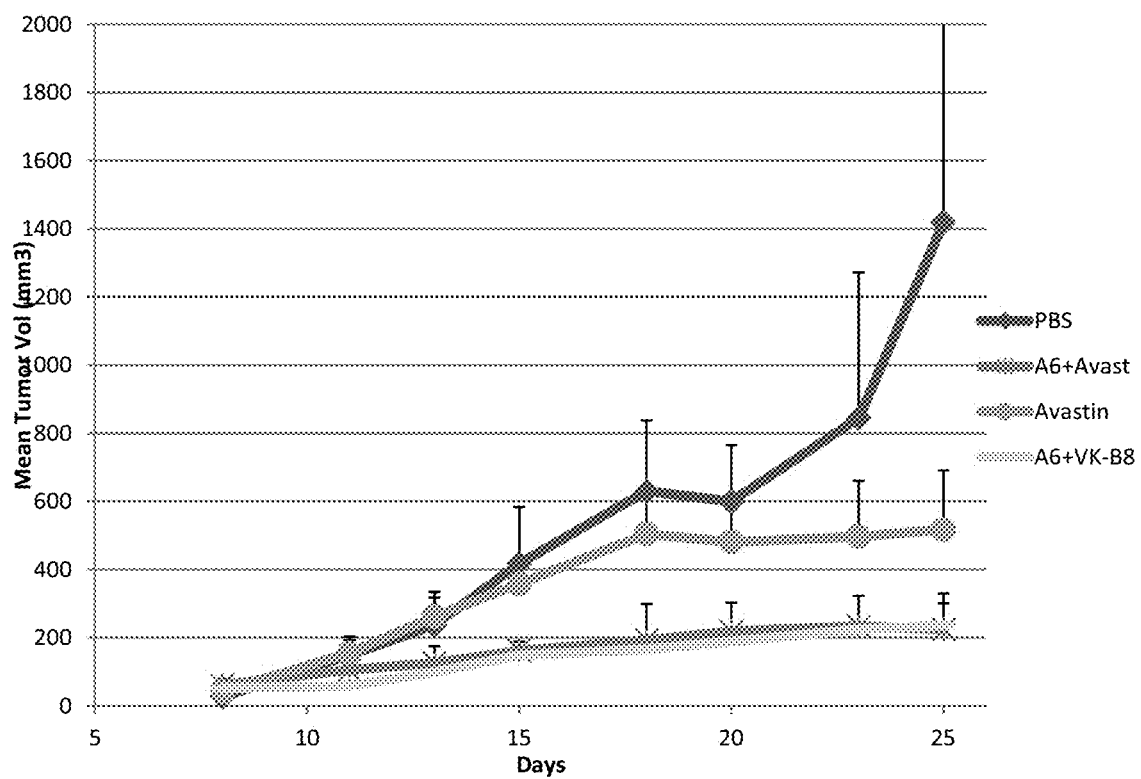
FIG. 10 shows the synergistic combination of an anti-VEGFR2 antibody when administered with an anti-EGFR antibody (Erbitux®, a humanized anti-EGFR antibody or A6, a fully human anti-EGFR antibody) inhibiting tumor cell growth in vivo.

This example illustrates in vivo data comparing a marketed anti-VEGF (ligand) humanized monoclonal antibody (Bevacizumab (Avastin®)) to (1) Erbitux® (cetuximab), a humanized anti-EGFR antibody, (2) A6, a fully human anti-EGFR antibody, (3) combination of A6 plus Bevacizumab (Avastin®), (4) combination of A6 plus Erbitux, and (5) A6 plus VK-B8 wherein VK-B8 is a disclosed herein fully human anti-VEGFR2 (receptor) antibody for effects on A431 epidermoid carcinoma cell growth by measuring solid tumor volume. Nude mice were injected subcutaneously with $2 \times 10^6$ A431 epidermoid carcinoma cells. After 4 days, a treatment protocol was initiated. Test antibody was administered at 0.2 mg/mouse ip 3× per week in a volume of 0.1 nil. The tumor volume was measured as W×L×L/2 wherein W is tumor width and L is tumor length. FIG. 10 shows similar efficacy for each of the treatment groups with the combination of A6+Avastin® and A6+VK-B8 showing the highest efficacy for tumor growth inhibition.

EXAMPLE 6

This example illustrates in vitro data for VK-B8 cellular $EC_{50}$ measurements. Protocol: 50,000 HUVECs were aliquoted into the wells of a 96-well, v-bottom plate in 100 ul FACS Buffer (PBS+2% FBS). A twelve point, 3× dilution curve of VK-B8 was made in FACS Buffer starting at 50 µg/ml ($3.33 \times 10^{-7}$ M). Cells were spun down, washed 1× with FACS Buffer, and then resuspended in 25 µl of antibody solution in triplicate. After 0.5 hr. incubation, cells were washed 1× with FACS Buffer and resuspended in 50 µl PE-conjugated, goat anti-human IgG (γ-chain specific) secondary antibody (Southern Biotech Cat #2040-09). Cells were further incubated for 0.5 hr. and then washed 1× with FACS Buffer. Cells were resuspended in 25 µl FACS Buffer and the median fluorescence intensity in the FL2-H channel was determined using the Intellicyt HTFC flow cytometer.

Figure 4:
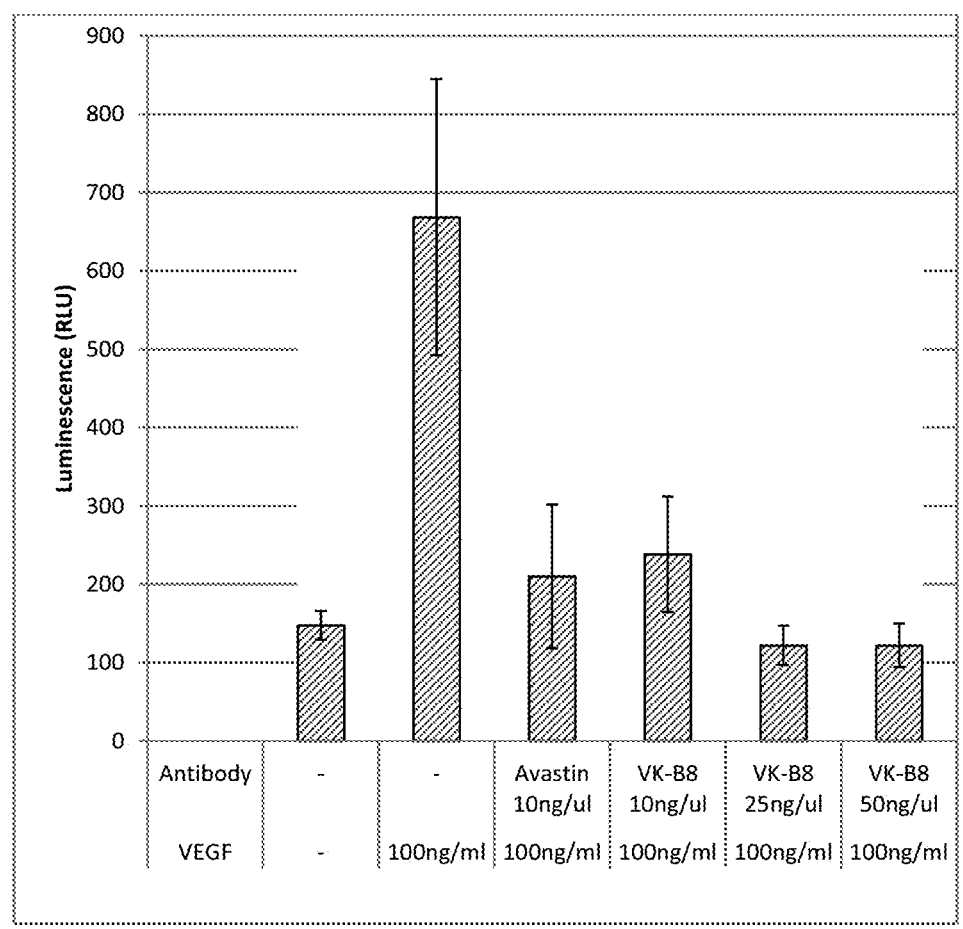
FIG. 4 shows VEGF-mediated HUVEC proliferation at 100 mg/ml VEGF. VK-B8 was compared to Bevacizumab (Avastin®) a marketed anti-VEGF-A (ligand) antibody. VK-B8 shows comparable efficacy to Bevacizumab (Avastin®) in this in vitro model.
Figure 5:
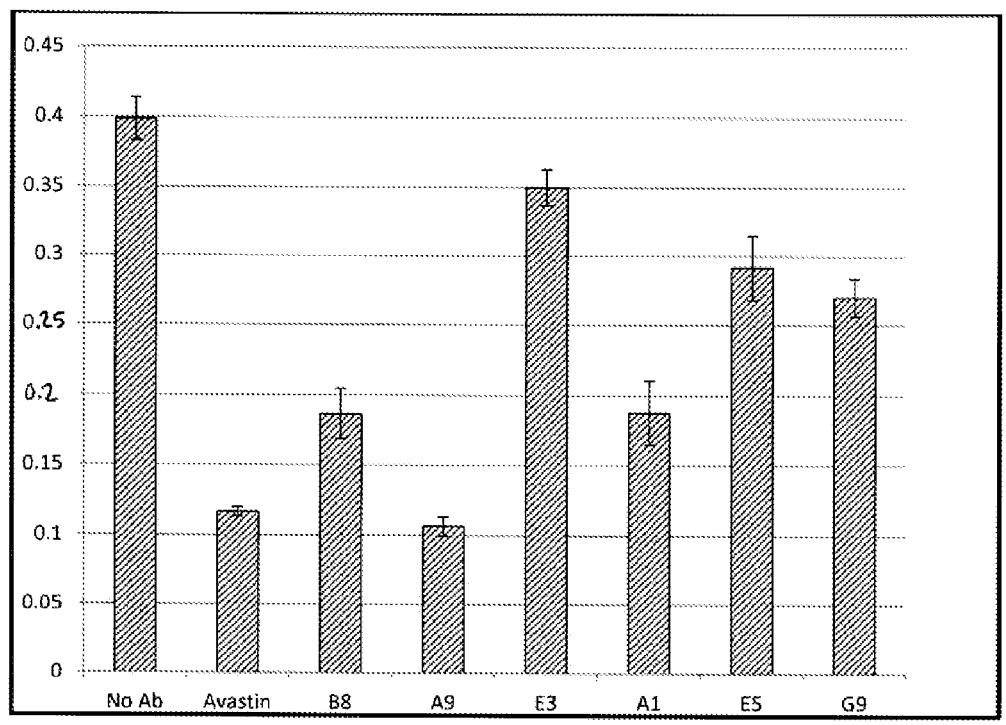
FIG. 5 shows VEGF-stimulated autophosphorylation at 100 ng/ml VEGF of the VEFGR2 receptor in HUVECs. Various anti-VEGFR2 antibodies were compared at an antibody concentration of 10 μg/ml. VK-B8 is the third column from the left.

Results: The cell binding $EC_{50}$ for VK-B8 on HUVECs was determined to be 1.3 nM. Data was analyzed and plotted in Graph Pad Prizm using non-linear regression fit. Data points are shown (FIG. 4) as the median fluorescence intensity (MFI) of positively labeled cells +/− Std Error.

EXAMPLE 7

This example illustrates in vitro data for cell binding as part of an initial screen for several disclosed antibodies, including VK-B8. Protocol: 100,000 HUVECs were aliquoted into tubes in 100 µl FACS Buffer (PBS+2% FBS). Cells were spun down and then resuspended in 100 µl of FACS Buffer plus 10 µg/ml of the indicated antibody in triplicate. After 0.5 hr incubation, cells were washed 1× with FACS Buffer and resuspended in 100 µl PE-conjugated, goat anti-human IgG (γ-chain specific) secondary antibody (Southern Biotech Cat #2040-09). Cells were further incubated for 0.5 hr and then washed 1× with FACS Buffer. Cells were resuspended in 300 µl FACS Buffer and the median fluorescence intensity in the FL2-H channel was determined using the FACS Aria flow cytometer (BD).

Figure 3:
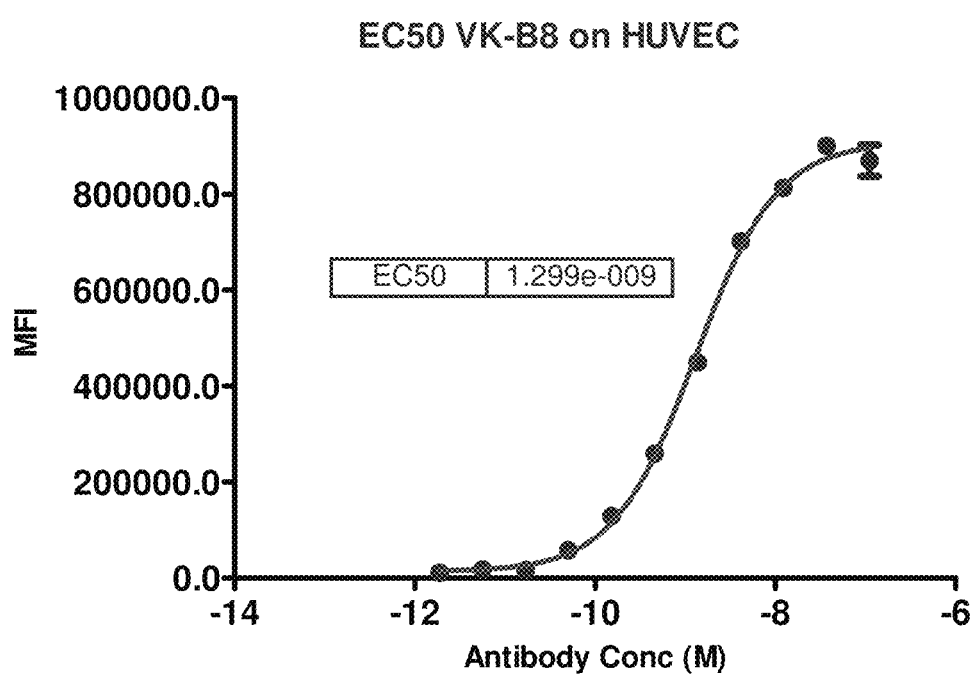
FIG. 3 shows VK-B8 cell binding to HUVE cells and an $EC_{50}$ of about $1.299^{-9}$ M.

Results: The cell binding for the anti-VEGFR2 antibodies disclosed (FIG. 3) on HUVECs was strong compared to background staining (control). The histograms shown depict the number events with specific fluorescence intensities. Blue histograms are the VEGFR2-specific antibody while the red histograms are the background control. Data shown is representative of multiple experiments.

EXAMPLE 8

This example illustrates in vitro data showing inhibition of VEGF-mediated HUVEC proliferation by VK-B8 (anti-VEGFR2) versus FDA approved anti-VEGF Bevacizumab (Avastin®) Protocol: 5000 HUVECs were plated into the wells of a 96-well white opaque cell culture cluster in 100 µl EBM-2 media supplemented with the growth factors etc. (Lonza). 24 hr later, media was removed, cells washed 1× with PBS, and then starved for 18 hr in 50 µl non-supplemented (basal) EBM-2 media. Antibodies were diluted to 2× the indicated concentration in 50 µl non-supplemented (basal) EBM-2 media then added to the cells after removal of the starvation media. After 1 hr incubation, VEGF was added at a concentration of 200 ng/ml in 50 µl (final concentration of VEGF is 100 ng/ml). Cells were then incubated for 48 hr. after which the Promega Cell Titer Glo kit was used to evaluate proliferation. Luminescence output is directly proportional to cell number.

Results: VK-B8 inhibited VEGF-stimulated HUVEC proliferation (FIG. 7). Proliferation inhibition was equal to that conferred by Bevacizumab (Avastin®) at the same dose. Data shown is the mean relative light units of triplicate samples +/− Std Error

EXAMPLE 9

This example illustrates in vitro data showing VEGF stimulated auto-phosphorylation of VEGFR2 receptor in HUVECs. Protocol: 100,000 HUVECs were plated in the wells of a 12-well cell culture cluster in 2.5 ml EBM-2 media supplemented with the growth factors etc. (Lonza). 24 hr. later, media were removed and the cells washed 1× with PBS, and then starved for 18 hr. in 1 ml non-supplemented (basal) EBM-2 media. Antibodies were diluted to 2× the indicated concentration in 1 ml non-supplemented (basal) EBM-2 media then added to the cells after removal of starvation media. After 0.5 hr. incubation, VEGF was added at a concentration of 200 ng/ml in 1 ml basal media (final VEGF concentration is 100 ng/ml). Cells were then incubated for 30 min. Cells were washed with PBS and lysed in 1× Cell Lysis Buffer (Cell Signaling). Phosphorylation of VEGFR2 was detected using the Cell Signaling Path Scan ELISA Antibody Pair (#7824) according to manufacturer's protocol with modification of the volumes to support half-area plates (all volumes cut in half).

Figure 6:
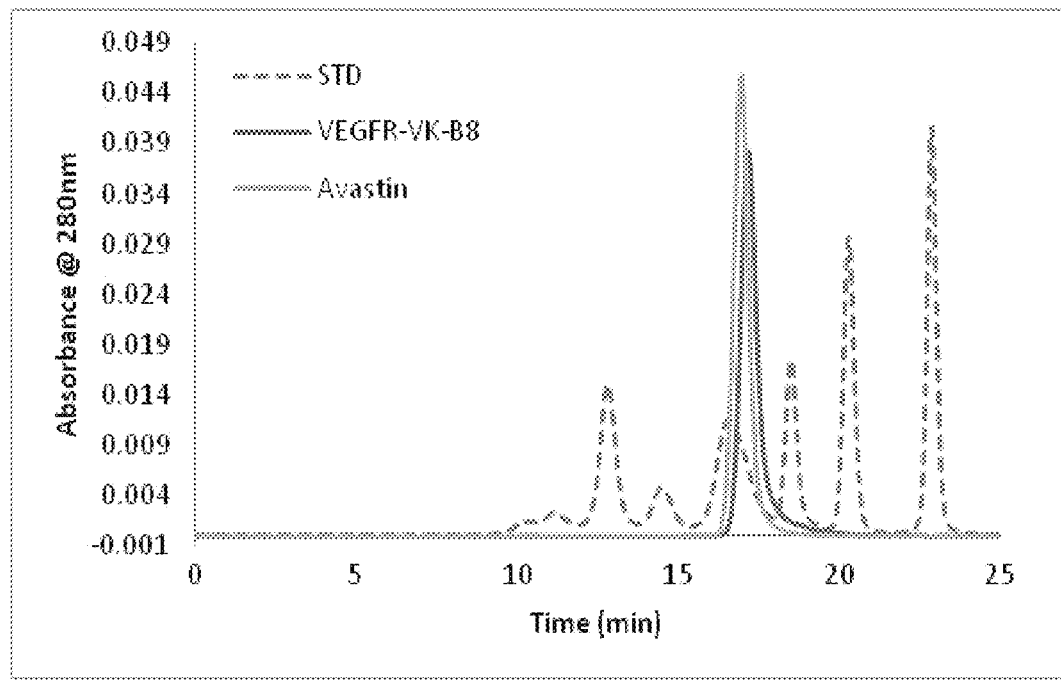
FIG. 6 shows overlaid ANSEC (analytical size-exclusion chromatography) chromatograms of VK-B8 and Avastin® in PBS buffer at pH 6.8: STD/standard run (grey dotted line),VK-B8 spectrum (red), Avastin® spectrum (green).

Results: HUVECs were treated with 100 ng/ml VEGF to stimulate activating auto-phosphorylation of VEGFR2. Pre-treatment of cells with VK-B8 and other clones blocked this activation of VEGFR2. Bevacizumab (Avastin®) treatment shows expected inhibition of VEGFR2 auto-phosphorylation. Data shown (FIG. 6) is the mean absorbance at 450 nm of triplicate samples +/− Std Error.

EXAMPLE 10

Figure 11:
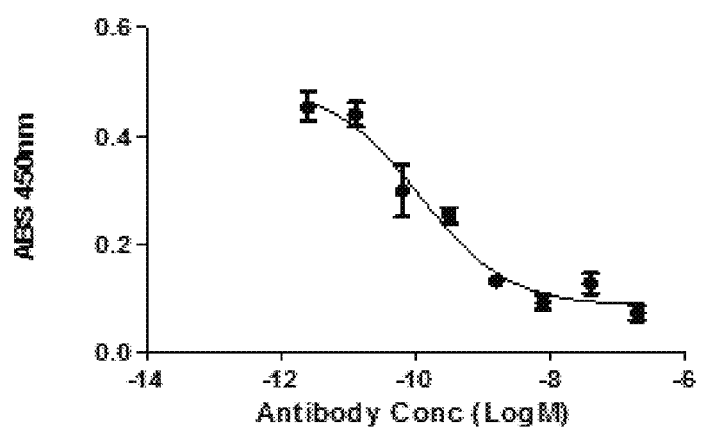
FIG. 11 shows the $IC_{50}$ value for inhibition of VEGF-induced VEGFR2 activation by VK-B8. The $IC_{50}$ is 0.12 nM, that is, inhibition of VEGF-mediated, VEGFR2-activating autophosphorylation.

This example illustrates in vitro data showing the inhibition of VEGF stimulated auto-phosphorylation of the VEGFR2 receptor in HUVECs by VK-B8. Upon binding of VEGF, VEGFR2 undergoes activating auto-phosphorylation at Tyrosine1175 leading to downstream signaling events and the activation of cellular events such as proliferation and cell migration. To assess the ability of VK-B8 to inhibit activation of VEGFR2 by VEGF, 50,000 HUVECs were plated in the wells of a 96-well cell culture cluster in 100 µl EGM-2 media supplemented with growth factors (Lonza). 24 hr. later, the medium was removed and the cells washed 1× with PBS followed by starvation for 18 hr. in 100 µl non-supplemented (basal) EGM-2 media. Cells were then pre-incubated with a serial dilution curve of VK-B8 for 15 minutes, followed by incubation with VEGF at a final concentration of 50 ng/ml for 5 minutes. Cells were washed with PBS and lysed in 1× Cell Lysis Buffer (Cell Signaling). Phosphorylation of VEGFR2 at Tyr1175 was detected using the Cell Signaling Path Scan ELISA Antibody Pair (#7824) according to manufacturer's protocol with modification of the volumes to support half-area plates (all volumes cut in half). Absorbance at 450 nm was plotted vs. antibody concentration and non-linear regression was used to determine the $IC_{50}$ value (FIG. 11). The $IC_{50}$ for VK-B8 inhibition of VEGF-induced VEGFR2 auto-phosphorylation was 0.12 nM.

EXAMPLE 11

Figure 12:
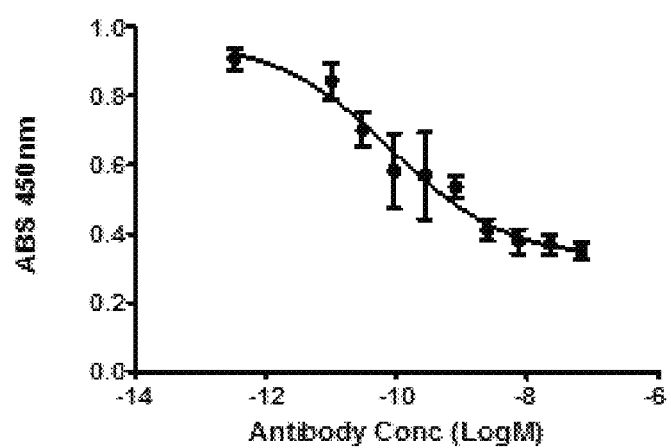
FIG. 12 shows the $IC_{50}$ value for the inhibition of VEGF-induced p44/p42 MAPK (Erk1/2) phosphorylation by VK-B8, or VEGF-mediated p44/p42 MAPK (Erk1/2) phosphorylation. The $IC_{50}$ is 0.08 nM.

This example illustrates in vitro data showing the inhibition of VEGF stimulated phosphorylation of p44/p42 MAPK (Erk1/2) by VK-B8 in HUVECs. Upon binding of VEGF, VEGFR2 undergoes activating auto-phosphorylation, establishing a signaling cascade which results in the activating phosphorylation of p44/p42 MAPK (Erk1/2). To assess the ability of VK-B8 to inhibit this activation, 50,000 HUVECs were plated in the wells of a 96-well cell culture cluster in 100 ul EGM-2 media supplemented with growth factors (Lonza). 24 hr. later, the medium was removed and the cells washed 1× with PBS followed by starvation for 18 hr. in 100 µl non-supplemented (basal) EBM-2 media. Cells were then preincubated with a serial dilution curve of VK-B8 for 15 minutes, followed by incubation with VEGF at a final concentration of 50 ng/ml for 5 minutes. Cells were washed with PBS and lysed in 1× Cell Lysis Buffer (Cell Signaling). Phosphorylation of p44/p42 MAPK (Erk1/2) was detected using a Cell Signaling Path Scan ELISA Antibody Pair (#7246) according to manufacturer's protocol with modification of the volumes to support half-area plates (all volumes cut in half). Absorbance at 450 nm was plotted vs. antibody concentration and non-linear regression was used to determine the $IC_{50}$ value (FIG. 12). The $IC_{50}$ for VK-B8 inhibition of VEGF-induced p44/p42 MAPK (Erk1/2) phosphorylation was 0.08 nM.

EXAMPLE 12

Figure 13:
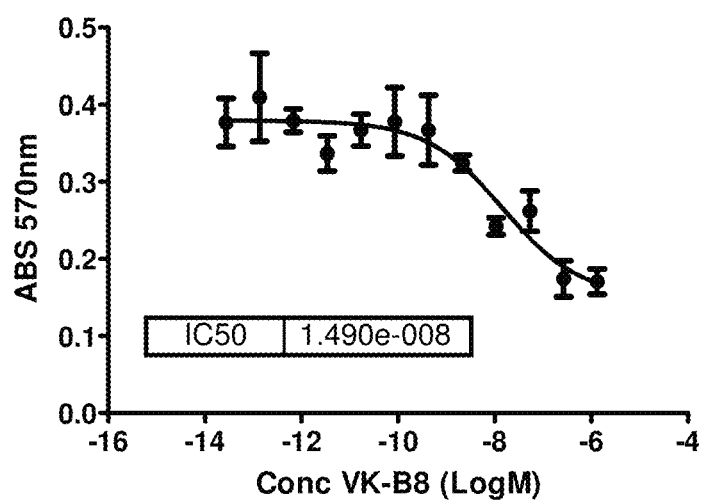
FIG. 13 shows the $IC_{50}$ value for the inhibition of VEGF-induced HUVEC cell proliferation by VK-B8. The $IC_{50}$ is 14.9 nM.

This example illustrates in vitro data showing inhibition of VEGF-mediated HUVEC proliferation by VK-B8. The effect of VEGF activation of VEGFR2 on endothelial cells is to trigger proliferation. In oncology, a tumor will secrete VEGF to manipulate the vascular micro-environment, leading to proliferation and expansion of the vasculature and finally invasion of the vasculature into the tumor. Inhibition of the process has been shown to functionally starve the tumor. To assess the inhibition of VEGF-induced endothelial cell proliferation by VK-B8, 5000 HUVECs were plated into the wells of a 96-well cell culture cluster in 100 µl EGM-2 media supplemented with growth factors (Lonza). 24 hr later, media was removed, cells washed 1× with PBS, and then starved for 18 hr. in 100 µl non-supplemented (basal) EGM-2 media. Cells were then preincubated with a serial dilution curve of VK-B8 for 15 minutes, followed by incubation with VEGF at a final concentration of 50 ng/ml for 48 hr. To measure proliferation, the Promega Cell Titer 96 Non-Radioactive Cell Proliferation kit was used. Absorbance at 570 nm was directly proportional to cell number. Abs570 nm was plotted vs. antibody concentration and non-linear regression was used to determine the $IC_{50}$ for this effect (FIG. 13). The $IC_{50}$ value for the inhibition of proliferation by VK-B8 was 14 nM.

EXAMPLE 13

This example illustrates in vitro data showing inhibition of VEGF-mediated HUVEC migration by VK-B8. An effect of VEGF activation of VEGFR2 on endothelial cells is to trigger cell migration. In oncology, a tumor will secrete VEGF to manipulate the vascular micro-environment, leading to migration and invasion of the vasculature into the tumor. Inhibition of this process has been shown to functionally starve the tumor. To assess the inhibition of VEGF-induced endothelial cell migration by VK-B8, 80,000 HUVECs per sample were preincubated with a serial dilution curve of VK-B8 for 20 minutes and then plated onto the sites of the upper plate of a 96-well modified Boyden Chamber (NeuroProbe, 8 µm pores). The lower chamber of the plate contained VEGF at a final concentration of 5 ng/ml.

Figure 14:
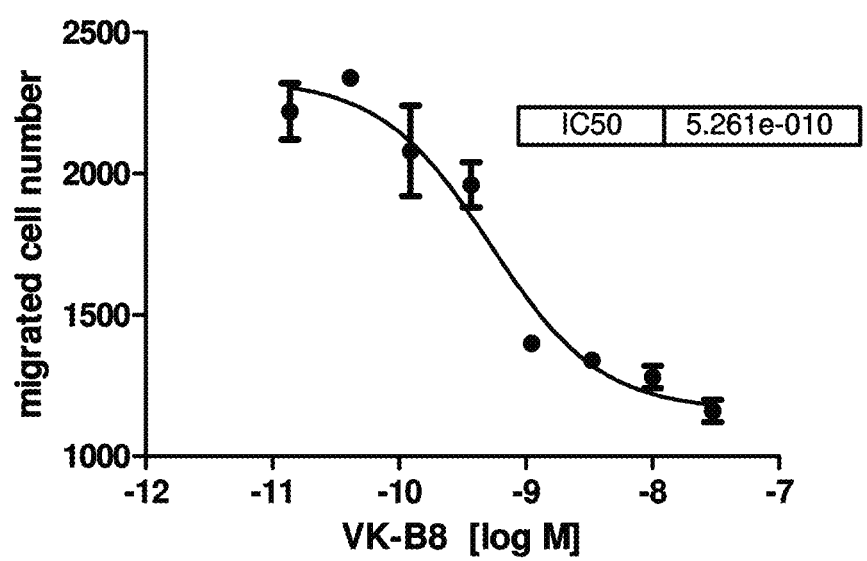
FIG. 14 shows the $IC_{50}$ value for the inhibition of VEGF-induced HUVEC cell migration by VK-B8. The $IC_{50}$ is 0.53 nM.

Twenty hours after the plating of cells, the number of cells which migrated through the membrane to the lower chamber were counted and plotted vs. the antibody concentration (FIG. 14). The $IC_{50}$ value for the inhibition of VEGF-induced HUVEC migration by VK-B8 was calculated using non-linear regression and determined to be 0.5 nM.

EXAMPLE 14

Figure 15:
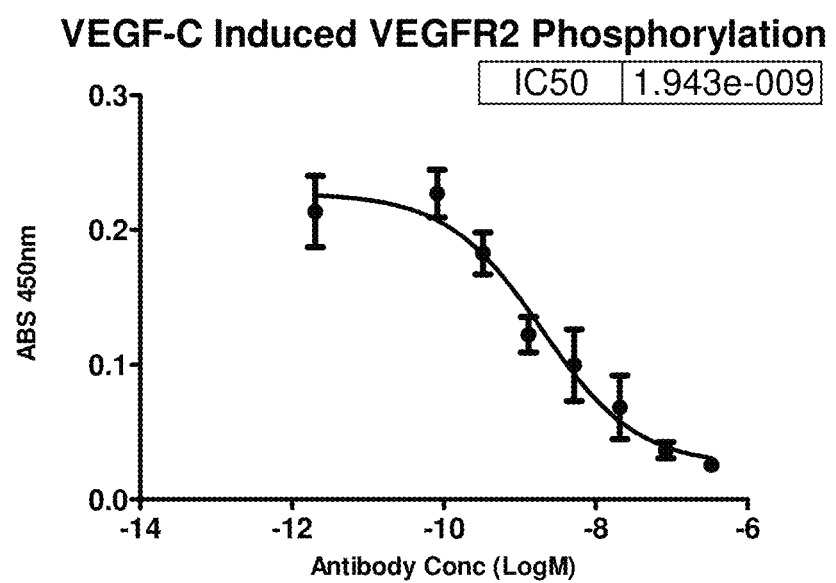
FIG. 15 shows the $IC_{50}$ value for the inhibition of VEGF-C-induced, VEGFR2activation by VK-B8 to show VEGF-C-mediated, VEGFR2-activating autophosphorylation. The $IC_{50}$ is 1.9 nM.

This example illustrates in vitro data showing the inhibition of VEGF-C stimulated auto-phosphorylation of the VEGFR2 receptor in HUVECs by VK-B8. In addition to VEGF (VEGF-A), other members of this growth factor family can bind and activate VEGFR2 leading to functional outcomes. The growth factor VEGF-C can bind and activate VEGFR2 and VEGFR3. Here we demonstrate the ability of VK-B8 to block the activation of VEGFR2 by VEGF-C. To assess the ability of VK-B8 to inhibit activation of VEGFR2 by VEGF-C, 50,000 HUVECs were plated in the wells of a 96-well cell culture cluster in 100 µl EGM-2 media supplemented with growth factors (Lonza). 24 hr. later, the medium was removed and the cells washed 1× with PBS followed by starvation for 18 hr. in 100 µl non-supplemented (basal) EGM-2 media. Cells were then preincubated with a serial dilution curve of STI-A0168 (VK-B8) for 15 minutes, followed by incubation with VEGF-C at a final concentration of 1 µg/ml for 5 minutes. Cells were washed with PBS and lysed in 1× Cell Lysis Buffer (Cell Signaling). Phosphorylation of VEGFR2 at Tyr1175 was detected using the Cell Signaling Path Scan ELISA Antibody Pair (#7824) according to manufacturer's protocol with modification of the volumes to support half-area plates (all volumes cut in half). Absorbance at 450 nm was plotted vs. antibody concentration and non-linear regression was used to determine the $IC_{50}$ value (FIG. 15). The $IC_{50}$ for VK-B8 inhibition of VEGF-C-induced VEGFR2 auto-phosphorylation was 1.9 nM.

EXAMPLE 15

This example provides a summary table of affinity measurements, $EC_{50}$ measurement, $IC_{50}$ measurements of the identified antibodies.

| mAb | VB-A2 | VB-A9 | VB-E1 | VB-F2 | VR-B2 | RV-H5 | VR-B4 | VR-E3 |
|---|---|---|---|---|---|---|---|---|
| ka | 1.44E+6 | 3.71E+4 | 1.80E+5 | 6.16E+4 | 3.36E+5 | 5.39E+5 | 2.04E+5 | 3.75E+4 |
| kd | 1.55E-3 | 2.35E-3 | 1.62E-3 | 2.13E-3 | 3.19E-3 | 5.71E-3 | 2.54E-3 | 8.20E-4 |
| Kd | 1.08E-9 | 6.34E-8 | 9.02E-9 | 3.46E-8 | 9.50E-9 | 1.06E-8 | 1.25E-8 | 2.19E-8 |
| EC50 nM | 0.50 | 0.25 | 0.5 | weak | 0.747 | 0.323 | 24.3 | 1.29 |
| IC50, nM | 25.3 | 2.05 | weak | weak | — | 5.79 | — | 9.32 |

| | VK-A1 | VK-B7 | VK-B8 | VK-C1 | VK-E5 | VK-G9 | 1121* |
|---|---|---|---|---|---|---|---|
| ka | 6.57E+4 | 7.56E+4 | 1.27E+5 | 1.71E+6 | 1.30E+5 | 1.10E+5 | 4.79E+5 |
| kd | 2.42 | 1.92E-3 | 7.75E-4 | 2.01E-3 | 1.16E-3 | 1.91E-3 | 2.5E-5 |
| KD | 3.55E-9 | 3.20E-8 | 6.11E-9 | 1.17E-8 | 8.97E-9 | 1.75E-8 | 5.0E-11 |
| EC50 nM | 0.109 | 1.89 | 0.25 | 2.0 | 0.175 | 0.653 | 0.25 |
| IC50 nM | 3.57 | 7.33 | 2.04 | 57.0 | 3.03 | 5.57 | 0.8 |

*published data in the literature: Lu, D., et al., 278: 43496-43507, JBC (2003)

```
                        Sequence Listing:

Binder  VH                                          VL

VB-A2   MAQVQLVQXGAEVKKPGASVKVSCKASGYTFTSYY         AIQLTQSPSSLSASVGDRVTITCRASQGISNY
        MHWVRQAPGQGLEWMGIINPSGGSTSYAQKFQG           LAWYQQKPGKVPKLLIYAASTLQSGVPSRFS
        RVTMTRDTSTSTVYMELSSLRSEDTAVYYCARDRG         GSGSGTDFTLTISSLQPEDFATYYCQQSYLTP
        MLRHWGMDVWGQGTTVTVSS                        WTFGQGTKVEIK
        SEQ ID NO. 1                                SEQ ID NO. 2

VB-A3   MAQVQLVQSGAEVKKPGASVKVSCKASGHTFNYYY         SYELTQPPSVSVAPGKTASITCGGNNIGSKS
        MHWVRQAPGQGLEWMGQTNLNSGGTNYAPKFQ            VHWYQQKPGQAPVLVIYYDRDRPSGIPERF
        GRVTMTRDTSISTAYMELSSLRSDDTAVYYCANLNS        SGSNSGNTATLTISRVEAGDEADYYCQVWD
        GWFHFENWGQGTLVTVSS                          SSSYHPVFGGGKLTVL
        SEQ ID NO. 3                                SEQ ID NO. 4

VB-A5   MAQMQLVQSGAEVKKPGSSVKVSCEASGGTFSSFA         QPVLTQPPSASGTPGQRVTIFCSGSTSNIGS
        ISWVRQAPGQGLEWMGRVIPVFGTANYAQTFQG           NTVNWYHHLPGTAPKLLIYSNNQRPSGVPD
        RVTITADKSTSTMFMELSSLRSEDTAVYYCARESGDY       RFSGSKSGTSASLAISGLQSADEADYYCAAW
        YDGSRYVDAFDIWGQGTMVTVSS                     DDNLNGWVFGGGTKLTVL
        SEQ ID NO. 5                                SEQ ID NO. 6

VB-A7   MAQVQLVQSGPEVKKPGASVKVSCKASGYTFTSYY         SYVLTQPASVSGSPGQSITISCAGTSSDIGGY
        MHWVRQAPGQGLQWMGIINPSGGSTSYAQNFQG           NSVSWYQQNPGKAPKLMIYEGSKRPSGVS
        GRVTMTRDTSTSTVYMELSSLISQDTAVYYCARSGY        NRFSGSKSGTTASLTISGLQAEDEADYYCSSY
        SSSWLSYGMDVWGQGTTVTVSS                      TNSDTWVFGGGTKLTVL
        SEQ ID NO. 7                                SEQ ID NO. 8
```

-continued

Sequence Listing:

| Binder | VH | VL |
|---|---|---|
| VB-A9 | MAEVQLVESGGGLVKPGGSLRLSCAASGFTFSSYS MNWVRQAPGKGLEWVSSISSGSSYIYYADSLKGRF TISRDNAKNSLYLQMNSLRAEDTAVYYCARDFGNW GQGTLVTVSS SEQ ID NO. 9 | QSALTQPRSVSASPGQSVTISCTGTSSDVGG YDYVSWYQQHPGKAPKLMIYEVSNRPSGV SNRFSGSKSGNTASLSISGLQAEDEADYYCS SYTSTSSPVVFGGGTKLTVL SEQ ID NO. 10 |
| VB-A10 | MAEVQLVESGGGLVQPGGSLRLSCAVSGFTLSSYE MMWVRQAPGKGLEWVSYISDSGGLIYYSDSVKGR FTISRDSAKNSLYLQMNSLRDEDTAVYYCARDEYSS GMDVWGQGTTVTVSS SEQ ID NO. 11 | QPVLTQPPSASGTPGQRVTISCSGSSSNLGS NYVYWYQHLPGTAPKLLIYRNKQRPSGVPD RFSGSKSGTSASLAISGLRSEDEADYYCAVW DGSLSGYVFGTGTKLTVL SEQ ID NO. 12 |
| VB-B6 | MAQVQLVQSGAEVKKPGASVKVSCKASGYTFSSYY MHWVRQAPGQGLEWMGIINPSAGSTNYAQKFQG RVTMTRDTSTSTVYMELSSLRSEDTAVYYCARGYYY DTSGYHGYFKYWGQGTLVTVSS SEQ ID NO. 13 | QSVLTQPRSVSGSPGQSVTISCTGTSSDVGG YNYVSWYQQHPDKAPKLMLYDVSKRPSGV SNRFSGSKSGNTASLTIXALQAEDEADYYCS SYTSSTNLGVFGGGTKVTVL SEQ ID NO. 14 |
| VB-610 | MAEVQLLESGGGLVQPGRSLRLSCAASGFSFDDYA MHWVRQAPGKGLEWVSSISWNSGSRGYADSVKG RFTISRDNAKNSLFLQMNSLRTEDTALYYCAKGVVY SSPYYGMDVWGQGTTVTVSS SEQ ID NO. 15 | QSALTQPPSASGTPGQRVTISCSGSSSNIGT NTVNWYQQLPGTAPRLLIYFNNQRPSGVP DRFSGSKSATSASLAISGLQSEDEADYYCSA WDDILNDPVFGGGTKLTVL SEQ ID NO. 16 |
| VB-D5 | MAQVQLVQSGAEVKKPGASVKISCKASGYIFNTYSI HWVRQAPGQSFEWMGWSSAGDDNTKYSDDFHH RLTIARDTSASTVYMELRGLTSDDTAIYYCARGYELD FWGQGTLVTVSS SEQ ID NO. 17 | QAVLTQPPSASGTPGQRVTISCSGSSSNIGS NTVNWYQQLPGTAPKLLIYSNNQRPSGVP DRFSGSKSGTSASLAISGLQSEDEADYYCAA WDDSLNGDVVFGGGTKVTVL SEQ ID NO. 18 |
| VB-D6 | MAEVQLVESGGDLVKPGGSXRLSCAASGFSFSDYY MSWIRQAPGKGLEWVSSISSSSSYIYYADSVKGRFTI SRDNAKNSLYLQMNSLRAEDTAVYYCARDAPRYG MDVWGQGTTVTVSS SEQ ID NO. 19 | QSALTQPASVSGSPGQTITISCAGTPSDIGLY NYVAWFQHHPGKAPKLIIYDVTKRPSGTSN RFSGSKSGNTASLTISGLQADDEADYFCSSY TTSNSFVLFGEGTKLTVL SEQ ID NO. 20 |
| VB-D11 | MAQVQLVQSGAEVKKPGSSVKVSCKASGGTFSSYA ISWVRQAPGQGLEWMGGIIPIFGTANYAQKFQGR VTITADESTSTAYMELSSLRSEDTAVYYCARGSERVY SSHTYYGMDVWGQGTTVTVSS SEQ ID NO. 21 | QSVVTQQPSVSAAPGQKVTISCSGGSSNIG NNYVSWYQQLPGTAPKLLIYDNNKRPSGIP DRFSGSKSGSSASLAITGLQAEDEADYYCQS YDSSLSGYVFGTGTKLTVL SEQ ID NO. 22 |
| VB-E1 | MAQVQLVESGAEVKKPGASVKVSCKASGYTFTNYYI HWVRQAPGQGLEWMGIINPSSGSTNYAQKFQGR VTMTRDTSTSTVYMELSSLRSEDTAVYYCARQRWD LLDDAFDIWGQGTMVTVSS SEQ ID NO. 23 | DIVMTQSPDSLAVSLGERATINCKTSQSVLY NANNKNYLNWYQQKPGQPPKLLIYWASAR ESGVPDRFSGSGSGTDFTLTIRSLQPDDFAT YYCQQAISFPLTFGGGTKVEIK SEQ ID NO. 24 |
| VB-E2 | MAEVQLVESGGGVVQPGRSLRLSCAASGFTFSSYG MHWVRQAPGKGLEWVAVISYDGSNKYYADSVKG RFTISRDNSKNTLYLQMNSLRAEDTAVYYCAKDWS GPITLWGQGTLVTVSS SEQ ID NO. 25 | SYELMQPPSVSEAPGMTAQITCGGNNIGSK SVHWYQQKPGQAPVLVIYYDSERPSGIPDR FSGSNSGNTASLTINRVEAGDEADYYCQVW DSSSDH HVVFGGGTKLTVL SEQ ID NO. 26 |
| VB-E7 | MAEVQLVESGGGLVQPGGSLRLSCAASGFTFSSYE MNWVRQAPGKGLEWVSYISSSGSTIYYADSVKGRF TISRDNAKNSLYLQMNGLRAEDTAVYYCAREGDSS GFDYWGQGTLVTVSS SEQ ID NO. 27 | QSALTQPPSMSAAPGQKVTISCSGTSSNIG NHYVSWYQRLPDTAPKLLIYDNNRRPSGIP DRFSGSKSGTSATLGITGLQTGDEADYYCGT WDSSLSGYVFGTGTKVTVL SEQ ID NO. 28 |
| VB-F2 | MAQVQLVESGGGLVQPGGSLRLSCAASGFTFSDHY MDWVRQAPGKGLEWVGRIRNKPNSYTSEYAASVK GRFTISRDDSKNSLYLQMNSLRAEDTAVYYCASRSG SYYDHMDVWGQGTTVTVSS SEQ ID NO. 29 | DIVMTQTPLFLPVTLGQPASISCRSSQSLVHS DGNTYLNWFQQRPGQSPRRLIYKVSIRDSG VPGRFSGSGSGTDFTLKISSVEAEDIGVYYC MQGTDRPYTFGQGTKLEIK SEQ ID NO. 30 |
| VB-F8 | MAQMQLVQSGGGVVQPGRSLRLSCVVSGFTFNDY PMHWVRQAPGKGLEWVALLSYDGTSAYYADSVEG RFTISRDNSKNTLYLQMNTLRTEDTAVYYCASEGSP DAFDIWGQGTMVTVSS SEQ ID NO. 31 | QAGLTQSPSVSAAPGQRVTISCTGSSSNIGA GYDVHWYQQLPGTAPKLLIYGNSNRPSGVP DRFSGSKSGTSASLAITGLQAEDEADYYCQS YDSSLSGSVFGGGTKVTVL SEQ ID NO. 32 |

-continued

Sequence Listing:

| Binder | VH | VL |
| --- | --- | --- |
| VB-G4 | MAQVQLVQSGAEVKKPGESLKISCKGSGYSFTSYWI GWVRQMPGKGLEWMGIIYPGDSDTRYSPSFQGQ VTISADKSISTAYLQWSSLKASDTAMYYCARLDYDSS GYYGAFDIWGQGTMVTVSS<br>SEQ ID NO. 33 | QSVVTQPASVSGSPGQSITISCTGTTTDVGA YNYVSWYQHHPGKAPKLIIYDLNNRPSGISN RFSGFKSGNTASLTISGLQAEDEADYYCSSYT SSSTWVFGGGTKLTVL<br>SEQ ID NO. 34 |
| VB-G6 | MAQVQLVESGAEVKKPGASVKVSCKASGYTFTSYY MHWVRQAPGQGLQWMGIINPSGGSTSYAQNFQ GRVTMTRDTSTSTVYMELSSLISEDTAVYYCARSGYS SSWLSYGMDVWGQGTTVTVSS<br>SEQ ID NO. 35 | QAGLTQPPSASGSPGQSVTISCTGTSSDVG GYNYVSWYQQHPGKAPKLMIYEVSKRPSG VPDRFSGSKSGNTASLTVSGLQAEDEADYY CSSFTTSSTWVFGGGTQLTVL<br>SEQ ID NO. 36 |
| VB-H4 | MAEVQLVQSGAEVKKPGASVKLSCKASGYTFNNYA TIWVRQAPEQGLEYVGWISAYSGHTNYAQKLQGR VSMTTDTSTTTAYMELRSLRSDDTAVYYCARWSG WGSYHLLGMDVWGQGTTVTVSS<br>SEQ ID NO. 37 | QPVLTQPPSASGTPGQRVTIYCSGSNSNIGG NSVNWYQQLPGTAPKLLIYHNNQRPSGVP DRFSGSRSGTSASLAISGLQSGDEADYSCAA WDDSLRGYVFGTGTKVTVL<br>SEQ ID NO. 38 |
| VB-H7 | MAQVQLVQSGAEVKKPGASVKVSCKASGYTFTGYY MHWVRQATGQGLEWLGWMNPKTGVTGYAQKF QGRVTMTRNTSINTAYMELNSLTSEDTADYYCARG DYGGPQDMDVWGQGTTVTVSS<br>SEQ ID NO. 39 | QAVLTQPASVSGSPGQSITISCTGTSSDVGG YNYVSWYQQHPGKAPKLMIYEVNNRPSGV SNRFSGSKSGNTASLTISGLQAEDEADYYCT SYTSSNTRMFGGGTKLTVL<br>SEQ ID NO. 40 |
| VB-H9 | MAEVQLVQSGAEVKKPGASVKVSCKASGYTFTGYY MHWVRQAPGQGLEWMGWINPNSGGTNYAQKF QGRVTMTRDTSISTAYMELSRLRSDDTAVYYCARDL QGITIFGVANSPPYYYGMDVWGQGTTVTVSS<br>SEQ ID NO. 41 | QAVLTQPRSVSGSPGQSVTISCTGTRSDVGT YNYVSWYQQLPGKAPKLMIHDVSKRPSGV PDRLSGSKSGNTASLTISGLQSEDEADYYCIS YTLHRTWMFGGGTKLTVL<br>SEQ ID NO. 42 |
| RV-A9 | MAEVQLVQSGAEVKKPGASVKISCKASGYIFNTYSIH WVRQAPGQSFEWMGWSSAGDDNTKYSDDFHHR LTIARDTSASTVYMELRGLTSDDTAIYYCARGYELDF WGQGTLVTVSS<br>SEQ ID NO. 43 | QPVLTQPPSVSGTPGQRVSISCSGSSSNIGS NSVNWYQQLPGTAPRLLIYNNDQRPSGVP DRFSASKSGTSASLAIGGLQSEDEGDYYCSA WDDSLNGPWVFGGGTKLTVL<br>SEQ ID NO. 44 |
| RV-F8 | MAEVQLVESGGGLVKPGGSLRLSCAASGFTFSSYS MNWVRQAPGKGLEWVSSISSSSSYIYYADSVKGRFT ISRDNAKNSLYLQMNSLRAEDTAVYYCARVGATMG DYWGQGTLVTVSS<br>SEQ ID NO. 45 | QSVLTQPPSVSAAPGQKVTISCSGSTSNIAN NFVSWYQQLPGTAPKLLIYDNNKRPSGIPD RFSGSKSGTSATLGITGLQAGDEADYFCGT WDSSLSASYVFGTGTKVTVL<br>SEQ ID NO. 46 |
| RV-H2 | MAQVQLVQSGAEVKKPGESLKISCKGSGYSFTSYWI GWVRQMPGKGLEWMGIIYPGDSDTRYSPSFQGQ VTISADKSTSTAYLQWSSLKASDTAMYYCARLGSSG WYDAFDIWGQGTMVTVSS<br>SEQ ID NO. 47 | DIVMTQSPSSVSAFVGDRVTITCRASQDVG SWLVWYQQKPGKVPKLLIYGASTLQSGVPS RFSGGGSGTDFTLTISSLQPEDFATYYCQQA KSLPYTFGQGTKLE I K<br>SEQ ID NO. 48 |
| RV-H4 | MAQVQLVQSGGGLVKPGGSLRLSCAASGFTFSSYS MNWVRQAPGKGLEWVSSISSSSSYIYYADSVKGRFT ISRDNAKNSLYLQMNSLRAEDTAVYYCARVGATMG DYWGQGTLVTVSS<br>SEQ ID NO. 49 | LPVLTQPASVSGSPGQSITISCTGTDSDVGG YNYVSWYQQHPGKAPKLIISDVSNRPSGVS NRFSGSKSGNTASLTISGLQADDEADYYCNS YTVHATVLFGGGTKVTVL<br>SEQ ID NO. 50 |
| RV-H5 | MAEVQLLESGGGLVKPRGSLRLSCAASGFTFSNAW MSWVRQAPGKGLEWVGRIKSKTDGGTTDYAAPVK GRFTISRDDSKNTLYLQMNSLKTEDTAVYYCTTVWR FGELFRWGQGTLVTVSS<br>SEQ ID NO. 51 | QAGLTQPPSVSVSPGQTASITCSGDKLGDKY ISWYQQKPGQSPVMVIFQDTKRPSGIPERF SGSNSGNTATLTISGTQAMDEADYYCQAW DTSTVFGGGTKLTVL<br>SEQ ID NO. 52 |
| C1 | MAEVQLVQSGSELKKPGASVKISCKASGYTLTNHAL NWVRQAPGQGLEWMAWMNTNTGNPTYAQDFT GRFVFSLDTSVSTAYLEISSLKAEDTAIYYCAREPRDA DAFDIWGQGTMVTVSS<br>SEQ ID NO. 53 | QPVLTQPPSVSVAPGQTARITCGGNNIGSK LVHWYQQKPGQAPVLVVYDDSDRPSGIPE RFSGSNSGNTATLTISRVEAGDEADYYCQV WDSSSDLVVFGGGTKLTVL<br>SEQ ID NO. 54 |
| VR-A2 | MAQVQLVQSGTEVKKPGESLRISCRSSGYKFTNYWI GWVRQLPGQGLEWMGVILPGDSDTRYGPSFQGH VSISVDKSISTVYLEWESLKASDTAMYYCASWDNFD HWGQGTLVTVSS<br>SEQ ID NO. 55 | QSVTQPPSVSAAPRQKVTISCSGSSSNIGN NYVSWYQQLPGTAPKLLIYDNNRRPSGIPD RFSGSKSGTSATLGITGLQTGDEADYYCGT WDSSLSAGVFGTGTKVTVL<br>SEQ ID NO. 56 |

Sequence Listing:

| Binder | VH | VL |
| --- | --- | --- |
| VR-A3 | MAEVQLVQSGAEVKKPGTSVTISCKTSGYTFTTYYIH WVRQAPGQGLEWMGIILPSGGNTNYAPNFQGRV TMTRDTSTSTVNMELSSLTSDDTAVYYCVREYRGGY FDYWGQGTLVTVSS<br>SEQ ID NO. 57 | AIRMTQSPDSLAVSLGERATINCKSSQSVLY SSNNKNYLAWYQQKPGQPPKLLIYWASTRE SGVPDRFSGSGSGTDFTLTISSLQAEDVAVY YCQQYYSTPYTFGQGTKLEIK<br>SEQ ID NO. 58 |
| VR-A10 | MAQVQLVESGAEVKKPGASVKVSCKASGYTFTSYY MHWVRQAPGQGLEWMGIINPSGGSTSYAQKFQG RVTMTRDTSTSTVYMELSSLRSEDTAVYYCAREGAN APNSYYYMDVWGKGTTVTVSS<br>SEQ ID NO. 59 | QSVVTQPPSVSGAPGQRVTISCTGSSSNIGA GYDVHWYKQLPGTAPKLLIYGNNNRPSGV PDRFSGSKSGTSASLAITGLQAEDEADYYCQ SYDSSLSEGVFGTGTKVTVL<br>SEQ ID NO. 60 |
| VR-B2 | MAEVQLLESGGGLVQPGGSLRLSCAASGFTFSSYA MHWVRQAPGKGLEWVAVISYDGSNKYYADSVKG RFTISRDNSKNTLYLQMNSLRAEDTAVYYCARDLGA ASYWYFDLWGRGTLVTVSS<br>SEQ ID NO. 61 | DIQLTQSPPSVSASVGDRVTITCRASQDIST WLAWYQQKPGSAPKVLIYAASTFQSGVPSR FRGSGSGTYFTLTISGLQPEDFATYYCQQGN SFPPTFGQGTKLEIK<br>SEQ ID NO. 62 |
| VR-B4 | MAQVQLVQSGAEVKKPGSSVKVSCKAYGGTFGSY GVSWYRRAPGQGLEWMGRLIPIFGTRDYAQKFQG RVTLTADESTNTAYMELSSLRSEDTAVYYCARDGDY YGSGSYYGMDVWGQGTTVTVSS<br>SEQ ID NO. 63 | SYELTQPASVSGSPGQSITISCTGSSSDVGGY NFVSWYRQHAGKAPKLMIYDVTNRPSGVS TRFSGSKSGTTASLTISGLQPDDEAHYYCSSY TTTSTWVFGGGTKLTVL<br>SEQ ID NO. 64 |
| VR-B11 | MAEVQLVESGGGVVQPGRSLRLSCAASGFTFSSYG MHWVRQAPGKGLEWVAVISYDGSNKYYADSVKG RFTISRDNSKNTLYLQMNSLRAEDTAVYYCAKDGYS YGGGFDYWGQGTLVTVSS<br>SEQ ID NO. 65 | QSVVTQPPSVSAAPGQRVTISCTGSSSNIGA GYDVHWYQQLPGTAPKLLIYANNNRPSGV PDRFSGSKTGTSASLAITGLQADDEADYFCQ SYDSSLSGWVFGGGTKLTVL<br>SEQ ID NO. 66 |
| VR-C5 | MAEVQLVESGGGLVKPGGSLRLSCAASGFTFSSYS MNWVRQAPGKGLEWVSSISSGSSYIYYADSLKGRF TISRDNAKNSLYLQMNSLRAEDTAVYYCARDFGNW GQGTLVTVSS<br>SEQ ID NO. 67 | QSVLTQPASVSGSPGQSITISCTGTSSDVGG YNYVSWYQQHPGKAPKLMIYDVSNRPSGV SNRFSGSKSGNTASLTISGLQAEDEADYYCS SYTSSSTPYVFGTGTKVTVL<br>SEQ ID NO. 68 |
| VR-C7 | MAQVQLVESGGGLVQPGGSLRLSCAASGFNFSSYE MNWVRQAPGKGLEWVSYISSSGSTKHYADSVKGR FTISRDNAKNSLYLQMNSLRAEDTAVYYCAREHYNS WYFDLWGRGTLVTVSS<br>SEQ ID NO. 69 | SYELMQPHSVSESPGKTVTISCTGSSGSIASN YVQWYQQRPGSAPTTVIYEDDQRPSGVPD RFSGSIDSSSNSAALTISGLKTEDEADYYCQS YDSANVVFGGGTKLTVL<br>SEQ ID NO. 70 |
| VR-C11 | MAEVQLLESGGGWVKPGGSLRLSCAASGFPFSDYY MTWVRQAPGKGLEWVSYITTGGRIIYSADSVRGRF TISRDNAKNSVYLQMNSLRAEDTAVYYCARPLRELS PGGFDLWGRGTMVTVSS<br>SEQ ID NO.71 | LPVLTQPPSVSAAPGQKVTIPCSGTYSNIVN NYVSWYQQLPGTAPKLLIYDNNKRPSGIPD RFSGSKSGTSATLGITGLQTGDEADYYCGT WDNSLRRWVFGEGTKLTVL<br>SEQ ID NO. 72 |
| VR-E3 | MAEVQLVESGGGLVKPGGSLRLSCAASGFTFSSYS MNWVRQAPGKGLEWVSSISSASSYIYYADSVKGRF TISRDNAKKSLYLQLNSLTVEDTAVYYCAREYWGSP DYWGRGTLVTVSS<br>SEQ ID NO. 73 | QPVLTQPPSASGSPGQSVTISCTGTSSDVGG YNYVSWYQQHPGKAPKLMIYDVNNRPSGV PDRFSGSKSGNTASLTISGLQAEDEADYYCS SYTSSSTRVFGGGTKLTVL<br>SEQ ID NO. 74 |
| VR-G11 | MAEVQLVESGGGLVKPGGSLRLSCAASGFTFSSYS MNWVSWYQQLPGKGLEWVSSISSSSSYIYYADSVKGRFT ISRDNAKNSLYLQMNSLRAEDTAVYYCARGGVSPG DYWGQGTLVTVSS<br>SEQ ID NO. 75 | QSVVTQPPSVSAAPGQKVTISCSGSSSNIGN NYVSWYQQLPGTAPKLLIYDYNKRPSGIPDR FSGSQSGTSATLGITGLQTGDEADYYCGTW DSSLTLYVFGTGTKLTVL<br>SEQ ID NO. 76 |
| VK-B8 | MAQVQLVQSGAEVKKPGSSVKVSCKAYG GTFGSYGVSWVRRAPGQGLEWMGRLIPI FGTRDYAQKFQGRVTLTADESTNTAYMEL SSLRSEDTAVYYCARDGDYYGSGSYYGMD VWGQGTLVTVSS<br>SEQ ID NO. 77 | ETTLTQSPATLSVSPGERATVSCRASQSLGS NLGWFQQKPGQAPRLLIYGASTRATGIPAR FSGSGSGTEFTLTISSLQSEDFAVYFCQQYN DWPITFGQGTRLEIK<br>SEQ ID NO. 78 |
| VR-H9 | MAQMQLVQSGAEVKKPGSSVKVSCKASGGTFSSY AISWVRQAPGQGLEWMGRIIPILGIANYAQKFQGR VTITADKSTSTAYMELSSLRSEDTAVYYCARGHDYYG SGNNQEDYFDPWGQGTLVTVSS<br>SEQ ID NO. 79 | QPVLTQPPSVSKDLRQTATLTCTGNGNNVG YQGAAWLQQHQGHPPKLLSYRNNNRPSGI SERFSASRSGNTASLTISGLQPEDEADYFCSA WDNSLSAWVFGGGTKLTVL<br>SEQ ID NO. 80 |

-continued

| Sequence Listing: | | |
|---|---|---|
| Binder | VH | VL |
| VK-B8A | MAQVQLVQSGAEVKKPGSSVKVSCKAYG GTFGSYGVSWVRRAPGQGLEWMGRLIPI FGTRDYAQKFQGRVTLTADESTNTAYMEL SSLRSEDTAVYYCARDGDYYGSGSYYGMD VWGQGTLVTVSS SEQ ID NO. 77 | ETTLTQSPATLSVSPGERATVSCRASQSLGS NLGWFQQKPGQAPRLLIYGASTRATGIPAR FSGSGSGTEFTLTISSLQSEDFAVYFCQQYN DWPITFGQGTKLEIK SEQ ID NO. 81 |

We claim:

1. A recombinant fully human anti-vascular endothelial growth factor receptor 2 (VEGFR2) antibody, or an antigen binding fragment thereof, that binds to VEGFR2 comprising complementarity determining regions (CDRs) as set forth in a heavy chain variable domain amino acid sequence selected from the group consisting of SEQ ID NO. 9, SEQ ID NO. 23, SEQ ID NO. 51, SEQ ID NO. 63, SEQ ID NO. 73 and SEQ ID NO. 77, and comprising CDRs as set forth in a light chain variable domain amino acid sequence selected from the group consisting of SEQ ID NO. 10, SEQ ID NO. 24, SEQ ID NO. 52, SEQ ID NO. 64, SEQ ID NO. 78, and SEQ ID NO. 81.

2. The recombinant fully human anti-VEGFR2 antibody, or antigen-binding fragment thereof, of claim 1, comprising a heavy chain/light chain variable domain amino acid sequence selected from the group consisting of SEQ ID NO. 9/SEQ ID NO. 10, SEQ ID NO. 23/SEQ ID NO. 24, SEQ ID NO. 51/SEQ ID NO. 52, SEQ ID NO. 63/SEQ ID NO. 64, SEQ ID NO. 73/SEQ ID NO. 74, SEQ ID NO. 77/SEQ ID NO. 78, and SEQ ID NO. 77/SEQ ID NO. 81.

3. The recombinant anti-VEGFR2 antibody or antigen-binding fragment thereof, of claim 1, wherein the antibody, or antigen-binding fragment thereof, is classified as an isotype selected from the group consisting of: IgG, IgM, IgD, IgA, and IgE.

4. The recombinant anti-VEGFR2 antibody, or antigen-binding fragment thereof, of claim 3, wherein the antibody is an IgG1 or an IgG4.

5. The recombinant anti-VEGFR2 antibody, or antigen-binding fragment thereof, of claim 1, wherein the antibody, or antigen-binding fragment thereof, is a monoclonal antibody, a Fab, a Fab', a F(ab')$_2$, a Fv, a domain antibody (dAb), a single-chain antibody (scFv), a chimeric antibody, a diabody, a triabody or a tetrabody.

6. The recombinant anti-VEGFR2 antigen binding fragment of claim 5, which is a scFv.

7. The recombinant anti-VEGFR2 antigen binding fragment of claim 5, which is a Fab.

8. The recombinant anti-VEGFR2 antibody, or an antigen-binding fragment thereof, of claim 1, wherein the antibody, or antigen-binding fragment thereof, comprises a heavy chain variable domain and a light chain variable domain selected from the group consisting of:
- a) a heavy chain variable domain comprising the CDRs as set forth in SEQ ID NO. 9 and which comprises an amino acid sequence that is at least 95% identical to SEQ ID NO. 9, and a light chain variable domain comprising the CDRs as set forth in SEQ ID NO. 10 and which comprises an amino acid sequence that is at least 95% identical to SEQ ID NO. 10;
- b) a heavy chain variable domain comprising the CDRs as set forth in SEQ ID NO. 23 and which comprises an amino acid sequence that is at least 95% identical to SEQ ID NO: 23, and comprising a light chain variable domain comprising the CDRs as set forth in SEQ ID NO. 24 and which comprises an amino acid sequence that is at least 95% identical to SEQ ID NO. 24;
- c) a heavy chain variable domain comprising the CDRs as set forth in SEQ ID NO. 51 and which comprises an amino acid sequence that is at least 95% identical to SEQ ID NO. 51, and comprising a light chain variable domain comprising the CDRs as set forth in SEQ ID NO. 52 and which comprises an amino acid sequence that is at least 95% identical to SEQ ID NO. 52;
- d) a heavy chain variable domain comprising the CDRs as set forth in SEQ ID NO. 63 and which comprises an amino acid sequence that is at least 95% identical to SEQ ID NO. 63, and comprising a light chain variable domain comprising the CDRs as set forth in SEQ ID NO. 64 and which comprises an amino acid sequence that is at least 95% identical to SEQ ID NO. 64;
- e) a heavy chain variable domain comprising the CDRs as set forth in SEQ ID NO. 73 and which comprises an amino acid sequence that is at least 95% identical to SEQ ID NO. 73, and comprising a light chain variable domain comprising the CDRs as set forth in SEQ ID NO. 74 and which comprises an amino acid sequence that is at least 95% identical to SEQ ID NO. 74;
- f) a heavy chain variable domain comprising the CDRs as set forth in SEQ ID NO. 77 and which comprises an amino acid sequence that is at least 95% identical to SEQ ID NO. 77, and comprising a light chain variable domain comprising the CDRs as set forth in SEQ ID NO. 78 and which comprises an amino acid sequence that is at least 95% identical to SEQ ID NO. 78; and
- g) a heavy chain variable domain comprising the CDRs as set forth in SEQ ID NO. 77 and which comprises an amino acid sequence that is at least 95% identical to SEQ ID NO. 77, and comprising a light chain variable domain comprising the CDRs as set forth in SEQ ID NO. 81 and which comprises an amino acid sequence that is at least 95% identical to SEQ ID NO. 81.

9. The recombinant anti-VEGR2 antigen-binding fragment of claim 8, which is a Fab or a scFv.

10. A pharmaceutical composition comprising the recombinant anti-VEGFR2 antibody, or antigen-binding fragment thereof, of claim 1, and a pharmaceutically acceptable carrier.

11. A method of treating cancer in a human subject in need thereof, the method comprising the step of administering an effective amount of the recombinant anti-VEGFR2 antibody, or antigen-binding fragment thereof, of claim 1 to the subject, such that the cancer is treated.

12. The method of claim 11, wherein the cancer is selected from the group consisting of leukemia, bladder cancer, bone cancer, brain cancer, breast cancer, cartilage cancer, colon cancer, kidney cancer, liver cancer, lung cancer, lymph node cancer, nervous tissue cancer, ovary cancer, pancreatic cancer, prostate cancer, skeletal muscle cancer, skin cancer, spinal cord cancer, spleen cancer, stomach cancer, testes cancer, thymus cancer, thyroid cancer, trachea cancer, urogenital tract cancer, ureter cancer, urethra cancer, uterus cancer, and vaginal cancer.

\* \* \* \* \*

UNITED STATES PATENT AND TRADEMARK OFFICE
CERTIFICATE OF CORRECTION

Page 1 of 1

PATENT NO. : 11,111,304 B2
APPLICATION NO. : 14/680865
DATED : September 7, 2021
INVENTOR(S) : Randy Gastwirt et al.

It is certified that error appears in the above-identified patent and that said Letters Patent is hereby corrected as shown below:

On the Title Page

Between item (65) Prior Publication Data and item (51) Int. Cl., insert:
--Related U.S. Application Data
(60) Continuation of application No. 13/854,071, filed on March 30, 2013, now Pat. No. 9,029,510.
(60) Provisional application No. 61/618,658, filed on March 30, 2012.--

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 81

<210> SEQ ID NO 1
<211> LENGTH: 123
<212> TYPE: PRT
<213> ORGANISM: homo Sapians
<220> FEATURE:
<221> NAME/KEY: misc_feature
<222> LOCATION: (9)..(9)
<223> OTHER INFORMATION: Xaa can be any naturally occurring amino acid

<400> SEQUENCE: 1

Met Ala Gln Val Gln Leu Val Gln Xaa Gly Ala Glu Val Lys Lys Pro
1               5                   10                  15

Gly Ala Ser Val Lys Val Ser Cys Lys Ala Ser Gly Tyr Thr Phe Thr
            20                  25                  30

Ser Tyr Tyr Met His Trp Val Arg Gln Ala Pro Gly Gln Gly Leu Glu
        35                  40                  45

Trp Met Gly Ile Ile Asn Pro Ser Gly Gly Ser Thr Ser Tyr Ala Gln
    50                  55                  60

Lys Phe Gln Gly Arg Val Thr Met Thr Arg Asp Thr Ser Thr Ser Thr
65                  70                  75                  80

Val Tyr Met Glu Leu Ser Ser Leu Arg Ser Glu Asp Thr Ala Val Tyr
                85                  90                  95

Tyr Cys Ala Arg Asp Arg Gly Met Leu Arg His Trp Gly Met Asp Val
            100                 105                 110

Trp Gly Gln Gly Thr Thr Val Thr Val Ser Ser
        115                 120

<210> SEQ ID NO 2
<211> LENGTH: 107
<212> TYPE: PRT
<213> ORGANISM: homo sapians

<400> SEQUENCE: 2

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Tyr Leu Thr Pro Trp
                85                  90                  95

Thr Phe Gly Gln Gly Thr Lys Val Glu Ile Lys
            100                 105

<210> SEQ ID NO 3
<211> LENGTH: 121
<212> TYPE: PRT
<213> ORGANISM: homo sapians

<400> SEQUENCE: 3

Met Ala Gln Val Gln Leu Val Gln Ser Gly Ala Glu Val Lys Lys Pro
1               5                   10                  15

Gly Ala Ser Val Lys Val Ser Cys Lys Ala Ser Gly His Thr Phe Asn
            20                  25                  30

Tyr Tyr Met His Trp Val Arg Gln Ala Pro Gly Gln Gly Leu Glu
        35                  40                  45

Trp Met Gly Gln Thr Asn Leu Asn Ser Gly Gly Thr Asn Tyr Ala Pro
    50                  55                  60

Lys Phe Gln Gly Arg Val Thr Met Thr Arg Asp Thr Ser Ile Ser Thr
65                  70                  75                  80

Ala Tyr Met Glu Leu Ser Ser Leu Arg Ser Asp Thr Ala Val Tyr
                85                  90                  95

Tyr Cys Ala Asn Leu Asn Ser Gly Trp Phe His Phe Glu Asn Trp Gly
            100                 105                 110

Gln Gly Thr Leu Val Thr Val Ser Ser
            115                 120

<210> SEQ ID NO 4
<211> LENGTH: 108
<212> TYPE: PRT
<213> ORGANISM: homo sapians

<400> SEQUENCE: 4

Ser Tyr Glu Leu Thr Gln Pro Pro Ser Val Ser Val Ala Pro Gly Lys
1               5                   10                  15

Thr Ala Ser Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Arg Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Tyr His
                85                  90                  95

Pro Val Phe Gly Gly Gly Thr Lys Leu Thr Val Leu
            100                 105

<210> SEQ ID NO 5
<211> LENGTH: 128
<212> TYPE: PRT
<213> ORGANISM: homo sapians
```

<400> SEQUENCE: 5

Met Ala Gln Met Gln Leu Val Gln Ser Gly Ala Glu Val Lys Lys Pro
1               5                   10                  15

Gly Ser Ser Val Lys Val Ser Cys Glu Ala Ser Gly Gly Thr Phe Ser
                20                  25                  30

Ser Phe Ala Ile Ser Trp Val Arg Gln Ala Pro Gly Gln Gly Leu Glu
            35                  40                  45

Trp Met Gly Arg Val Ile Pro Val Phe Gly Thr Ala Asn Tyr Ala Gln
50                  55                  60

Thr Phe Gln Gly Arg Val Thr Ile Thr Ala Asp Lys Ser Thr Ser Thr
65                  70                  75                  80

Met Phe Met Glu Leu Ser Ser Leu Arg Ser Glu Asp Thr Ala Val Tyr
                85                  90                  95

Tyr Cys Ala Arg Glu Ser Gly Asp Tyr Tyr Asp Gly Ser Arg Tyr Val
            100                 105                 110

Asp Ala Phe Asp Ile Trp Gly Gln Gly Thr Met Val Thr Val Ser Ser
            115                 120                 125

<210> SEQ ID NO 6
<211> LENGTH: 110
<212> TYPE: PRT
<213> ORGANISM: homo sapians

<400> SEQUENCE: 6

Gln Pro Val Leu Thr Gln Pro Ser Ala Ser Gly Thr Pro Gly Gln
1               5                   10                  15

Arg Val Thr Ile Phe Cys Ser Gly Ser Thr Ser Asn Ile Gly Ser Asn
                20                  25                  30

Thr Val Asn Trp Tyr His His Leu Pro Gly Thr Ala Pro Lys Leu Leu
            35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Ala Asp Glu Ala Asp Tyr Tyr Cys Ala Ala Trp Asp Asp Asn Leu
                85                  90                  95

Asn Gly Trp Val Phe Gly Gly Gly Thr Lys Leu Thr Val Leu
            100                 105                 110

<210> SEQ ID NO 7
<211> LENGTH: 125
<212> TYPE: PRT
<213> ORGANISM: homo sapians

<400> SEQUENCE: 7

Met Ala Gln Val Gln Leu Val Gln Ser Gly Pro Glu Val Lys Lys Pro
1               5                   10                  15

Gly Ala Ser Val Lys Val Ser Cys Lys Ala Ser Gly Tyr Thr Phe Thr
                20                  25                  30

Ser Tyr Tyr Met His Trp Val Arg Gln Ala Pro Gly Gln Gly Leu Gln
            35                  40                  45

Trp Met Gly Ile Ile Asn Pro Ser Gly Gly Ser Thr Ser Tyr Ala Gln
50                  55                  60

```
Asn Phe Gln Gly Arg Val Thr Met Thr Arg Asp Thr Ser Thr Ser Thr
 65                  70                  75                  80

Val Tyr Met Glu Leu Ser Ser Leu Ile Ser Gln Asp Thr Ala Val Tyr
                 85                  90                  95

Tyr Cys Ala Arg Ser Gly Tyr Ser Ser Ser Trp Leu Ser Tyr Gly Met
            100                 105                 110

Asp Val Trp Gly Gln Gly Thr Thr Val Thr Val Ser Ser
        115                 120                 125
```

<210> SEQ ID NO 8
<211> LENGTH: 110
<212> TYPE: PRT
<213> ORGANISM: homo sapians

<400> SEQUENCE: 8

```
Ser Tyr Val Leu Thr Gln Pro Ala Ser Val Ser Gly Ser Pro Gly Gln
  1               5                  10                  15

Ser Ile Thr Ile Ser Cys Ala Gly Thr Ser Ser Asp Ile Gly Gly Tyr
             20                  25                  30

Asn Ser Val Ser Trp Tyr Gln Gln Asn Pro Gly Lys Ala Pro Lys Leu
         35                  40                  45

Met Ile Tyr Glu Gly Ser Lys Arg Pro Ser Gly Val Ser Asn Arg Phe
 50                  55                  60

Ser Gly Ser Lys Ser Gly Thr Thr Ala Ser Leu Thr Ile Ser Gly Leu
 65                  70                  75                  80

Gln Ala Glu Asp Glu Ala Asp Tyr Tyr Cys Ser Ser Tyr Thr Asn Ser
                 85                  90                  95

Asp Thr Trp Val Phe Gly Gly Gly Thr Lys Leu Thr Val Leu
            100                 105                 110
```

<210> SEQ ID NO 9
<211> LENGTH: 115
<212> TYPE: PRT
<213> ORGANISM: homo sapians

<400> SEQUENCE: 9

```
Met Ala Glu Val Gln Leu Val Glu Ser Gly Gly Gly Leu Val Lys Pro
  1               5                  10                  15

Gly Gly Ser Leu Arg Leu Ser Cys Ala Ala Ser Gly Phe Thr Phe Ser
             20                  25                  30

Ser Tyr Ser Met Asn Trp Val Arg Gln Ala Pro Gly Lys Gly Leu Glu
         35                  40                  45

Trp Val Ser Ser Ile Ser Ser Gly Ser Ser Tyr Ile Tyr Tyr Ala Asp
 50                  55                  60

Ser Leu Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                 85                  90                  95

Tyr Cys Ala Arg Asp Phe Gly Asn Trp Gly Gln Gly Thr Leu Val Thr
            100                 105                 110

Val Ser Ser
        115
```

<210> SEQ ID NO 10
<211> LENGTH: 111
<212> TYPE: PRT
<213> ORGANISM: homo sapians

<400> SEQUENCE: 10

Gln Ser Ala Leu Thr Gln Pro Arg Ser Val Ser Ala Ser Pro Gly Gln
1               5                   10                  15

Ser Val Thr Ile Ser Cys Thr Gly Thr Ser Ser Asp Val Gly Gly Tyr
            20                  25                  30

Asp Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Ser Ile Ser Gly Leu
65                  70                  75                  80

Gln Ala Glu Asp Glu Ala Asp Tyr Tyr Cys Ser Ser Tyr Thr Ser Thr
                85                  90                  95

Ser Ser Pro Val Val Phe Gly Gly Gly Thr Lys Leu Thr Val Leu
            100                 105                 110

<210> SEQ ID NO 11
<211> LENGTH: 120
<212> TYPE: PRT
<213> ORGANISM: homo sapians

<400> SEQUENCE: 11

Met Ala Glu Val Gln Leu Val Glu Ser Gly Gly Gly Leu Val Gln Pro
1               5                   10                  15

Gly Gly Ser Leu Arg Leu Ser Cys Ala Val Ser Gly Phe Thr Leu Ser
            20                  25                  30

Ser Tyr Glu Met Met Trp Val Arg Gln Ala Pro Gly Lys Gly Leu Glu
        35                  40                  45

Trp Val Ser Tyr Ile Ser Asp Ser Gly Gly Leu Ile Tyr Tyr Ser Asp
    50                  55                  60

Ser Val Lys Gly Arg Phe Thr Ile Ser Arg Asp Ser Ala Lys Asn Ser
65                  70                  75                  80

Leu Tyr Leu Gln Met Asn Ser Leu Arg Asp Glu Asp Thr Ala Val Tyr
                85                  90                  95

Tyr Cys Ala Arg Asp Glu Tyr Ser Ser Gly Met Asp Val Trp Gly Gln
            100                 105                 110

Gly Thr Thr Val Thr Val Ser Ser
        115                 120

<210> SEQ ID NO 12
<211> LENGTH: 110
<212> TYPE: PRT
<213> ORGANISM: homo sapians

<400> SEQUENCE: 12

Gln Pro Val Leu Thr Gln Pro Pro Ser Ala Ser Gly Thr Pro Gly Gln
1               5                   10                  15

Arg Val Thr Ile Ser Cys Ser Gly Ser Ser Asn Leu Gly Ser Asn
            20                  25                  30

Tyr Val Tyr Trp Tyr Gln His Leu Pro Gly Thr Ala Pro Lys Leu Leu
        35                  40                  45

Ile Tyr Arg Asn Lys Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

```
Ser Glu Asp Glu Ala Asp Tyr Tyr Cys Ala Val Trp Asp Gly Ser Leu
                85                  90                  95

Ser Gly Tyr Val Phe Gly Thr Gly Thr Lys Leu Thr Val Leu
            100                 105                 110

<210> SEQ ID NO 13
<211> LENGTH: 126
<212> TYPE: PRT
<213> ORGANISM: homo sapians

<400> SEQUENCE: 13

Met Ala Gln Val Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Ser
            20                  25                  30

Ser Tyr Tyr Met His Trp Val Arg Gln Ala Pro Gly Gln Gly Leu Glu
        35                  40                  45

Trp Met Gly Ile Ile Asn Pro Ser Ala Gly Ser Thr Asn Tyr Ala Gln
50                  55                  60

Lys Phe Gln Gly Arg Val Thr Met Thr Arg Asp Thr Ser Thr Ser Thr
65                  70                  75                  80

Val Tyr Met Glu Leu Ser Ser Leu Arg Ser Glu Asp Thr Ala Val Tyr
                85                  90                  95

Tyr Cys Ala Arg Gly Tyr Tyr Asp Thr Ser Gly Tyr His Gly Tyr
            100                 105                 110

Phe Lys Tyr Trp Gly Gln Gly Thr Leu Val Thr Val Ser Ser
        115                 120                 125

<210> SEQ ID NO 14
<211> LENGTH: 111
<212> TYPE: PRT
<213> ORGANISM: homo sapians
<220> FEATURE:
<221> NAME/KEY: misc_feature
<222> LOCATION: (78)..(78)
<223> OTHER INFORMATION: Xaa can be any naturally occurring amino acid

<400> SEQUENCE: 14

Gln Ser Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Leu Tyr Asp Val Ser Lys Arg Pro Ser Gly Val Ser Asn Arg Phe
50                  55                  60

Ser Gly Ser Lys Ser Gly Asn Thr Ala Ser Leu Thr Ile Xaa Ala Leu
65                  70                  75                  80

Gln Ala Glu Asp Glu Ala Asp Tyr Tyr Cys Ser Ser Tyr Thr Ser Ser
                85                  90                  95

Thr Asn Leu Gly Val Phe Gly Gly Gly Thr Lys Val Thr Val Leu
            100                 105                 110

<210> SEQ ID NO 15
<211> LENGTH: 124
<212> TYPE: PRT
<213> ORGANISM: homo sapians
```

```
<400> SEQUENCE: 15

Met Ala Glu Val Gln Leu Leu Glu Ser Gly Gly Gly Leu Val Gln Pro
1               5                   10                  15

Gly Arg Ser Leu Arg Leu Ser Cys Ala Ala Ser Gly Phe Ser Phe Asp
            20                  25                  30

Asp Tyr Ala Met His Trp Val Arg Gln Ala Pro Gly Lys Gly Leu Glu
        35                  40                  45

Trp Val Ser Ser Ile Ser Trp Asn Ser Gly Ser Arg Gly Tyr Ala Asp
    50                  55                  60

Ser Val Lys Gly Arg Phe Thr Ile Ser Arg Asp Asn Ala Lys Asn Ser
65                  70                  75                  80

Leu Phe Leu Gln Met Asn Ser Leu Arg Thr Glu Asp Thr Ala Leu Tyr
                85                  90                  95

Tyr Cys Ala Lys Gly Val Val Tyr Ser Ser Pro Tyr Tyr Gly Met Asp
            100                 105                 110

Val Trp Gly Gln Gly Thr Thr Val Thr Val Ser Ser
            115                 120

<210> SEQ ID NO 16
<211> LENGTH: 110
<212> TYPE: PRT
<213> ORGANISM: homo sapians

<400> SEQUENCE: 16

Gln Ser Ala Leu Thr Gln Pro Pro Ser Ala Ser Gly Thr Pro Gly Gln
1               5                   10                  15

Arg Val Thr Ile Ser Cys Ser Gly Ser Ser Asn Ile Gly Thr Asn
            20                  25                  30

Thr Val Asn Trp Tyr Gln Gln Leu Pro Gly Thr Ala Pro Arg Leu Leu
        35                  40                  45

Ile Tyr Phe Asn Asn Gln Arg Pro Ser Gly Val Pro Asp Arg Phe Ser
    50                  55                  60

Gly Ser Lys Ser Ala Thr Ser Ala Ser Leu Ala Ile Ser Gly Leu Gln
65                  70                  75                  80

Ser Glu Asp Glu Ala Asp Tyr Tyr Cys Ser Ala Trp Asp Ile Leu
                85                  90                  95

Asn Asp Pro Val Phe Gly Gly Gly Thr Lys Leu Thr Val Leu
            100                 105                 110

<210> SEQ ID NO 17
<211> LENGTH: 117
<212> TYPE: PRT
<213> ORGANISM: homo sapians

<400> SEQUENCE: 17

Met Ala Gln Val Gln Leu Val Gln Ser Gly Ala Glu Val Lys Lys Pro
1               5                   10                  15

Gly Ala Ser Val Lys Ile Ser Cys Lys Ala Ser Gly Tyr Ile Phe Asn
            20                  25                  30

Thr Tyr Ser Ile His Trp Val Arg Gln Ala Pro Gly Gln Ser Phe Glu
        35                  40                  45

Trp Met Gly Trp Ser Ser Ala Gly Asp Asp Asn Thr Lys Tyr Ser Asp
    50                  55                  60

Asp Phe His His Arg Leu Thr Ile Ala Arg Asp Thr Ser Ala Ser Thr
65                  70                  75                  80
```

Val Tyr Met Glu Leu Arg Gly Leu Thr Ser Asp Asp Thr Ala Ile Tyr
                85                  90                  95

Tyr Cys Ala Arg Gly Tyr Glu Leu Asp Phe Trp Gly Gln Gly Thr Leu
            100                 105                 110

Val Thr Val Ser Ser
        115

<210> SEQ ID NO 18
<211> LENGTH: 117
<212> TYPE: PRT
<213> ORGANISM: homo sapaians

<400> SEQUENCE: 18

Met Ala Gln Val Gln Leu Val Gln Ser Gly Ala Glu Val Lys Lys Pro
1               5                   10                  15

Gly Ala Ser Val Lys Ile Ser Cys Lys Ala Ser Gly Tyr Ile Phe Asn
            20                  25                  30

Thr Tyr Ser Ile His Trp Val Arg Gln Ala Pro Gly Gln Ser Phe Glu
        35                  40                  45

Trp Met Gly Trp Ser Ser Ala Gly Asp Asp Asn Thr Lys Tyr Ser Asp
    50                  55                  60

Asp Phe His His Arg Leu Thr Ile Ala Arg Thr Ser Ala Ser Thr
65                  70                  75                  80

Val Tyr Met Glu Leu Arg Gly Leu Thr Ser Asp Asp Thr Ala Ile Tyr
                85                  90                  95

Tyr Cys Ala Arg Gly Tyr Glu Leu Asp Phe Trp Gly Gln Gly Thr Leu
            100                 105                 110

Val Thr Val Ser Ser
        115

<210> SEQ ID NO 19
<211> LENGTH: 120
<212> TYPE: PRT
<213> ORGANISM: homo sapians
<220> FEATURE:
<221> NAME/KEY: misc_feature
<222> LOCATION: (20)..(20)
<223> OTHER INFORMATION: Xaa can be any naturally occurring amino acid

<400> SEQUENCE: 19

Met Ala Glu Val Gln Leu Val Glu Ser Gly Gly Asp Leu Val Lys Pro
1               5                   10                  15

Gly Gly Ser Xaa Arg Leu Ser Cys Ala Ala Ser Gly Phe Ser Phe Ser
            20                  25                  30

Asp Tyr Tyr Met Ser Trp Ile Arg Gln Ala Pro Gly Lys Gly Leu Glu
        35                  40                  45

Trp Val Ser Ser Ile Ser Ser Ser Ser Tyr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Ala Pro Arg Tyr Gly Met Asp Val Trp Gly Gln
            100                 105                 110

Gly Thr Thr Val Thr Val Ser Ser
        115                 120

```
<210> SEQ ID NO 20
<211> LENGTH: 111
<212> TYPE: PRT
<213> ORGANISM: homo sapians

<400> SEQUENCE: 20

Gln Ser Ala Leu Thr Gln Pro Ala Ser Val Ser Gly Ser Pro Gly Gln
1               5                   10                  15

Thr Ile Thr Ile Ser Cys Ala Gly Thr Pro Ser Asp Ile Gly Leu Tyr
            20                  25                  30

Asn Tyr Val Ala Trp Phe Gln His Pro Gly Lys Ala Pro Lys Leu
        35                  40                  45

Ile Ile Tyr Asp Val Thr Lys Arg Pro Ser Gly Thr Ser Asn Arg Phe
    50                  55                  60

Ser Gly Ser Lys Ser Gly Asn Thr Ala Ser Leu Thr Ile Ser Gly Leu
65                  70                  75                  80

Gln Ala Asp Asp Glu Ala Asp Tyr Phe Cys Ser Ser Tyr Thr Thr Ser
                85                  90                  95

Asn Ser Phe Val Leu Phe Gly Glu Gly Thr Lys Leu Thr Val Leu
            100                 105                 110

<210> SEQ ID NO 21
<211> LENGTH: 127
<212> TYPE: PRT
<213> ORGANISM: homo sapians

<400> SEQUENCE: 21

Met Ala Gln Val Gln Leu Val Gln Ser Gly Ala Glu Val Lys Lys Pro
1               5                   10                  15

Gly Ser Ser Val Lys Val Ser Cys Lys Ala Ser Gly Gly Thr Phe Ser
            20                  25                  30

Ser Tyr Ala Ile Ser Trp Val Arg Gln Ala Pro Gly Gln Gly Leu Glu
        35                  40                  45

Trp Met Gly Gly Ile Ile Pro Ile Phe Gly Thr Ala Asn Tyr Ala Gln
    50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Gly Ser Glu Arg Val Tyr Ser Ser His Thr Tyr Tyr
            100                 105                 110

Gly Met Asp Val Trp Gly Gln Gly Thr Thr Val Thr Val Ser Ser
        115                 120                 125

<210> SEQ ID NO 22
<211> LENGTH: 110
<212> TYPE: PRT
<213> ORGANISM: homo sapians

<400> SEQUENCE: 22

Gln Ser Val Val Thr Gln Gln Pro Ser Val Ser Ala Ala Pro Gly Gln
1               5                   10                  15

Lys Val Thr Ile Ser Cys Ser Gly Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60
```

Gly Ser Lys Ser Gly Ser Ala Ser Leu Ala Ile Thr Gly Leu Gln
65                  70                  75                  80

Ala Glu Asp Glu Ala Asp Tyr Tyr Cys Gln Ser Tyr Asp Ser Ser Leu
                85                  90                  95

Ser Gly Tyr Val Phe Gly Thr Gly Thr Lys Leu Thr Val Leu
            100                 105                 110

<210> SEQ ID NO 23
<211> LENGTH: 123
<212> TYPE: PRT
<213> ORGANISM: homo sapians

<400> SEQUENCE: 23

Met Ala Gln Val Gln Leu Val Glu Ser Gly Ala Glu Val Lys Lys Pro
1               5                   10                  15

Gly Ala Ser Val Lys Val Ser Cys Lys Ala Ser Gly Tyr Thr Phe Thr
                20                  25                  30

Asn Tyr Tyr Ile His Trp Val Arg Gln Ala Pro Gly Gln Gly Leu Glu
            35                  40                  45

Trp Met Gly Ile Ile Asn Pro Ser Gly Ser Thr Asn Tyr Ala Gln
50                  55                  60

Lys Phe Gln Gly Arg Val Thr Met Thr Arg Asp Thr Ser Thr Ser Thr
65                  70                  75                  80

Val Tyr Met Glu Leu Ser Ser Leu Arg Ser Glu Asp Thr Ala Val Tyr
                85                  90                  95

Tyr Cys Ala Arg Gln Arg Trp Asp Leu Leu Asp Asp Ala Phe Asp Ile
            100                 105                 110

Trp Gly Gln Gly Thr Met Val Thr Val Ser Ser
        115                 120

<210> SEQ ID NO 24
<211> LENGTH: 113
<212> TYPE: PRT
<213> ORGANISM: homo sapians

<400> SEQUENCE: 24

Asp Ile Val Met Thr Gln Ser Pro Asp Ser Leu Ala Val Ser Leu Gly
1               5                   10                  15

Glu Arg Ala Thr Ile Asn Cys Lys Thr Ser Gln Ser Val Leu Tyr Asn
                20                  25                  30

Ala Asn Asn Lys Asn Tyr Leu Asn Trp Tyr Gln Gln Lys Pro Gly Gln
            35                  40                  45

Pro Pro Lys Leu Leu Ile Tyr Trp Ala Ser Ala Arg Glu Ser Gly Val
50                  55                  60

Pro Asp Arg Phe Ser Gly Ser Gly Ser Gly Thr Asp Phe Thr Leu Thr
65                  70                  75                  80

Ile Arg Ser Leu Gln Pro Asp Asp Phe Ala Thr Tyr Tyr Cys Gln Gln
                85                  90                  95

Ala Ile Ser Phe Pro Leu Thr Phe Gly Gly Gly Thr Lys Val Glu Ile
            100                 105                 110

Lys

<210> SEQ ID NO 25
<211> LENGTH: 119
<212> TYPE: PRT
<213> ORGANISM: homo sapians

```
<400> SEQUENCE: 25

Met Ala Glu Val Gln Leu Val Glu Ser Gly Gly Gly Val Gln Pro
1               5                   10                  15

Gly Arg Ser Leu Arg Leu Ser Cys Ala Ala Ser Gly Phe Thr Phe Ser
            20                  25                  30

Ser Tyr Gly Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Trp Ser Gly Pro Ile Thr Leu Trp Gly Gln Gly
            100                 105                 110

Thr Leu Val Thr Val Ser Ser
        115

<210> SEQ ID NO 26
<211> LENGTH: 109
<212> TYPE: PRT
<213> ORGANISM: homo sapians

<400> SEQUENCE: 26

Ser Tyr Glu Leu Met Gln Pro Pro Ser Val Ser Glu Ala Pro Gly Met
1               5                   10                  15

Thr Ala Gln Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Glu Arg Pro Ser Gly Ile Pro Asp Arg Phe Ser Gly Ser
    50                  55                  60

Asn Ser Gly Asn Thr Ala Ser Leu Thr Ile Asn Arg Val Glu Ala Gly
65                  70                  75                  80

Asp Glu Ala Asp Tyr Tyr Cys Gln Val Trp Asp Ser Ser Ser Asp His
                85                  90                  95

His Val Val Phe Gly Gly Gly Thr Lys Leu Thr Val Leu
            100                 105

<210> SEQ ID NO 27
<211> LENGTH: 120
<212> TYPE: PRT
<213> ORGANISM: homo sapians

<400> SEQUENCE: 27

Met Ala Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Glu Met Asn Trp Val Arg Gln Ala Pro Gly Lys Gly Leu Glu
        35                  40                  45

Trp Val Ser Tyr Ile Ser Ser Gly Ser Thr Ile Tyr Tyr Ala Asp
    50                  55                  60

Ser Val Lys Gly Arg Phe Thr Ile Ser Arg Asp Asn Ala Lys Asn Ser
65                  70                  75                  80
```

```
Leu Tyr Leu Gln Met Asn Gly Leu Arg Ala Glu Asp Thr Ala Val Tyr
                 85                  90                  95

Tyr Cys Ala Arg Glu Gly Asp Ser Ser Gly Phe Asp Tyr Trp Gly Gln
            100                 105                 110

Gly Thr Leu Val Thr Val Ser Ser
        115                 120

<210> SEQ ID NO 28
<211> LENGTH: 110
<212> TYPE: PRT
<213> ORGANISM: homo sapians

<400> SEQUENCE: 28

Gln Ser Ala Leu Thr Gln Pro Pro Ser Met Ser Ala Ala Pro Gly Gln
1               5                   10                  15

Lys Val Thr Ile Ser Cys Ser Gly Thr Ser Ser Asn Ile Gly Asn His
            20                  25                  30

Tyr Val Ser Trp Tyr Gln Arg Leu Pro Asp Thr Ala Pro Lys Leu Leu
            35                  40                  45

Ile Tyr Asp Asn Asn Arg Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Tyr Val Phe Gly Thr Gly Thr Lys Val Thr Val Leu
            100                 105                 110

<210> SEQ ID NO 29
<211> LENGTH: 110
<212> TYPE: PRT
<213> ORGANISM: homo sapians

<400> SEQUENCE: 29

Gln Ser Ala Leu Thr Gln Pro Pro Ser Met Ser Ala Ala Pro Gly Gln
1               5                   10                  15

Lys Val Thr Ile Ser Cys Ser Gly Thr Ser Ser Asn Ile Gly Asn His
            20                  25                  30

Tyr Val Ser Trp Tyr Gln Arg Leu Pro Asp Thr Ala Pro Lys Leu Leu
            35                  40                  45

Ile Tyr Asp Asn Asn Arg Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Tyr Val Phe Gly Thr Gly Thr Lys Val Thr Val Leu
            100                 105                 110

<210> SEQ ID NO 30
<211> LENGTH: 112
<212> TYPE: PRT
<213> ORGANISM: homo sapians
```

<400> SEQUENCE: 30

Asp Ile Val Met Thr Gln Thr Pro Leu Phe Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Ile Arg Asp Ser Gly Val Pro
    50                  55                  60

Gly Arg Phe Ser Gly Ser Gly Ser Gly Thr Asp Phe Thr Leu Lys Ile
65                  70                  75                  80

Ser Ser Val Glu Ala Glu Asp Ile Gly Val Tyr Tyr Cys Met Gln Gly
                85                  90                  95

Thr Asp Arg Pro Tyr Thr Phe Gly Gln Gly Thr Lys Leu Glu Ile Lys
            100                 105                 110

<210> SEQ ID NO 31
<211> LENGTH: 120
<212> TYPE: PRT
<213> ORGANISM: homo sapians

<400> SEQUENCE: 31

Met Ala Gln Met Gln Leu Val Gln Ser Gly Gly Gly Val Val Gln Pro
1               5                   10                  15

Gly Arg Ser Leu Arg Leu Ser Cys Val Val Ser Gly Phe Thr Phe Asn
            20                  25                  30

Asp Tyr Pro Met His Trp Val Arg Gln Ala Pro Gly Lys Gly Leu Glu
        35                  40                  45

Trp Val Ala Leu Leu Ser Tyr Asp Gly Thr Ser Ala Tyr Tyr Ala Asp
    50                  55                  60

Ser Val Glu Gly Arg Phe Thr Ile Ser Arg Asp Asn Ser Lys Asn Thr
65                  70                  75                  80

Leu Tyr Leu Gln Met Asn Thr Leu Arg Thr Glu Asp Thr Ala Val Tyr
                85                  90                  95

Tyr Cys Ala Ser Glu Gly Ser Pro Asp Ala Phe Asp Ile Trp Gly Gln
            100                 105                 110

Gly Thr Met Val Thr Val Ser Ser
        115                 120

<210> SEQ ID NO 32
<211> LENGTH: 111
<212> TYPE: PRT
<213> ORGANISM: homo sapians

<400> SEQUENCE: 32

Gln Ala Gly Leu Thr Gln Ser Pro Ser Val Ser Ala Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                    85                  90                  95

Leu Ser Gly Ser Val Phe Gly Gly Gly Thr Lys Val Thr Val Leu
                100                 105                 110

<210> SEQ ID NO 33
<211> LENGTH: 125
<212> TYPE: PRT
<213> ORGANISM: homo sapians

<400> SEQUENCE: 33

Met Ala Gln Val Gln Leu Val Gln Ser Gly Ala Glu Val Lys Lys Pro
1               5                   10                  15

Gly Glu Ser Leu Lys Ile Ser Cys Lys Gly Ser Gly Tyr Ser Phe Thr
                20                  25                  30

Ser Tyr Trp Ile Gly Trp Val Arg Gln Met Pro Gly Lys Gly Leu Glu
            35                  40                  45

Trp Met Gly Ile Ile Tyr Pro Gly Asp Ser Asp Thr Arg Tyr Ser Pro
        50                  55                  60

Ser Phe Gln Gly Gln Val Thr Ile Ser Ala Asp Lys Ser Ile Ser Thr
65                  70                  75                  80

Ala Tyr Leu Gln Trp Ser Ser Leu Lys Ala Ser Asp Thr Ala Met Tyr
                85                  90                  95

Tyr Cys Ala Arg Leu Asp Tyr Asp Ser Ser Gly Tyr Tyr Gly Ala Phe
                100                 105                 110

Asp Ile Trp Gly Gln Gly Thr Met Val Thr Val Ser Ser
            115                 120                 125

<210> SEQ ID NO 34
<211> LENGTH: 110
<212> TYPE: PRT
<213> ORGANISM: homo sapians

<400> SEQUENCE: 34

Gln Ser Val Val Thr Gln Pro Ala Ser Val Ser Gly Ser Pro Gly Gln
1               5                   10                  15

Ser Ile Thr Ile Ser Cys Thr Gly Thr Thr Asp Val Gly Ala Tyr
                20                  25                  30

Asn Tyr Val Ser Trp Tyr Gln His Pro Gly Lys Ala Pro Lys Leu
            35                  40                  45

Ile Ile Tyr Asp Leu Asn Asn Arg Pro Ser Gly Ile Ser Asn Arg Phe
        50                  55                  60

Ser Gly Phe Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
                100                 105                 110

<210> SEQ ID NO 35
<211> LENGTH: 125
<212> TYPE: PRT
<213> ORGANISM: homo sapians

<400> SEQUENCE: 35

Met Ala Gln Val Gln Leu Val Glu Ser Gly Ala Glu Val Lys Lys Pro
1               5                   10                  15

Gly Ala Ser Val Lys Val Ser Cys Lys Ala Ser Gly Tyr Thr Phe Thr
            20                  25                  30

Ser Tyr Tyr Met His Trp Val Arg Gln Ala Pro Gly Gln Gly Leu Gln
        35                  40                  45

Trp Met Gly Ile Ile Asn Pro Ser Gly Gly Ser Thr Ser Tyr Ala Gln
50                  55                  60

Asn Phe Gln Gly Arg Val Thr Met Thr Arg Asp Thr Ser Thr Ser Thr
65                  70                  75                  80

Val Tyr Met Glu Leu Ser Ser Leu Ile Ser Glu Asp Thr Ala Val Tyr
                85                  90                  95

Tyr Cys Ala Arg Ser Gly Tyr Ser Ser Trp Leu Ser Tyr Gly Met
            100                 105                 110

Asp Val Trp Gly Gln Gly Thr Thr Val Thr Val Ser Ser
            115                 120                 125

<210> SEQ ID NO 36
<211> LENGTH: 110
<212> TYPE: PRT
<213> ORGANISM: homo sapians

<400> SEQUENCE: 36

Gln Ala Gly Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Phe Thr Thr Ser
                85                  90                  95

Ser Thr Trp Val Phe Gly Gly Gly Thr Gln Leu Thr Val Leu
            100                 105                 110

<210> SEQ ID NO 37
<211> LENGTH: 125
<212> TYPE: PRT
<213> ORGANISM: homo sapians

<400> SEQUENCE: 37

Met Ala Glu Val Gln Leu Val Gln Ser Gly Ala Glu Val Lys Lys Pro
1               5                   10                  15

Gly Ala Ser Val Lys Leu Ser Cys Lys Ala Ser Gly Tyr Thr Phe Asn
            20                  25                  30

Asn Tyr Ala Thr Ile Trp Val Arg Gln Ala Pro Glu Gln Gly Leu Glu
        35                  40                  45

Tyr Val Gly Trp Ile Ser Ala Tyr Ser Gly His Thr Asn Tyr Ala Gln
50                  55                  60

Lys Leu Gln Gly Arg Val Ser Met Thr Thr Asp Thr Ser Thr Thr Thr
65                  70                  75                  80

Ala Tyr Met Glu Leu Arg Ser Leu Arg Ser Asp Asp Thr Ala Val Tyr
                85                  90                  95

Tyr Cys Ala Arg Trp Ser Gly Trp Gly Ser Tyr His Leu Leu Gly Met
                100                 105                 110

Asp Val Trp Gly Gln Gly Thr Thr Val Thr Val Ser Ser
                115                 120                 125

<210> SEQ ID NO 38
<211> LENGTH: 110
<212> TYPE: PRT
<213> ORGANISM: homo sapians

<400> SEQUENCE: 38

Gln Pro Val Leu Thr Gln Pro Pro Ser Ala Ser Gly Thr Pro Gly Gln
1               5                   10                  15

Arg Val Thr Ile Tyr Cys Ser Gly Ser Asn Ser Asn Ile Gly Gly Asn
                20                  25                  30

Ser Val Asn Trp Tyr Gln Gln Leu Pro Gly Thr Ala Pro Lys Leu Leu
                35                  40                  45

Ile Tyr His Asn Asn Gln Arg Pro Ser Gly Val Pro Asp Arg Phe Ser
            50                  55                  60

Gly Ser Arg Ser Gly Thr Ser Ala Ser Leu Ala Ile Ser Gly Leu Gln
65                  70                  75                  80

Ser Gly Asp Glu Ala Asp Tyr Ser Cys Ala Ala Trp Asp Asp Ser Leu
                85                  90                  95

Arg Gly Tyr Val Phe Gly Thr Gly Thr Lys Val Thr Val Leu
                100                 105                 110

<210> SEQ ID NO 39
<211> LENGTH: 122
<212> TYPE: PRT
<213> ORGANISM: homo sapians

<400> SEQUENCE: 39

Met Ala Gln Val Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Thr
                20                  25                  30

Gly Tyr Tyr Met His Trp Val Arg Gln Ala Thr Gly Gly Leu Glu
                35                  40                  45

Trp Leu Gly Trp Met Asn Pro Lys Thr Gly Val Thr Gly Tyr Ala Gln
            50                  55                  60

Lys Phe Gln Gly Arg Val Thr Met Thr Arg Asn Thr Ser Ile Asn Thr
65                  70                  75                  80

Ala Tyr Met Glu Leu Asn Ser Leu Thr Ser Glu Asp Thr Ala Asp Tyr
                85                  90                  95

Tyr Cys Ala Arg Gly Asp Tyr Gly Gly Pro Gln Asp Met Asp Val Trp
                100                 105                 110

Gly Gln Gly Thr Thr Val Thr Val Ser Ser
                115                 120

<210> SEQ ID NO 40
<211> LENGTH: 110
<212> TYPE: PRT
<213> ORGANISM: homo sapians

<400> SEQUENCE: 40

Gln Ala Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Thr Ser Tyr Thr Ser Ser
                85                  90                  95

Asn Thr Arg Met Phe Gly Gly Gly Thr Lys Leu Thr Val Leu
            100                 105                 110

<210> SEQ ID NO 41
<211> LENGTH: 133
<212> TYPE: PRT
<213> ORGANISM: homo sapians

<400> SEQUENCE: 41

Met Ala Glu Val Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Thr
            20                  25                  30

Gly Tyr Tyr Met His Trp Val Arg Gln Ala Pro Gly Gln Gly Leu Glu
        35                  40                  45

Trp Met Gly Trp Ile Asn Pro Asn Ser Gly Gly Thr Asn Tyr Ala Gln
    50                  55                  60

Lys Phe Gln Gly Arg Val Thr Met Thr Arg Asp Thr Ser Ile Ser Thr
65                  70                  75                  80

Ala Tyr Met Glu Leu Ser Arg Leu Arg Ser Asp Asp Thr Ala Val Tyr
                85                  90                  95

Tyr Cys Ala Arg Asp Leu Gln Gly Ile Thr Ile Phe Gly Val Ala Asn
            100                 105                 110

Ser Pro Pro Tyr Tyr Tyr Gly Met Asp Val Trp Gly Gln Gly Thr Thr
        115                 120                 125

Val Thr Val Ser Ser
    130

<210> SEQ ID NO 42
<211> LENGTH: 110
<212> TYPE: PRT
<213> ORGANISM: homo sapians

<400> SEQUENCE: 42

Gln Ala Val Leu Thr Gln Pro Arg Ser Val Ser Gly Ser Pro Gly Gln
1               5                   10                  15

Ser Val Thr Ile Ser Cys Thr Gly Thr Arg Ser Asp Val Gly Thr Tyr
            20                  25                  30

Asn Tyr Val Ser Trp Tyr Gln Gln Leu Pro Gly Lys Ala Pro Lys Leu
        35                  40                  45

Met Ile His Asp Val Ser Lys Arg Pro Ser Gly Val Pro Asp Arg Leu
    50                  55                  60

```
Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ile Ser Tyr Thr Leu His
                 85                  90                  95

Arg Thr Trp Met Phe Gly Gly Gly Thr Lys Leu Thr Val Leu
            100                 105                 110

<210> SEQ ID NO 43
<211> LENGTH: 117
<212> TYPE: PRT
<213> ORGANISM: homo sapians

<400> SEQUENCE: 43

Met Ala Glu Val Gln Leu Val Gln Ser Gly Ala Glu Val Lys Lys Pro
 1               5                  10                  15

Gly Ala Ser Val Lys Ile Ser Cys Lys Ala Ser Gly Tyr Ile Phe Asn
                 20                  25                  30

Thr Tyr Ser Ile His Trp Val Arg Gln Ala Pro Gly Gln Ser Phe Glu
             35                  40                  45

Trp Met Gly Trp Ser Ser Ala Gly Asp Asp Asn Thr Lys Tyr Ser Asp
 50                  55                  60

Asp Phe His His Arg Leu Thr Ile Ala Arg Thr Ser Ala Ser Thr
 65                  70                  75                  80

Val Tyr Met Glu Leu Arg Gly Leu Thr Ser Asp Asp Thr Ala Ile Tyr
                 85                  90                  95

Tyr Cys Ala Arg Gly Tyr Glu Leu Asp Phe Trp Gly Gln Gly Thr Leu
            100                 105                 110

Val Thr Val Ser Ser
            115

<210> SEQ ID NO 44
<211> LENGTH: 111
<212> TYPE: PRT
<213> ORGANISM: homo sapians

<400> SEQUENCE: 44

Gln Pro Val Leu Thr Gln Pro Ser Val Ser Gly Thr Pro Gly Gln
 1               5                  10                  15

Arg Val Ser Ile Ser Cys Ser Gly Ser Ser Asn Ile Gly Ser Asn
                 20                  25                  30

Ser Val Asn Trp Tyr Gln Gln Leu Pro Gly Thr Ala Pro Arg Leu Leu
             35                  40                  45

Ile Tyr Asn Asn Asp Gln Arg Pro Ser Gly Val Pro Asp Arg Phe Ser
 50                  55                  60

Ala Ser Lys Ser Gly Thr Ser Ala Ser Leu Ala Ile Gly Gly Leu Gln
 65                  70                  75                  80

Ser Glu Asp Glu Gly Asp Tyr Tyr Cys Ser Ala Trp Asp Ser Leu
                 85                  90                  95

Asn Gly Pro Trp Val Phe Gly Gly Gly Thr Lys Leu Thr Val Leu
            100                 105                 110

<210> SEQ ID NO 45
<211> LENGTH: 119
<212> TYPE: PRT
<213> ORGANISM: homo sapians
```

-continued

<400> SEQUENCE: 45

Met Ala Glu Val Gln Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Ser Tyr Ser Met Asn Trp Val Arg Gln Ala Pro Gly Lys Gly Leu Glu
        35                  40                  45

Trp Val Ser Ser Ile Ser Ser Ser Ser Tyr Ile Tyr Tyr Ala Asp Ser
50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Val Gly Ala Thr Met Gly Asp Tyr Trp Gly Gln Gly
            100                 105                 110

Thr Leu Val Thr Val Ser Ser
        115

<210> SEQ ID NO 46
<211> LENGTH: 111
<212> TYPE: PRT
<213> ORGANISM: homo sapians

<400> SEQUENCE: 46

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Ala Asn Asn
            20                  25                  30

Phe Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Ala Gly Asp Glu Ala Asp Tyr Phe Cys Gly Thr Trp Asp Ser Ser Leu
                85                  90                  95

Ser Ala Ser Tyr Val Phe Gly Thr Gly Thr Lys Val Thr Val Leu
            100                 105                 110

<210> SEQ ID NO 47
<211> LENGTH: 123
<212> TYPE: PRT
<213> ORGANISM: homo sapians

<400> SEQUENCE: 47

Met Ala Gln Val Gln Leu Val Gln Ser Gly Ala Glu Val Lys Lys Pro
1               5                   10                  15

Gly Glu Ser Leu Lys Ile Ser Cys Lys Gly Ser Gly Tyr Ser Phe Thr
            20                  25                  30

Ser Tyr Trp Ile Gly Trp Val Arg Gln Met Pro Gly Lys Gly Leu Glu
        35                  40                  45

Trp Met Gly Ile Ile Tyr Pro Gly Asp Ser Asp Thr Arg Tyr Ser Pro
50                  55                  60

```
Ser Phe Gln Gly Gln Val Thr Ile Ser Ala Asp Lys Ser Thr Ser Thr
 65                  70                  75                  80

Ala Tyr Leu Gln Trp Ser Ser Leu Lys Ala Ser Asp Thr Ala Met Tyr
                 85                  90                  95

Tyr Cys Ala Arg Leu Gly Ser Ser Gly Trp Tyr Asp Ala Phe Asp Ile
            100                 105                 110

Trp Gly Gln Gly Thr Met Val Thr Val Ser Ser
            115                 120

<210> SEQ ID NO 48
<211> LENGTH: 107
<212> TYPE: PRT
<213> ORGANISM: homo sapians

<400> SEQUENCE: 48

Asp Ile Val Met Thr Gln Ser Pro Ser Ser Val Ser Ala Phe Val Gly
  1               5                  10                  15

Asp Arg Val Thr Ile Thr Cys Arg Ala Ser Gln Asp Val Gly Ser Trp
                 20                  25                  30

Leu Val Trp Tyr Gln Gln Lys Pro Gly Lys Val Pro Lys Leu Leu Ile
             35                  40                  45

Tyr Gly Ala Ser Thr Leu Gln Ser Gly Val Pro Ser Arg Phe Ser Gly
 50                  55                  60

Gly Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Lys Ser Leu Pro Tyr
                 85                  90                  95

Thr Phe Gly Gln Gly Thr Lys Leu Glu Ile Lys
            100                 105

<210> SEQ ID NO 49
<211> LENGTH: 119
<212> TYPE: PRT
<213> ORGANISM: homo sapians

<400> SEQUENCE: 49

Met Ala Gln Val Gln Leu Val Gln Ser Gly Gly Gly Leu Val Lys Pro
  1               5                  10                  15

Gly Gly Ser Leu Arg Leu Ser Cys Ala Ala Ser Gly Phe Thr Phe Ser
                 20                  25                  30

Ser Tyr Ser Met Asn Trp Val Arg Gln Ala Pro Gly Lys Gly Leu Glu
             35                  40                  45

Trp Val Ser Ser Ile Ser Ser Ser Ser Tyr Ile Tyr Tyr Ala Asp
 50                  55                  60

Ser Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                 85                  90                  95

Tyr Cys Ala Arg Val Gly Ala Thr Met Gly Asp Tyr Trp Gly Gln Gly
            100                 105                 110

Thr Leu Val Thr Val Ser Ser
            115

<210> SEQ ID NO 50
<211> LENGTH: 110
<212> TYPE: PRT
<213> ORGANISM: homo sapians
```

<400> SEQUENCE: 50

Leu Pro Val Leu Thr Gln Pro Ala Ser Val Ser Gly Ser Pro Gly Gln
1               5                   10                  15

Ser Ile Thr Ile Ser Cys Thr Gly Thr Asp Ser Asp Val Gly Gly Tyr
                20                  25                  30

Asn Tyr Val Ser Trp Tyr Gln Gln His Pro Gly Lys Ala Pro Lys Leu
            35                  40                  45

Ile Ile Ser Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65              70                  75                  80

Gln Ala Asp Asp Glu Ala Asp Tyr Tyr Cys Asn Ser Tyr Thr Val His
                85                  90                  95

Ala Thr Val Leu Phe Gly Gly Gly Thr Lys Val Thr Val Leu
            100                 105                 110

<210> SEQ ID NO 51
<211> LENGTH: 122
<212> TYPE: PRT
<213> ORGANISM: homo sapians

<400> SEQUENCE: 51

Met Ala Glu Val Gln Leu Leu Glu Ser Gly Gly Gly Leu Val Lys Pro
1               5                   10                  15

Arg Gly Ser Leu Arg Leu Ser Cys Ala Ala Ser Gly Phe Thr Phe Ser
                20                  25                  30

Asn Ala Trp Met Ser Trp Val Arg Gln Ala Pro Gly Lys Gly Leu Glu
            35                  40                  45

Trp Val Gly Arg Ile Lys Ser Lys Thr Asp Gly Thr Thr Asp Tyr
        50                  55                  60

Ala Ala Pro Val Lys Gly Arg Phe Thr Ile Ser Arg Asp Asp Ser Lys
65              70                  75                  80

Asn Thr Leu Tyr Leu Gln Met Asn Ser Leu Lys Thr Glu Asp Thr Ala
                85                  90                  95

Val Tyr Tyr Cys Thr Thr Val Trp Arg Phe Gly Glu Leu Phe Arg Trp
            100                 105                 110

Gly Gln Gly Thr Leu Val Thr Val Ser Ser
            115                 120

<210> SEQ ID NO 52
<211> LENGTH: 105
<212> TYPE: PRT
<213> ORGANISM: homo sapians

<400> SEQUENCE: 52

Gln Ala Gly Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ile
                20                  25                  30

Ser Trp Tyr Gln Gln Lys Pro Gly Gln Ser Pro Val Met Val Ile Phe
            35                  40                  45

Gln Asp Thr Lys Arg Pro Ser Gly Ile Pro Glu Arg Phe Ser Gly Ser
        50                  55                  60

```
Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Thr Ser Thr Val Phe
                 85                  90                  95

Gly Gly Gly Thr Lys Leu Thr Val Leu
            100                 105
```

<210> SEQ ID NO 53
<211> LENGTH: 121
<212> TYPE: PRT
<213> ORGANISM: homo sapians

<400> SEQUENCE: 53

```
Met Ala Glu Val Gln Leu Val Gln Ser Gly Ser Glu Leu Lys Lys Pro
 1               5                  10                  15

Gly Ala Ser Val Lys Ile Ser Cys Lys Ala Ser Gly Tyr Thr Leu Thr
                 20                  25                  30

Asn His Ala Leu Asn Trp Val Arg Gln Ala Pro Gly Gln Gly Leu Glu
             35                  40                  45

Trp Met Ala Trp Met Asn Thr Asn Thr Gly Asn Pro Thr Tyr Ala Gln
 50                  55                  60

Asp Phe Thr Gly Arg Phe Val Phe Ser Leu Asp Thr Ser Val Ser Thr
 65                  70                  75                  80

Ala Tyr Leu Glu Ile Ser Ser Leu Lys Ala Glu Asp Thr Ala Ile Tyr
                 85                  90                  95

Tyr Cys Ala Arg Glu Pro Arg Asp Ala Asp Ala Phe Asp Ile Trp Gly
            100                 105                 110

Gln Gly Thr Met Val Thr Val Ser Ser
            115                 120
```

<210> SEQ ID NO 54
<211> LENGTH: 108
<212> TYPE: PRT
<213> ORGANISM: homo sapians

<400> SEQUENCE: 54

```
Gln Pro Val Leu Thr Gln Pro Ser Val Ser Val Ala Pro Gly Gln
 1               5                  10                  15

Thr Ala Arg Ile Thr Cys Gly Gly Asn Asn Ile Gly Ser Lys Leu Val
                 20                  25                  30

His Trp Tyr Gln Gln Lys Pro Gly Gln Ala Pro Val Leu Val Val Tyr
             35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp Leu
                 85                  90                  95

Val Val Phe Gly Gly Gly Thr Lys Leu Thr Val Leu
            100                 105
```

<210> SEQ ID NO 55
<211> LENGTH: 117
<212> TYPE: PRT
<213> ORGANISM: homo sapians

<400> SEQUENCE: 55

Met Ala Gln Val Gln Leu Val Gln Ser Gly Thr Glu Val Lys Lys Pro
1               5                   10                  15

Gly Glu Ser Leu Arg Ile Ser Cys Arg Ser Ser Gly Tyr Lys Phe Thr
            20                  25                  30

Asn Tyr Trp Ile Gly Trp Val Arg Gln Leu Pro Gly Gln Gly Leu Glu
        35                  40                  45

Trp Met Gly Val Ile Leu Pro Gly Asp Ser Asp Thr Arg Tyr Gly Pro
    50                  55                  60

Ser Phe Gln Gly His Val Ser Ile Ser Val Asp Lys Ser Ile Ser Thr
65                  70                  75                  80

Val Tyr Leu Glu Trp Glu Ser Leu Lys Ala Ser Asp Thr Ala Met Tyr
                85                  90                  95

Tyr Cys Ala Ser Trp Asp Asn Phe Asp His Trp Gly Gln Gly Thr Leu
            100                 105                 110

Val Thr Val Ser Ser
            115

<210> SEQ ID NO 56
<211> LENGTH: 110
<212> TYPE: PRT
<213> ORGANISM: homo sapians

<400> SEQUENCE: 56

Gln Ser Val Val Thr Gln Pro Pro Ser Val Ser Ala Ala Pro Arg Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Arg Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Thr Gly Thr Lys Val Thr Val Leu
            100                 105                 110

<210> SEQ ID NO 57
<211> LENGTH: 120
<212> TYPE: PRT
<213> ORGANISM: homo sapians

<400> SEQUENCE: 57

Met Ala Glu Val Gln Leu Val Gln Ser Gly Ala Glu Val Lys Lys Pro
1               5                   10                  15

Gly Thr Ser Val Thr Ile Ser Cys Lys Thr Ser Gly Tyr Thr Phe Thr
            20                  25                  30

Thr Tyr Tyr Ile His Trp Val Arg Gln Ala Pro Gly Gln Gly Leu Glu
        35                  40                  45

Trp Met Gly Ile Ile Leu Pro Ser Gly Gly Asn Thr Asn Tyr Ala Pro
    50                  55                  60

Asn Phe Gln Gly Arg Val Thr Met Thr Arg Asp Thr Ser Thr Ser Thr
65                  70                  75                  80

Val Asn Met Glu Leu Ser Ser Leu Thr Ser Asp Asp Thr Ala Val Tyr
            85                  90                  95

Tyr Cys Val Arg Glu Tyr Arg Gly Gly Tyr Phe Asp Tyr Trp Gly Gln
            100                 105                 110

Gly Thr Leu Val Thr Val Ser Ser
            115                 120

<210> SEQ ID NO 58
<211> LENGTH: 113
<212> TYPE: PRT
<213> ORGANISM: homo sapians

<400> SEQUENCE: 58

Ala Ile Arg Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 59
<211> LENGTH: 125
<212> TYPE: PRT
<213> ORGANISM: homo sapians

<400> SEQUENCE: 59

Met Ala Gln Val Gln Leu Val Glu Ser Gly Ala Glu Val Lys Lys Pro
1               5                   10                  15

Gly Ala Ser Val Lys Val Ser Cys Lys Ala Ser Gly Tyr Thr Phe Thr
            20                  25                  30

Ser Tyr Tyr Met His Trp Val Arg Gln Ala Pro Gly Gln Gly Leu Glu
        35                  40                  45

Trp Met Gly Ile Ile Asn Pro Ser Gly Gly Ser Thr Ser Tyr Ala Gln
    50                  55                  60

Lys Phe Gln Gly Arg Val Thr Met Thr Arg Asp Thr Ser Thr Ser Thr
65                  70                  75                  80

Val Tyr Met Glu Leu Ser Ser Leu Arg Ser Glu Asp Thr Ala Val Tyr
                85                  90                  95

Tyr Cys Ala Arg Glu Gly Ala Asn Ala Pro Asn Ser Tyr Tyr Tyr Met
            100                 105                 110

Asp Val Trp Gly Lys Gly Thr Thr Val Thr Val Ser Ser
            115                 120                 125

<210> SEQ ID NO 60
<211> LENGTH: 111
<212> TYPE: PRT
<213> ORGANISM: homo sapians -continued

<400> SEQUENCE: 60

Gln Ser Val Val Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Lys Gln Leu Pro Gly Thr Ala Pro Lys Leu
        35                  40                  45

Leu Ile Tyr Gly Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Glu Gly Val Phe Gly Thr Gly Thr Lys Val Thr Val Leu
            100                 105                 110

<210> SEQ ID NO 61
<211> LENGTH: 123
<212> TYPE: PRT
<213> ORGANISM: homo sapians

<400> SEQUENCE: 61

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Leu Gly Ala Ala Ser Tyr Trp Tyr Phe Asp Leu
            100                 105                 110

Trp Gly Arg Gly Thr Leu Val Thr Val Ser Ser
        115                 120

<210> SEQ ID NO 62
<211> LENGTH: 107
<212> TYPE: PRT
<213> ORGANISM: homo sapians

<400> SEQUENCE: 62

Asp Ile Gln Leu Thr Gln Ser Pro Pro Ser Val Ser Ala Ser Val Gly
1               5                   10                  15

Asp Arg Val Thr Ile Thr Cys Arg Ala Ser Gln Asp Ile Ser Thr Trp
            20                  25                  30

Leu Ala Trp Tyr Gln Gln Lys Pro Gly Ser Ala Pro Lys Val Leu Ile
        35                  40                  45

Tyr Ala Ala Ser Thr Phe Gln Ser Gly Val Pro Ser Arg Phe Arg Gly
    50                  55                  60

Ser Gly Ser Gly Thr Tyr Phe Thr Leu Thr Ile Ser Gly Leu Gln Pro
 65                  70                  75                  80

Glu Asp Phe Ala Thr Tyr Tyr Cys Gln Gln Gly Asn Ser Phe Pro Pro
                 85                  90                  95

Thr Phe Gly Gln Gly Thr Lys Leu Glu Ile Lys
                100                 105

<210> SEQ ID NO 63
<211> LENGTH: 126
<212> TYPE: PRT
<213> ORGANISM: homo sapians

<400> SEQUENCE: 63

Met Ala Gln Val Gln Leu Val Gln Ser Gly Ala Glu Val Lys Lys Pro
 1               5                  10                  15

Gly Ser Ser Val Lys Val Ser Cys Lys Ala Tyr Gly Gly Thr Phe Gly
                20                  25                  30

Ser Tyr Gly Val Ser Trp Val Arg Arg Ala Pro Gly Gln Gly Leu Glu
            35                  40                  45

Trp Met Gly Arg Leu Ile Pro Ile Phe Gly Thr Arg Asp Tyr Ala Gln
 50                  55                  60

Lys Phe Gln Gly Arg Val Thr Leu Thr Ala Asp Glu Ser Thr Asn Thr
 65                  70                  75                  80

Ala Tyr Met Glu Leu Ser Ser Leu Arg Ser Glu Asp Thr Ala Val Tyr
                85                  90                  95

Tyr Cys Ala Arg Asp Gly Asp Tyr Tyr Gly Ser Gly Ser Tyr Tyr Gly
                100                 105                 110

Met Asp Val Trp Gly Gln Gly Thr Thr Val Thr Val Ser Ser
            115                 120                 125

<210> SEQ ID NO 64
<211> LENGTH: 110
<212> TYPE: PRT
<213> ORGANISM: homo sapians

<400> SEQUENCE: 64

Ser Tyr Glu Leu Thr Gln Pro Ala Ser Val Ser Gly Ser Pro Gly Gln
 1               5                  10                  15

Ser Ile Thr Ile Ser Cys Thr Gly Ser Ser Asp Val Gly Gly Tyr
                20                  25                  30

Asn Phe Val Ser Trp Tyr Arg Gln His Ala Gly Lys Ala Pro Lys Leu
            35                  40                  45

Met Ile Tyr Asp Val Thr Asn Arg Pro Ser Gly Val Ser Thr Arg Phe
 50                  55                  60

Ser Gly Ser Lys Ser Gly Thr Thr Ala Ser Leu Thr Ile Ser Gly Leu
 65                  70                  75                  80

Gln Pro Asp Asp Glu Ala His Tyr Tyr Cys Ser Ser Tyr Thr Thr Thr
                85                  90                  95

Ser Thr Trp Val Phe Gly Gly Gly Thr Lys Leu Thr Val Leu
            100                 105                 110

<210> SEQ ID NO 65
<211> LENGTH: 122
<212> TYPE: PRT
<213> ORGANISM: homo sapians

<400> SEQUENCE: 65

Met Ala Glu Val Gln Leu Val Glu Ser Gly Gly Gly Val Val Gln Pro
1               5                   10                  15

Gly Arg Ser Leu Arg Leu Ser Cys Ala Ala Ser Gly Phe Thr Phe Ser
            20                  25                  30

Ser Tyr Gly Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Gly Tyr Ser Tyr Gly Gly Phe Asp Tyr Trp
            100                 105                 110

Gly Gln Gly Thr Leu Val Thr Val Ser Ser
        115                 120

<210> SEQ ID NO 66
<211> LENGTH: 111
<212> TYPE: PRT
<213> ORGANISM: homo sapians

<400> SEQUENCE: 66

Gln Ser Val Val Thr Gln Pro Pro Ser Val Ser Ala Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ala Asn Asn Asn Arg Pro Ser Gly Val Pro Asp Arg Phe
50                  55                  60

Ser Gly Ser Lys Thr Gly Thr Ser Ala Ser Leu Ala Ile Thr Gly Leu
65                  70                  75                  80

Gln Ala Asp Asp Glu Ala Asp Tyr Phe Cys Gln Ser Tyr Asp Ser Ser
                85                  90                  95

Leu Ser Gly Trp Val Phe Gly Gly Gly Thr Lys Leu Thr Val Leu
            100                 105                 110

<210> SEQ ID NO 67
<211> LENGTH: 115
<212> TYPE: PRT
<213> ORGANISM: homo sapians

<400> SEQUENCE: 67

Met Ala Glu Val Gln Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Ser Tyr Ser Met Asn Trp Val Arg Gln Ala Pro Gly Lys Gly Leu Glu
        35                  40                  45

Trp Val Ser Ser Ile Ser Ser Gly Ser Ser Tyr Ile Tyr Tyr Ala Asp
50                  55                  60

```
Ser Leu Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                 85                  90                  95

Tyr Cys Ala Arg Asp Phe Gly Asn Trp Gly Gln Gly Thr Leu Val Thr
                100                 105                 110

Val Ser Ser
        115

<210> SEQ ID NO 68
<211> LENGTH: 111
<212> TYPE: PRT
<213> ORGANISM: homo sapians

<400> SEQUENCE: 68

Gln Ser Val Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
                 35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Pro Tyr Val Phe Gly Thr Gly Thr Lys Val Thr Val Leu
                100                 105                 110

<210> SEQ ID NO 69
<211> LENGTH: 121
<212> TYPE: PRT
<213> ORGANISM: homo sapians

<400> SEQUENCE: 69

Met Ala Gln Val Gln Leu Val Glu Ser Gly Gly Gly Leu Val Gln Pro
  1               5                  10                  15

Gly Gly Ser Leu Arg Leu Ser Cys Ala Ala Ser Gly Phe Asn Phe Ser
                 20                  25                  30

Ser Tyr Glu Met Asn Trp Val Arg Gln Ala Pro Gly Lys Gly Leu Glu
                 35                  40                  45

Trp Val Ser Tyr Ile Ser Ser Ser Gly Ser Thr Lys His Tyr Ala Asp
 50                  55                  60

Ser Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                 85                  90                  95

Tyr Cys Ala Arg Glu His Tyr Asn Ser Trp Tyr Phe Asp Leu Trp Gly
                100                 105                 110

Arg Gly Thr Leu Val Thr Val Ser Ser
        115                 120

<210> SEQ ID NO 70
<211> LENGTH: 110
<212> TYPE: PRT
<213> ORGANISM: homo sapians
```

-continued

<400> SEQUENCE: 70

Ser Tyr Glu Leu Met Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ala Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ala Asn Val Val Phe Gly Gly Gly Thr Lys Leu Thr Val Leu
            100                 105                 110

<210> SEQ ID NO 71
<211> LENGTH: 123
<212> TYPE: PRT
<213> ORGANISM: homo sapians

<400> SEQUENCE: 71

Met Ala Glu Val Gln Leu Leu Glu Ser Gly Gly Gly Trp Val Lys Pro
1               5                   10                  15

Gly Gly Ser Leu Arg Leu Ser Cys Ala Ala Ser Gly Phe Pro Phe Ser
            20                  25                  30

Asp Tyr Tyr Met Thr Trp Val Arg Gln Ala Pro Gly Lys Gly Leu Glu
        35                  40                  45

Trp Val Ser Tyr Ile Thr Thr Gly Gly Arg Ile Ile Tyr Ser Ala Asp
    50                  55                  60

Ser Val Arg Gly Arg Phe Thr Ile Ser Arg Asp Asn Ala Lys Asn Ser
65                  70                  75                  80

Val Tyr Leu Gln Met Asn Ser Leu Arg Ala Glu Asp Thr Ala Val Tyr
                85                  90                  95

Tyr Cys Ala Arg Pro Leu Arg Glu Leu Ser Pro Gly Gly Phe Asp Leu
            100                 105                 110

Trp Gly Arg Gly Thr Met Val Thr Val Ser Ser
        115                 120

<210> SEQ ID NO 72
<211> LENGTH: 110
<212> TYPE: PRT
<213> ORGANISM: homo sapians

<400> SEQUENCE: 72

Leu Pro Val Leu Thr Gln Pro Pro Ser Val Ser Ala Ala Pro Gly Gln
1               5                   10                  15

Lys Val Thr Ile Pro Cys Ser Gly Thr Tyr Ser Asn Ile Val Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Asn Ser Leu
                85                  90                  95

Arg Arg Trp Val Phe Gly Gly Gly Thr Lys Leu Thr Val Leu
            100                 105                 110

<210> SEQ ID NO 73
<211> LENGTH: 119
<212> TYPE: PRT
<213> ORGANISM: homo sapians

<400> SEQUENCE: 73

Met Ala Glu Val Gln Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
                20                  25                  30

Ser Tyr Ser Met Asn Trp Val Arg Gln Ala Pro Gly Lys Gly Leu Glu
            35                  40                  45

Trp Val Ser Ser Ile Ser Ser Ala Ser Ser Tyr Ile Tyr Tyr Ala Asp
50                  55                  60

Ser Val Lys Gly Arg Phe Thr Ile Ser Arg Asp Asn Ala Lys Lys Ser
65                  70                  75                  80

Leu Tyr Leu Gln Leu Asn Ser Leu Thr Val Glu Asp Thr Ala Val Tyr
                85                  90                  95

Tyr Cys Ala Arg Glu Tyr Trp Gly Ser Pro Asp Tyr Trp Gly Arg Gly
            100                 105                 110

Thr Leu Val Thr Val Ser Ser
        115

<210> SEQ ID NO 74
<211> LENGTH: 110
<212> TYPE: PRT
<213> ORGANISM: homo sapians

<400> SEQUENCE: 74

Gln Pro Val Leu Thr Gln Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Asn Asn Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Gly Gly Thr Lys Leu Thr Val Leu
            100                 105                 110

<210> SEQ ID NO 75
<211> LENGTH: 119
<212> TYPE: PRT
<213> ORGANISM: homo sapians -continued

```
<400> SEQUENCE: 75

Met Ala Glu Val Gln Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Ser Tyr Ser Met Asn Trp Val Arg Gln Ala Pro Gly Lys Gly Leu Glu
        35                  40                  45

Trp Val Ser Ser Ile Ser Ser Ser Ser Tyr Ile Tyr Tyr Ala Asp
50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Gly Gly Val Pro Gly Asp Tyr Trp Gly Gln Gly
            100                 105                 110

Thr Leu Val Thr Val Ser Ser
            115

<210> SEQ ID NO 76
<211> LENGTH: 110
<212> TYPE: PRT
<213> ORGANISM: homo sapians

<400> SEQUENCE: 76

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Tyr Asn Lys Arg Pro Ser Gly Ile Pro Asp Arg Phe Ser
    50                  55                  60

Gly Ser Gln Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Thr Leu Tyr Val Phe Gly Thr Gly Thr Lys Leu Thr Val Leu
            100                 105                 110

<210> SEQ ID NO 77
<211> LENGTH: 126
<212> TYPE: PRT
<213> ORGANISM: homo sapians

<400> SEQUENCE: 77

Met Ala Gln Val Gln Leu Val Gln Ser Gly Ala Glu Val Lys Lys Pro
1               5                   10                  15

Gly Ser Ser Val Lys Val Ser Cys Lys Ala Tyr Gly Gly Thr Phe Gly
            20                  25                  30

Ser Tyr Gly Val Ser Trp Val Arg Arg Ala Pro Gly Gln Gly Leu Glu
        35                  40                  45

Trp Met Gly Arg Leu Ile Pro Ile Phe Gly Thr Arg Asp Tyr Ala Gln
50                  55                  60
```

Lys Phe Gln Gly Arg Val Thr Leu Thr Ala Asp Glu Ser Thr Asn Thr
65                  70                  75                  80

Ala Tyr Met Glu Leu Ser Ser Leu Arg Ser Glu Asp Thr Ala Val Tyr
            85                  90                  95

Tyr Cys Ala Arg Asp Gly Asp Tyr Tyr Gly Ser Gly Ser Tyr Tyr Gly
            100                 105                 110

Met Asp Val Trp Gly Gln Gly Thr Leu Val Thr Val Ser Ser
            115                 120                 125

<210> SEQ ID NO 78
<211> LENGTH: 107
<212> TYPE: PRT
<213> ORGANISM: homo sapians

<400> SEQUENCE: 78

Glu Thr Thr Leu Thr Gln Ser Pro Ala Thr Leu Ser Val Ser Pro Gly
1               5                   10                  15

Glu Arg Ala Thr Val Ser Cys Arg Ala Ser Gln Ser Leu Gly Ser Asn
            20                  25                  30

Leu Gly Trp Phe Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Asn Asp Trp Pro Ile
            85                  90                  95

Thr Phe Gly Gln Gly Thr Arg Leu Glu Ile Lys
            100                 105

<210> SEQ ID NO 79
<211> LENGTH: 128
<212> TYPE: PRT
<213> ORGANISM: homo sapians

<400> SEQUENCE: 79

Met Ala Gln Met Gln Leu Val Gln Ser Gly Ala Glu Val Lys Lys Pro
1               5                   10                  15

Gly Ser Ser Val Lys Val Ser Cys Lys Ala Ser Gly Gly Thr Phe Ser
            20                  25                  30

Ser Tyr Ala Ile Ser Trp Val Arg Gln Ala Pro Gly Gln Gly Leu Glu
        35                  40                  45

Trp Met Gly Arg Ile Ile Pro Ile Leu Gly Ile Ala Asn Tyr Ala Gln
50                  55                  60

Lys Phe Gln Gly Arg Val Thr Ile Thr Ala Asp Lys Ser Thr Ser Thr
65                  70                  75                  80

Ala Tyr Met Glu Leu Ser Ser Leu Arg Ser Glu Asp Thr Ala Val Tyr
            85                  90                  95

Tyr Cys Ala Arg Gly His Asp Tyr Tyr Gly Ser Gly Asn Asn Gln Glu
            100                 105                 110

Asp Tyr Phe Asp Pro Trp Gly Gln Gly Thr Leu Val Thr Val Ser Ser
            115                 120                 125

<210> SEQ ID NO 80
<211> LENGTH: 110
<212> TYPE: PRT
<213> ORGANISM: homo sapians

```
<400> SEQUENCE: 80

Gln Pro Val Leu Thr Gln Pro Pro Ser Val Ser Lys Asp Leu Arg Gln
1               5                   10                  15

Thr Ala Thr Leu Thr Cys Thr Gly Asn Gly Asn Asn Val Gly Tyr Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Phe Ser
    50                  55                  60

Ala Ser Arg Ser Gly Asn Thr Ala Ser Leu Thr Ile Ser Gly Leu Gln
65                  70                  75                  80

Pro Glu Asp Glu Ala Asp Tyr Phe Cys Ser Ala Trp Asp Asn Ser Leu
                85                  90                  95

Ser Ala Trp Val Phe Gly Gly Gly Thr Lys Leu Thr Val Leu
                100                 105                 110

<210> SEQ ID NO 81
<211> LENGTH: 107
<212> TYPE: PRT
<213> ORGANISM: homo sapains

<400> SEQUENCE: 81

Glu Thr Thr Leu Thr Gln Ser Pro Ala Thr Leu Ser Val Ser Pro Gly
1               5                   10                  15

Glu Arg Ala Thr Val Ser Cys Arg Ala Ser Gln Ser Leu Gly Ser Asn
            20                  25                  30

Leu Gly Trp Phe Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Asn Asp Trp Pro Ile
                85                  90                  95

Thr Phe Gly Gln Gly Thr Lys Leu Glu Ile Lys
                100                 105
```